US007381802B2

(12) United States Patent
Riaño-Umbarila et al.

(10) Patent No.: US 7,381,802 B2
(45) Date of Patent: Jun. 3, 2008

(54) **HUMAN ANTIBODIES THAT SPECIFICALLY RECOGNIZE THE TOXIN CN2 FROM *CENTRUROIDES NOXIUS* SCORPION VENOM**

(75) Inventors: Lidia Riaño-Umbarila, Bogota (CO); Baltazar Becerril Lujan, Morelos (MX); Lourival Domingos Possani Postay, Morelos (MX)

(73) Assignee: Universidad Nacional Autónoma De México (UNAM) (MX)

( * ) Notice: Subject to any disclaimer, the term of this patent is extended or adjusted under 35 U.S.C. 154(b) by 0 days.

(21) Appl. No.: 11/404,879

(22) Filed: Apr. 17, 2006

(65) Prior Publication Data

US 2007/0071750 A1 Mar. 29, 2007

Related U.S. Application Data

(60) Provisional application No. 60/671,535, filed on Apr. 15, 2005, provisional application No. 60/672,535, filed on Apr. 19, 2005.

(51) Int. Cl.
*C07K 16/00* (2006.01)
*C12P 21/08* (2006.01)
*A61K 39/395* (2006.01)
*A61K 39/00* (2006.01)

(52) U.S. Cl. ............................. 530/388.25; 530/387.1; 530/388.2; 424/130.1; 424/135.1; 424/172.1

(58) Field of Classification Search ...................... None
See application file for complete search history.

(56) References Cited

U.S. PATENT DOCUMENTS

| | | | |
|---|---|---|---|
| 4,806,346 | A | 2/1989 | Hum et al. |
| 4,814,433 | A | 3/1989 | Fredrickson |
| 4,849,352 | A | 7/1989 | Sullivan et al. |
| 4,940,670 | A | 7/1990 | Rhodes |
| 5,328,834 | A | 7/1994 | Ngo et al. |
| 5,443,976 | A | 8/1995 | Carroll |
| 5,733,742 | A | 3/1998 | Landon |
| 5,888,511 | A | 3/1999 | Skurkovich et al. |
| 5,904,922 | A | 5/1999 | Carroll |
| 6,333,032 | B1 | 12/2001 | Skurkovich et al. |
| 6,448,054 | B1 | 9/2002 | Poznansky et al. |
| 6,534,059 | B2 | 3/2003 | Skurkovich et al. |
| 6,709,655 | B2 | 3/2004 | Lopez de Silanes et al. |
| 2003/0049725 | A1 | 3/2003 | Heavner et al. |
| 2003/0215448 | A1 | 11/2003 | Skurkovich et al. |
| 2003/0223995 | A1 | 12/2003 | Skurkovich et al. |
| 2003/0224005 | A1 | 12/2003 | Skurkovich et al. |
| 2003/0228310 | A1 | 12/2003 | Skurkovich et al. |
| 2004/0062768 | A1 | 4/2004 | SKurkovich et al. |
| 2004/0086508 | A1 | 5/2004 | Skurkovich et al. |

FOREIGN PATENT DOCUMENTS

WO WO 92/22324 A1 12/1992
WO WO 01/58469 A1 8/2001

OTHER PUBLICATIONS

Becerril, B., et al., "Cloning and characterization of cDNAs that code for $Na^+$—channel-blocking toxins of the scorpion *Centruroides noxius* Hoffman," *Gene 128*:165-171, Elsevier Science Publishers B.V. (1993).
Cain, B.S., et al., "The Physiologic Basis for Anticytokine Clinical Trials in the Treatment of Sepsis," *J. Am. Coll. Surg. 186*:337-351, American College of Surgeons (1998).
Calderon-Aranda, E.S., et al., "Neutralizing Capacity of Murine Sera Induced by Different Antigens of Scorpion Venom," *Toxicon 31*:327-337, Pergamon Press Ltd. (1993).
Calderon-Aranda, E.S., et al., "The use of synthetic peptides can be a misleading approach to generate vaccines against scorpion toxins," *Vaccine 13*:1198-1206, Elsevier Science, Ltd. (1995).
Couraud, F., et al., "Two Types of Scorpion Toxin Receptor Sites, One Related to the Activation, the Other to the Inactivation of the Action Potential Sodium Channel," *Toxicon 20*:9-16, Pergamon Press Ltd. (1982).
Dehesa-Dávila, M. and Possani, L.D., "Scorpionism and Serotherapy in Mexico," *Toxicon 32*:1015-1018, Elsevier Science Ltd. (1994).
Dehesa-Dávila, M., et al., "Clinical Toxicology of Scorpion Stings," in *Handbook of Clinical Toxicology of Animal Venoms and Poisons*, Ch. 18, Meier, J., and White, J., eds., CRC Press, Boca Raton, FL, pp. 221-238 (1995).
Dick, A.D., et al., "Neutralizing TNF-alpha Activity Modulates T-cell Phenotype and Function in Experimental Autoimmune Uveoretinitis," *J. Autoimmun. (Abs.)* 11:255-264, Academic Press (1998).

(Continued)

*Primary Examiner*—Phillip Gambel
*Assistant Examiner*—Sharon Wen
(74) *Attorney, Agent, or Firm*—Sterne, Kessler, Goldstein & Fox, P.L.L.C.

(57) ABSTRACT

The present invention is directed to recombinant human antibodies specific for Cn2 toxin from *C. noxius* scorpion venom. The antibodies are able to recognize the toxin and preferably neutralize it as well as the whole venom of *C. noxius* scorpion. This invention is also directed to a human non-immune phage display library. One clone that specifically binds the Cn2 toxin was affinity matured by directed evolution. Three cycles of maturation were performed and several scFv clones were isolated which specifically recognize toxin Cn2 with increased Kd of 446 fold. All variants were monomeric and only variants 6009F, 6105F and 6103E showed to be capable of neutralizing toxin Cn2 and the whole venom. Variant 6009F recognizes a different epitope than that of BCF2, a murine monoclonal antibody raised against scorpion toxin Cn2 which is also capable of neutralizing both Cn2 toxin and the whole venom when tested in mice, as well as that of commercially available polyclonal antibody fragments antivenom from horse. The scFv 6009F is the first reported recombinant human antibody fragment capable of neutralizing a scorpion venom. These results pave the way for the generation of safer autologous recombinant neutralizing antivenom against scorpion stings. The antibodies of the present invention can be used as part of a composition to treat those in need of treatment including those already stung by one or more scorpions, particularly *C. noxius* scorpions.

30 Claims, 11 Drawing Sheets

OTHER PUBLICATIONS

Figure 2:
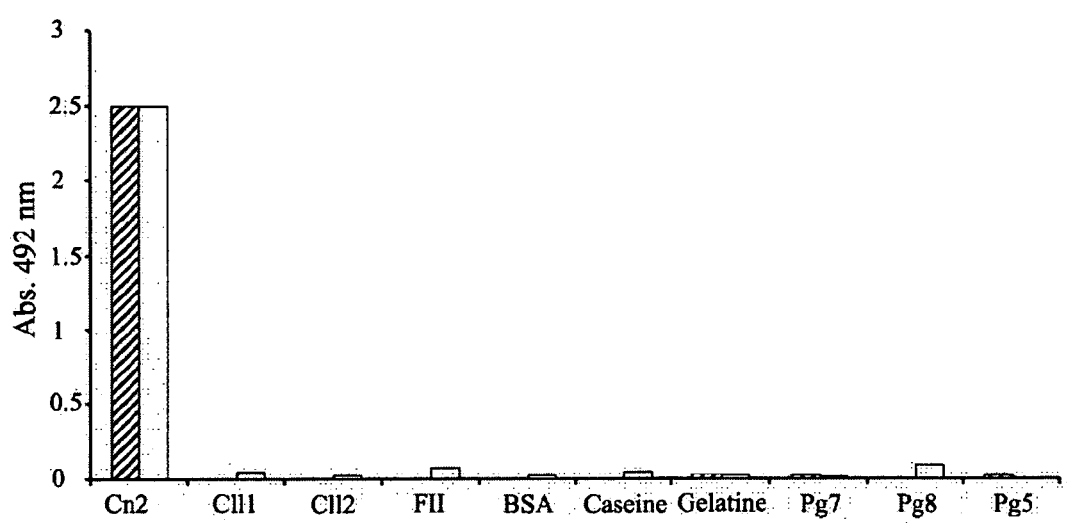

Edman, P. and Begg, G., "A Protein Sequenator," *Eur. J. Biochem.* *1*:80-91, Blackwell Science, Ltd. on behalf of the Federation of European Biochemical Societies (1967).

Fekade, D., et al., "Prevention of Jarisch-Herxheimer Reactions by Treatment with Antibodies Against Tumor Necrosis Factor α," *N. Engl. J. Med.* *335*:311-315, Massachusetts Medical Society (1996).

Fox, D.A., et al., "Cytokine Blockade as a New Strategy to Treat Rheumatoid Arthritis," *Arch. Intern. Med.* *160*:437-444, American Medical Association (Feb. 2000).

García, C., et al., "Isolation, Characterization and Comparison of Novel Crustacean Toxin with a Mammalian Toxin from the Venom of the Scorpion *Centruroides noxius* Hoffman," *Comp. Biochem. Physiol.* *116B*:315-322, Elsevier Science, Inc. (1997).

Krueger, J.G., "The immunologic basis for the treatment of psoriasis with new biologic agents," *J. Am. Acad. Dermatol.* *46*:1-23, American Academy of Dermatology, Inc. (Jan. 2002).

Legros, C., et al., "Use of fusion protein constructs to generate potent immunotherapy and protection against scorpion toxins," *Vaccine* *20*:934-942, Elsevier Science, Ltd. (2002).

Licea, A.F., et al., "FAB Fragments of the Monoclonal Antibody BCF2 are Capable of Neutralizing the Whole Venom from the Scorpion *Centruroides noxius* Hoffman," *Toxicon* *34*:843-847, Elsevier Science Ltd. (1996).

Lisman, K.A., et al., "Managing Heart Failure with Immunomodulatory Agents," *Cardiol. Clin.* *19*:617-625, W.B. Saunders Co. (Nov. 2001).

Luger, T., "Treatment of immune-mediated skin diseases: future perspectives," *Eur. J. Dermatol.* *11*:343-347, John Libbey Eurotext (2001).

English translation of Maraboto Martinez, J.A., et al., "Panorama Epidemiológico de las Intoxicaciones Causadas por Animales Ponzoñosos en la Población Derechohabiente del IMSS 1990-1998," in *3ª Reunión de Expertos en Envenenamiento por Animales Ponzoñosos*, Instituto de Biotecnología, Universidad Nacional Autónoma de México, Alcapulco, Gro., México (Feb. 17-19, 1999).

Martin, G.S., "Current Management Strategies for Severe Sepsis and Septic Shock," Presented at Chest 2001: 67th Annual Scientific Assembly of the American College of Chest Physicians, Nov. 4-8, 2001, Philadelphia, PA.

Nonner, W., "Effects of *Leiurus* Scorpion Venom on the "Gating" Current in Myelinated Nerve," *Adv. Cytopharmacol.* *3*:345-352, Raven Press (1979).

Possani, L.D., et al., "Scorpion toxins from *Centruroides noxius* and *Tityus serrulatus*," *Biochem. J.* *229*:739-750, Biochemical Society/Portland Press (1985).

Possani, L.D., et al., "Scorpion toxins specific for $NA^+$-channels," *Eur. J. Biochem.* *264*:287-300, Blackwell Science, Ltd. on behalf of the Federation of European Biochemical Societies (1999).

Possani, L.D., et al., "Peptides and genes coding for scorpion toxins that affect ion-channels," *Biochimie* *82*:861-868, Editions Scientifiques Elsevier (2000).

Present, D.H., et al., "Infliximab for the Treatment of Fistulas in Patients with Crohn's Disease," *N. Engl. J. Med.* *340*:1398-1405, Massachusetts Medical Society (1999).

Qian, Y., et al., "Topical Soluble Tumor Necrosis Factor Receptor Type I Suppresses Ocular Chemokine Gene Expression and Rejection of Allogenic Corneal Transplants," *Arch. Ophthalmol.* *118*:1666-1671, American Medical Association (2000).

Stapcynski, J.S., "Shock, Septic," accessed at http://emedicine.com/EMERG/topic533.htm, eMedicine.com Inc., 25 pages (2004).

Strichartz, G., et al., "An Integrated View of the Molecular Toxinology of Sodium Channel Gating in Excitable Cells," *Ann. Rev. Neurosci.* *10*:237-267, Annual Reviews, Inc. (1987).

Torres, P.F., and Kijlstra, A., "The role of cytokines in corneal immunopathology," *Ocul. Immunol. Inflamm.* *9*:9-24, Swets & Zeitlinger (2001).

Zamudio, F., et al., "Amino acid sequence and immunological characterization with monoclonal antibodies of two toxins from the venom of the scorpion *Centruroides noxius* Hoffman," *Eur. J. Biochem.* *204*:281-292, Blackwell Science, Ltd. on behalf of the Federation of European Biochemical Societies (1992).

Zhu, S., et al., "Early Expression of Proinflammatory Cytokines Interleukin-1 and Tumor Necrosis Factor-α after Corneal Transplantation," *J. Interferon Cytokine Res.* *19*:661-669, Mary Ann Liebert, Inc. (1999).

English translation of Secretaría de Salud, "Potency of Anti-Poison Sera," in *Farmacopea de los Estados Unidos Mexicanos*, vol. II, Secretaría de Salud, Mexico City, MX, pp. 1756-1757 (2000).

English language translation of Secretarí de Salud, "Pyrogen Tests," in *Farmacopea de los Estados Unidos Mexicanos*, vol. I, Secretaría de Salud, Mexico City, MX, pp. 334-335 (2000).

International Search Report for International Patent Application No. PCT/MX02/0013, European Patent Office, Netherlands, mailed Aug. 16, 2002.

Dialog File 351, Accession No. 9271133, English language abstract for Spanish Patent No. 2 106 183, 2004.

FIGURE 1

```
                                         CDR H1
C1   1   QVNLRESGGGLVQPGGSLRLSCAAS GFSFGSYG MHWVRQA   40
3F   1   EVQLVESGGGLVQPGGSLRLSCAGS GFTFDNYA MHWIRQV   40

CDR H2
C1  41   PGKGLEWVAV ISYDGSNK YYADSVKGRFTISRDNSKNTLY   80
3F  41   PGEGLEWVSG ISRSSGDI GYADSVKGRFTISRDNAKKSLS   80

CDR H3
C1  81   LQMNSLRAEDTAVYYC AKDARDCLMCADWYFDL WGRGTLV  120
3F  81   LQMNSLRAEDTAVYYC AR-G-G----VGS-FDT WGQGTMV  113

Linker
C1 121   TVSSGGGGSGGGGSGGGGSNFMLTQ-PHSASGTPGQRVTI   159
3F 114   TVSSGGGGSGGGGSGGGGSEIVLTQSPATLSVSPGERATL   153

CDR L1                         CDR L2
C1 160   SCSGS SSNIGSNT VNWYRHLPGSAPELLIG SHNQ RPSGVP  199
3F 154   SCRAS QS--VRSY LAWYQQKPGQAPRLLIS DASN RATGIP  191

CDR L3
C1 200   DRFSASKSDTSASLAISGLQSEDEADYYC AAWDDSLIGYV  239
3F 192   ARFTGSGSGTDFTLTISSLEPEDFAIYYC QQY--RYSPRT  229

C1 240   FGTGTKLTVLGAAAEQKLISEEDLNGAAHHHHHH  273
3F 230   FGQGTKVEIKRAAAEQKLISEEDLNGAAHHHHHH  263
```

FIGURE 4
A
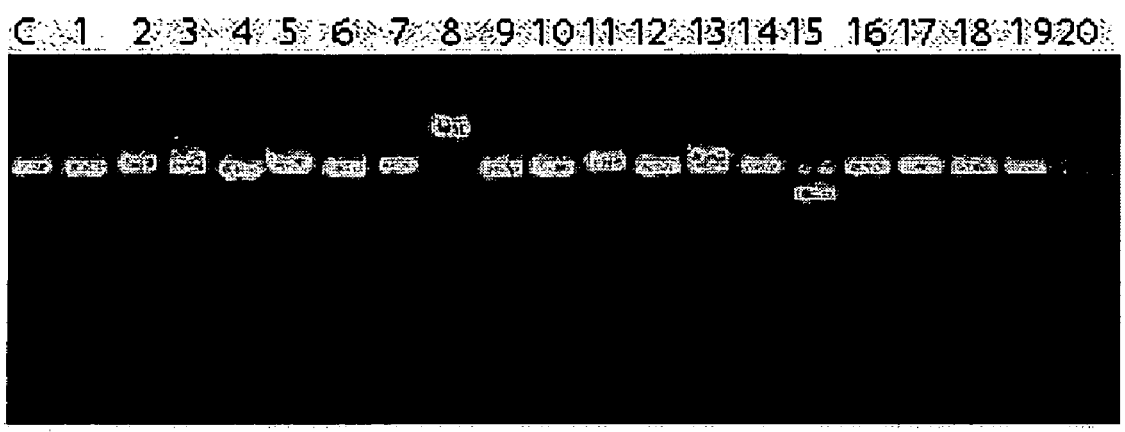
B

SEQUENCE LISTING

<160> NUMBER OF SEQ ID NOS: 97

<210> SEQ ID NO 1
<211> LENGTH: 62
<212> TYPE: DNA
<213> ORGANISM: Artificial
<220> FEATURE:
<223> OTHER INFORMATION: Oligonucleotide for Kappa1a family
<220> FEATURE:
<221> NAME/KEY: primer_bind
<222> LOCATION: (1)..(62)

<400> SEQUENCE: 1
ggcggatcag gaggcggagg ttctggtgga ggtgggagtg acatccagat gacccagtct    60
cc                                                                   62

<210> SEQ ID NO 2
<211> LENGTH: 62
<212> TYPE: DNA
<213> ORGANISM: Artificial
<220> FEATURE:
<223> OTHER INFORMATION: Oligonucleotide for Kappa2 family
<220> FEATURE:
<221> NAME/KEY: primer_bind
<222> LOCATION: (1)..(62)

<400> SEQUENCE: 2
ggcggatcag gaggcggagg ttctggtgga ggtgggagtg atgttgtgat gactcagtct    60
cc                                                                   62

<210> SEQ ID NO 3
<211> LENGTH: 62
<212> TYPE: DNA
<213> ORGANISM: Artificial
<220> FEATURE:
<223> OTHER INFORMATION: Oligonucleotide for Kappa3 family
<220> FEATURE:
<221> NAME/KEY: primer_bind
<222> LOCATION: (1)..(62)

<400> SEQUENCE: 3
ggcggatcag gaggcggagg ttctggtgga ggtgggagtg aaattgtgtt gacgcagtct    60
cc                                                                   62

<210> SEQ ID NO 4
<211> LENGTH: 62
<212> TYPE: DNA
<213> ORGANISM: Artificial
<220> FEATURE:
<223> OTHER INFORMATION: Oligonucleotide for Kappa4 family
<220> FEATURE:
<221> NAME/KEY: primer_bind
<222> LOCATION: (1)..(62)

<400> SEQUENCE: 4
ggcggatcag gaggcggagg ttctggtgga ggtgggagtg acatcgtgat gacccagtct    60
cc                                                                   62

<210> SEQ ID NO 5
<211> LENGTH: 62
<212> TYPE: DNA
<213> ORGANISM: Artificial
<220> FEATURE:
<223> OTHER INFORMATION: Oligonucleotide for Kappa5 family

```
<220> FEATURE:
<221> NAME/KEY: primer_bind
<222> LOCATION: (1)..(62)

<400> SEQUENCE: 5
ggcggatcag gaggcggagg ttctggtgga ggtgggagtg aaacgacact cacgcagtct    60
cc                                                                   62

<210> SEQ ID NO 6
<211> LENGTH: 62
<212> TYPE: DNA
<213> ORGANISM: Artificial
<220> FEATURE:
<223> OTHER INFORMATION: Oligonucleotide for Kappa6 family
<220> FEATURE:
<221> NAME/KEY: primer_bind
<222> LOCATION: (1)..(62)

<400> SEQUENCE: 6
ggcggatcag gaggcggagg ttctggtgga ggtgggagtg aaattgtgct gactcagtct    60
cc                                                                   62

<210> SEQ ID NO 7
<211> LENGTH: 62
<212> TYPE: DNA
<213> ORGANISM: Artificial
<220> FEATURE:
<223> OTHER INFORMATION: Oligonucleotide for Lamba1 family
<220> FEATURE:
<221> NAME/KEY: primer_bind
<222> LOCATION: (1)..(62)

<400> SEQUENCE: 7
ggcggatcag gaggcggagg ttctggtgga ggtgggagtc agctcgtgtt gacgcagccg    60
cc                                                                   62

<210> SEQ ID NO 8
<211> LENGTH: 62
<212> TYPE: DNA
<213> ORGANISM: Artificial
<220> FEATURE:
<223> OTHER INFORMATION: Oligonucleotide for Lambda2 family
<220> FEATURE:
<221> NAME/KEY: primer_bind
<222> LOCATION: (1)..(62)

<400> SEQUENCE: 8
ggcggatcag gaggcggagg ttctggtgga ggtgggagtc agtctgccct gactcagcct    60
gc                                                                   62

<210> SEQ ID NO 9
<211> LENGTH: 62
<212> TYPE: DNA
<213> ORGANISM: Artificial
<220> FEATURE:
<223> OTHER INFORMATION: Oligonucleotide for Lambda3b family
<220> FEATURE:
<221> NAME/KEY: primer_bind
<222> LOCATION: (1)..(62)

<400> SEQUENCE: 9
ggcggatcag gaggcggagg ttctggtgga ggtgggagtt cttctgagct gactcaggac    60
cc                                                                   62
```

```
<210> SEQ ID NO 10
<211> LENGTH: 62
<212> TYPE: DNA
<213> ORGANISM: Artificial
<220> FEATURE:
<223> OTHER INFORMATION: Oligonucleotide for Lambda3a family
<220> FEATURE:
<221> NAME/KEY: primer_bind
<222> LOCATION: (1)..(62)

<400> SEQUENCE: 10
ggcggatcag gaggcggagg ttctggtgga ggtgggagtt cctatgtgct gactcagcca      60
cc                                                                    62

<210> SEQ ID NO 11
<211> LENGTH: 62
<212> TYPE: DNA
<213> ORGANISM: Artificial
<220> FEATURE:
<223> OTHER INFORMATION: Oligonucleotide for Lambda4 family
<220> FEATURE:
<221> NAME/KEY: primer_bind
<222> LOCATION: (1)..(62)

<400> SEQUENCE: 11
ggcggatcag gaggcggagg ttctggtgga ggtgggagtc acgttatact gactcaaccg      60
cc                                                                    62

<210> SEQ ID NO 12
<211> LENGTH: 62
<212> TYPE: DNA
<213> ORGANISM: Artificial
<220> FEATURE:
<223> OTHER INFORMATION: Oligonucleotide for Lambda5 family
<220> FEATURE:
<221> NAME/KEY: primer_bind
<222> LOCATION: (1)..(62)

<400> SEQUENCE: 12
ggcggatcag gaggcggagg ttctggtgga ggtgggagtc aggctgtgct cactcagccg      60
tc                                                                    62

<210> SEQ ID NO 13
<211> LENGTH: 62
<212> TYPE: DNA
<213> ORGANISM: Artificial
<220> FEATURE:
<223> OTHER INFORMATION: Oligonucleotide for Lambda6 family
<220> FEATURE:
<221> NAME/KEY: primer_bind
<222> LOCATION: (1)..(62)

<400> SEQUENCE: 13
ggcggatcag gaggcggagg ttctggtgga ggtgggagta attttatgct gactcagccc      60
ca                                                                    62

<210> SEQ ID NO 14
<211> LENGTH: 59
<212> TYPE: DNA
<213> ORGANISM: Artificial
<220> FEATURE:
<223> OTHER INFORMATION: Oligonucleotide for JH1-2 families
<220> FEATURE:
<221> NAME/KEY: primer_bind
<222> LOCATION: (1)..(59)

<400> SEQUENCE: 14
```
ccaccagaac ctccgcctcc tgatccgcca cctcctgagg agacggtgac cagggtgcc    59

<210> SEQ ID NO 15
<211> LENGTH: 59
<212> TYPE: DNA
<213> ORGANISM: Artificial
<220> FEATURE:
<223> OTHER INFORMATION: Oligonucleotide for JH-3 family
<220> FEATURE:
<221> NAME/KEY: primer_bind
<222> LOCATION: (1)..(59)

<400> SEQUENCE: 15
ccaccagaac ctccgcctcc tgatccgcca cctcctgaag agacggtgac cattgtccc    59

<210> SEQ ID NO 16
<211> LENGTH: 59
<212> TYPE: DNA
<213> ORGANISM: Artificial
<220> FEATURE:
<223> OTHER INFORMATION: Oligonucleotide for JH4-5 family
<220> FE

```
ctg caa atg aac agc ctg aga gct gag gac acg gct gtg tat tac tgt      288
Leu Gln Met Asn Ser Leu Arg Ala Glu Asp Thr Ala Val Tyr Tyr Cys
             85                  90                  95 gcg aaa gat gcc cgc gat tgc cta atg tgc gcc gac tgg tac ttc gat      336
Ala Lys Asp Ala Arg Asp Cys Leu Met Cys Ala Asp Trp Tyr Phe Asp
            100                 105                 110 ctc tgg ggc cgt gga acc ctg gtc acc gtc tcc tca gga ggt ggc gga      384
Leu Trp Gly Arg Gly Thr Leu Val Thr Val Ser Ser Gly Gly Gly Gly
        115                 120                 125 tca gga ggc gga ggt tct ggt gga ggt ggg agt aat ttt atg ctg act      432
Ser Gly Gly Gly Gly Ser Gly Gly Gly Gly Ser Asn Phe Met Leu Thr
130                 135                 140 cag ccc cac tca gcg tct ggg acc ccc gga cag agg gtc acc atc tct      480
Gln Pro His Ser Ala Ser Gly Thr Pro Gly Gln Arg Val Thr Ile Ser
145                 150                 155                 160 tgt tct gga agc agc tcc aac atc gga agt aat act gta aac tgg tac      528
Cys Ser Gly Ser Ser Ser Asn Ile Gly Ser Asn Thr Val Asn Trp Tyr
                165                 170                 175 cgg cat ctc cca ggc tcg gcc ccc gaa ctc ctc atc ggt agt cat aat      576
Arg His Leu Pro Gly Ser Ala Pro Glu Leu Leu Ile Gly Ser His Asn
            180                 185                 190 cag cgg ccc tca ggg gtc cct gac cga ttc tct gcc tcc aag tct gac      624
Gln Arg Pro Ser Gly Val Pro Asp Arg Phe Ser Ala Ser Lys Ser Asp
        195                 200                 205 acc tca gcc tcc ctg gcc atc agt ggg ctc cag tct gag gat gag gct      672
Thr Ser Ala Ser Leu Ala Ile Ser Gly Leu Gln Ser Glu Asp Glu Ala
    210                 215                 220 gat tat tac tgt gca gca tgg gat gac agc ctg att ggt tat gtc ttc      720
Asp Tyr Tyr Cys Ala Ala Trp Asp Asp Ser Leu Ile Gly Tyr Val Phe
225                 230                 235                 240 gga act ggg acc aag ctg acc gtc cta ggt                              750
Gly Thr Gly Thr Lys Leu Thr Val Leu Gly
                245                 250

<210> SEQ ID NO 19
<211> LENGTH: 250
<212> TYPE: PRT
<213> ORGANISM: Homo sapiens

<400> SEQUENCE: 19

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Ser Phe Gly Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Arg Asp Cys Leu Met Cys Ala Asp Trp Tyr Phe Asp
            100                 105                 110

Leu Trp Gly Arg Gly Thr Leu Val Thr Val Ser Ser Gly Gly Gly Gly
        115                 120                 125

Ser Gly Gly Gly Gly Ser Gly Gly Gly Gly Ser Asn Phe Met Leu Thr
    130                 135                 140
```

```
Gln Pro His Ser Ala Ser Gly Thr Pro Gly Gln Arg Val Thr Ile Ser
145                 150                 155                 160

Cys Ser Gly Ser Ser Ser Asn Ile Gly Ser Asn Thr Val Asn Trp Tyr
                165                 170                 175

Arg His Leu Pro Gly Ser Ala Pro Glu Leu Leu Ile Gly Ser His Asn
            180                 185                 190

Gln Arg Pro Ser Gly Val Pro Asp Arg Phe Ser Ala Ser Lys Ser Asp
        195                 200                 205

Thr Ser Ala Ser Leu Ala Ile Ser Gly Leu Gln Ser Glu Asp Glu Ala
    210                 215                 220

Asp Tyr Tyr Cys Ala Ala Trp Asp Asp Ser Leu Ile Gly Tyr Val Phe
225                 230                 235                 240

Gly Thr Gly Thr Lys Leu Thr Val Leu Gly
                245                 250

<210> SEQ ID NO 20
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: Product= VH of scFv C1

<400> SEQUENCE: 20 cag gtc aac tta agg gag tct ggg gga ggc ttg gta cag cct ggg ggg      48
Gln Val Asn Leu Arg Glu Ser Gly Gly Gly Leu Val Gln Pro Gly Gly
1               5                   10                  15 tcc ctg aga ctc tcc tgt gca gcc tct gga ttc tcc ttt ggc agc tat      96
Ser Leu Arg Leu Ser Cys Ala Ala Ser Gly Phe Ser Phe Gly Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tca tat gat gga agt aat aaa tac tat gca gac tcc gtg     192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aaa gat gcc cgc gat tgc cta atg tgc gcc gac tgg tac ttc gat     336
Ala Lys Asp Ala Arg Asp Cys Leu Met Cys Ala Asp Trp Tyr Phe Asp
            100                 105                 110 ctc tgg ggc cgt gga acc ctg gtc acc gtc tcc tca                     372
Leu Trp Gly Arg Gly Thr Leu Val Thr Val Ser Ser
        115                 120

<210> SEQ ID NO 21
<211> LENGTH: 124
<212> TYPE: PRT
<213> ORGANISM: Homo sapiens

<400> SEQUENCE: 21

Gln Val Asn Leu Arg Glu Ser Gly Gly Gly Leu Val Gln Pro Gly Gly
1               5                   10                  15

Ser Leu Arg Leu Ser Cys Ala Ala Ser Gly Phe Ser Phe Gly Ser Tyr
            20                  25                  30
```

-continued

```
Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Arg Asp Cys Leu Met Cys Ala Asp Trp Tyr Phe Asp
            100                 105                 110

Leu Trp Gly Arg Gly Thr Leu Val Thr Val Ser Ser
        115                 120

<210> SEQ ID NO 22
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: Product= VL of scFv C1

<400> SEQUENCE: 22 aat ttt atg ctg act cag ccc cac tca gcg tct ggg acc ccc gga cag      48
Asn Phe Met Leu Thr Gln Pro His Ser Ala Ser Gly Thr Pro Gly Gln
 1               5                  10                  15 agg gtc acc atc tct tgt tct gga agc agc tcc aac atc gga agt aat      96
Arg Val Thr Ile Ser Cys Ser Gly Ser Ser Ser Asn Ile Gly Ser Asn
             20                  25                  30 act gta aac tgg tac cgg cat ctc cca ggc tcg gcc ccc gaa ctc ctc     144
Thr Val Asn Trp Tyr Arg His Leu Pro Gly Ser Ala Pro Glu Leu Leu
         35                  40                  45 atc ggt agt cat aat cag cgg ccc tca ggg gtc cct gac cga ttc tct     192
Ile Gly Ser His Asn Gln Arg Pro Ser Gly Val Pro Asp Arg Phe Ser
     50                  55                  60 gcc tcc aag tct gac acc tca gcc tcc ctg gcc atc agt ggg ctc cag     240
Ala Ser Lys Ser Asp Thr Ser Ala Ser Leu Ala Ile Ser Gly Leu Gln
 65                  70                  75                  80 tct gag gat gag gct gat tat tac tgt gca gca tgg gat gac agc ctg     288
Ser Glu Asp Glu Ala Asp Tyr Tyr Cys Ala Ala Trp Asp Asp Ser Leu
                 85                  90                  95 att ggt tat gtc ttc gga act ggg acc aag ctg acc gtc cta ggt          333
Ile Gly Tyr Val Phe Gly Thr Gly Thr Lys Leu Thr Val Leu Gly
            100                 105                 110

<210> SEQ ID NO 23
<211> LENGTH: 111
<212> TYPE: PRT
<213> ORGANISM: Homo sapiens

<400> SEQUENCE: 23

Asn Phe Met Leu Thr Gln Pro His Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Arg His Leu Pro Gly Ser Ala Pro Glu Leu Leu
         35                  40                  45

Ile Gly Ser His Asn Gln Arg Pro Ser Gly Val Pro Asp Arg Phe Ser
     50                  55                  60
```

-continued

```
Ala Ser Lys Ser Asp Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Ile Gly Tyr Val Phe Gly Thr Gly Thr Lys Leu Thr Val Leu Gly
            100                 105                 110

<210> SEQ ID NO 24
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 3F, specific for toxin Cn2

<400> SEQUENCE: 24 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
 1               5                  10                  15 tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg agc agt ggt gac ata ggc tat gcg gac tct gtg     192
Ser Gly Ile Ser Arg Ser Ser Gly Asp Ile Gly Tyr Ala Asp Ser Val
    50                  55                  60 aag ggc cga ttc acc atc tcc aga gac aac gcc aag aag tcc ctg tct     240
Lys Gly Arg Phe Thr Ile Ser Arg Asp Asn Ala Lys Lys Ser Leu Ser
 65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                 85                  90                  95 gcg aga ggg ggg gtc gga agt ttt gat acc tgg ggc caa ggg aca atg     336
Ala Arg Gly Gly Val Gly Ser Phe Asp Thr Trp Gly Gln Gly Thr Met
            100                 105                 110 gtc acc gtc tct tca gga ggt ggc gga tca gga ggc gga ggt tct ggt     384
Val Thr Val Ser Ser Gly Gly Gly Gly Ser Gly Gly Gly Gly Ser Gly
        115                 120                 125 gga ggt ggg agt gaa att gtg ctg act cag tct cca gcc acc ctg tct     432
Gly Gly Gly Ser Glu Ile Val Leu Thr Gln Ser Pro Ala Thr Leu Ser
    130                 135                 140 gtg tct ccc ggg gaa aga gcc acc ctc tcc tgc agg gcc agt cag agt     480
Val Ser Pro Gly Glu Arg Ala Thr Leu Ser Cys Arg Ala Ser Gln Ser
145                 150                 155                 160 gtt agg agc tac tta gcc tgg tac caa cag aaa cct ggc cag gct ccc     528
Val Arg Ser Tyr Leu Ala Trp Tyr Gln Gln Lys Pro Gly Gln Ala Pro
                165                 170                 175 agg ctc ctc atc tct gat gca tcc aac agg gcc act ggc atc cca gcc     576
Arg Leu Leu Ile Ser Asp Ala Ser Asn Arg Ala Thr Gly Ile Pro Ala
            180                 185                 190 agg ttc act ggc agt ggg tct ggg aca gac ttc act ctc acc atc agc     624
Arg Phe Thr Gly Ser Gly Ser Gly Thr Asp Phe Thr Leu Thr Ile Ser
        195                 200                 205 agc cta gag cct gaa gat ttt gca att tat tac tgt cag cag tat cgt     672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt     720
Tyr Ser Pro Arg Thr Phe Gly Gln Gly Thr Lys Val Glu Ile Lys Arg
```

-continued

```
                225                 230                 235                 240
```

<210> SEQ ID NO 25
<211> LENGTH: 240
<212> TYPE: PRT
<213> ORGANISM: Homo sapiens

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Ser Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Val Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240
```

<210> SEQ ID NO 26
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 3F

<400> SEQUENCE: 26

```
gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat       96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc      144
Ala Met His Trp Ile Arg Gln Val Pro Gly Glu Gly Leu Glu Trp Val
        35                  40                  45
```

```
tca ggt att agt cgg agc agt ggt gac ata ggc tat gcg gac tct gtg      192
Ser Gly Ile Ser Arg Ser Ser Gly Asp Ile Gly Tyr Ala Asp Ser Val
 50                  55                  60 aag ggc cga ttc acc atc tcc aga gac aac gcc aag aag tcc ctg tct      240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95 gcg aga ggg ggg gtc gga agt ttt gat acc tgg ggc caa ggg aca atg      336
Ala Arg Gly Gly Val Gly Ser Phe Asp Thr Trp Gly Gln Gly Thr Met
            100                 105                 110 gtc acc gtc tct tca                                                  351
Val Thr Val Ser Ser
        115

<210> SEQ ID NO 27
<211> LENGTH: 117
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Ser Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Val Gly Ser Phe Asp Thr Trp Gly Gln Gly Thr Met
            100                 105                 110

Val Thr Val Ser Ser
        115

<210> SEQ ID NO 28
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 3F

<400> SEQUENCE: 28 gaa att gtg ctg act cag tct cca gcc acc ctg tct gtg tct ccc ggg       48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac       96
Glu Arg Ala Thr Leu Ser Cys Arg Ala Ser Gln Ser Val Arg Ser Tyr
            20                  25                  30 tta gcc tgg tac caa cag aaa cct ggg cag gct ccc agg ctc ctc atc      144
Leu Ala Trp Tyr Gln Gln Lys Pro Gly Gln Ala Pro Arg Leu Leu Ile
        35                  40                  45 tct gat gca tcc aac agg gcc act ggc atc cca gcc agg ttc act ggc      192
Ser Asp Ala Ser Asn Arg Ala Thr Gly Ile Pro Ala Arg Phe Thr Gly
    50                  55                  60
```

```
agt ggg tct ggg aca gac ttc act ctc acc atc agc agc cta gag cct    240
Ser Gly Ser Gly Thr Asp Phe Thr Leu Thr Ile Ser Ser Leu Glu Pro
 65                  70                  75                  80 gaa gat ttt gca att tat tac tgt cag cag tat cgt tac tca cct cgg    288
Glu Asp Phe Ala Ile Tyr Tyr Cys Gln Gln Tyr Arg Tyr Ser Pro Arg
                 85                  90                  95 acg ttc ggc caa ggg acc aag gtg gag atc aaa cgt                    324
Thr Phe Gly Gln Gly Thr Lys Val Glu Ile Lys Arg
            100                 105

<210> SEQ ID NO 29
<211> LENGTH: 108
<212> TYPE: PRT
<213> ORGANISM: Homo sapiens

<400> SEQUENCE: 29

Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Arg Ser Tyr
                 20                  25                  30

Leu Ala Trp Tyr Gln Gln Lys Pro Gly Gln Ala Pro Arg Leu Leu Ile
             35                  40                  45

Ser Asp Ala Ser Asn Arg Ala Thr Gly Ile Pro Ala Arg Phe Thr Gly
 50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln Tyr Arg Tyr Ser Pro Arg
                 85                  90                  95

Thr Phe Gly Gln Gly Thr Lys Val Glu Ile Lys Arg
            100                 105

<210> SEQ ID NO 30
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6F, specific for toxin Cn2

<400> SEQUENCE: 30 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
  1               5                  10                  15 tcc ctg aga ctc tcc tgt gca ggc tct gga ttc acc ttt gat aat tat     96
Ser Leu Arg Leu Ser Cys Ala Gly Ser Gly Phe Thr Phe Asp Asn Tyr
                 20                  25                  30 gcc atg cat tgg ata cgc caa gtt cca ggg gag ggc ctg gag tgg gtc    144
Ala Met His Trp Ile Arg Gln Val Pro Gly Glu Gly Leu Glu Trp Val
             35                  40                  45 tca ggt att agt cgg ggc agt ggt gac ata ggc tat gcg gac tct gtg    192
Ser Gly Ile Ser Arg Gly Ser Gly Asp Ile Gly Tyr Ala Asp Ser Val
 50                  55                  60 aag ggc cga ttc acc atc tcc aga gac aac gcc aag aag tcc ctg tct    240
Lys Gly Arg Phe Thr Ile Ser Arg Asp Asn Ala Lys Lys Ser Leu Ser
 65                  70                  75                  80 ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                 85                  90                  95 gcg aga ggg ggg gtc gga agt ttt gat acc tgg ggc caa ggg aca atg    336
Ala Arg Gly Gly Val Gly Ser Phe Asp Thr Trp Gly Gln Gly Thr Met
```

-continued

```
gcc cgt ggt ggg gtt ggt tct ttt gac acc tgg ggc cag gga acc atg        
Ala Arg Gly Gly Val Gly Ser Phe Asp Thr Trp Gly Gln Gly Thr Met
            100                 105                 110 gtc acc gtc tct tca gga ggt ggc gga tca gga ggc gga ggt tct ggt        384
Val Thr Val Ser Ser Gly Gly Gly Gly Ser Gly Gly Gly Gly Ser Gly
            115                 120                 125 gga ggt ggg agt gaa att gtg ctg act cag tct cca gcc acc ctg tct        432
Gly Gly Gly Ser Glu Ile Val Leu Thr Gln Ser Pro Ala Thr Leu Ser
130                 135                 140 gtg tct ccc ggg gaa aga gcc acc ctc tcc tgc agg gcc agt cag agt        480
Val Ser Pro Gly Glu Arg Ala Thr Leu Ser Cys Arg Ala Ser Gln Ser
145                 150                 155                 160 gtt agg agc tac tta gcc tgg tac caa cag aaa cct ggg cag gct ccc        528
Val Arg Ser Tyr Leu Ala Trp Tyr Gln Gln Lys Pro Gly Gln Ala Pro
                165                 170                 175 agg ctc ctc atc tct gat gca tcc aac agg gcc act ggc atc cca gcc        576
Arg Leu Leu Ile Ser Asp Ala Ser Asn Arg Ala Thr Gly Ile Pro Ala
            180                 185                 190 agg ttc act ggc agt ggg tct ggg aca gac ttc act ctc acc atc agc        624
Arg Phe Thr Gly Ser Gly Ser Gly Thr Asp Phe Thr Leu Thr Ile Ser
            195                 200                 205 agc cta gag cct gaa gat ttt gca att tat tac tgt cag cag tat cgt        672
Ser Leu Glu Pro Glu Asp Phe Ala Ile Tyr Tyr Cys Gln Gln Tyr Arg
210                 215                 220 tac tca cct cgg acg ttc ggc caa ggg acc aag gtg gag atc aaa cgt        720
Tyr Ser Pro Arg Thr Phe Gly Gln Gly Thr Lys Val Glu Ile Lys Arg
225                 230                 235                 240
```

<210> SEQ ID NO 31
<211> LENGTH: 240
<212> TYPE: PRT
<213> ORGANISM: Homo sapiens

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Val Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190
```

```
Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240

<210> SEQ ID NO 32
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6F

<400> SEQUENCE: 32 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat     96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc    144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg    192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct    240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                85                  90                  95 gcg aga ggg ggg gtc gga agt ttt gat acc tgg ggc caa ggg aca atg    336
Ala Arg Gly Gly Val Gly Ser Phe Asp Thr Trp Gly Gln Gly Thr Met
            100                 105                 110 gtc acc gtc tct tca                                                 351
Val Thr Val Ser Ser
        115

<210> SEQ ID NO 33
<211> LENGTH: 117
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95
```

```
Ala Arg Gly Gly Val Gly Ser Phe Asp Thr Trp Gly Gln Gly Thr Met
            100                 105                 110
Val Thr Val Ser Ser
        115

<210> SEQ ID NO 34
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6F

<400> SEQUENCE: 34 gaa att gtg ctg act cag tct cca gcc acc ctg tct gtg tct ccc ggg       48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac       96
Glu Arg Ala Thr Leu Ser Cys Arg Ala Ser Gln Ser Val Arg Ser Tyr
                20                  25                  30 tta gcc tgg tac caa cag aaa cct ggg cag gct ccc agg ctc ctc atc      144
Leu Ala Trp Tyr Gln Gln Lys Pro Gly Gln Ala Pro Arg Leu Leu Ile
            35                  40                  45 tct gat gca tcc aac agg gcc act ggc atc cca gcc agg ttc act ggc      192
Ser Asp Ala Ser Asn Arg Ala Thr Gly Ile Pro Ala Arg Phe Thr Gly
    50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg      288
Glu Asp Phe Ala Ile Tyr Tyr Cys Gln Gln Tyr Arg Tyr Ser Pro Arg
                85                  90                  95 acg ttc ggc caa ggg acc aag gtg gag atc aaa cgt                      324
Thr Phe Gly Gln Gly Thr Lys Val Glu Ile Lys Arg
            100                 105

<210> SEQ ID NO 35
<211> LENGTH: 108
<212> TYPE: PRT
<213> ORGANISM: Homo sapiens

<400> SEQUENCE: 35

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
            100                 105

<210> SEQ ID NO 36
<211> LENGTH: 720
<212> TYPE: DNA
```

<210> ORGANISM: Homo sapiens
<220> FEATURE:
<221> NAME/KEY: CDS
<222> LOCATION: (1)..(720)
<223> OTHER INFORMATION: Product= scFv 610A, specific for toxin Cn2

<400> SEQUENCE: 36

```
gag gtg cag ctg gt

```
Ser Leu Arg Leu Ser Cys Ala Gly Ser Gly Phe Thr Phe Asp Asn Tyr
         20                  25                  30

Ala Met His Trp Ile Arg Gln Val Pro Gly Glu Gly Leu Glu Trp Val
         35                  40                  45

Ser Gly Ile Ser Arg Gly Ser Gly Asp Ile Gly Tyr Ala Asp Ser Val
 50                  55                  60

Lys Gly Arg Phe Thr Ile Ser Arg Asp Asn Ala Lys Lys Ser Leu Ser
65                   70                  75                  80

Leu Gln Met Asn Ser Leu Arg Ala Glu Asp Thr Ala Val Tyr Tyr Cys
                 85                  90                  95

Ala Arg Gly Gly Phe Gly Ser Phe Asp Thr Trp Gly Gln Gly Thr Met
             100                 105                 110

Val Thr Val Ser Ser Gly Gly Gly Ser Gly Gly Gly Gly Ser Gly
             115                 120                 125

Gly Gly Gly Ser Glu Ile Val Leu Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
             165                 170                 175

Arg Leu Leu Ile Ser Asp Ala Ser Asn Arg Ala Thr Gly Ile Pro Ala
             180                 185                 190

Arg Phe Thr Gly Ser Gly Ser Gly Thr Asp Phe Thr Leu Thr Ile Ser
             195                 200                 205

Ser Leu Glu Pro Glu Asp Phe Ala Ile Tyr Tyr Cys Gln Gln Tyr Arg
         210                 215                 220

Tyr Ser Pro Arg Thr Phe Gly Gln Gly Thr Lys Val Glu Ile Lys Arg
225                 230                 235                 240

<210> SEQ ID NO 38
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 610A

<400> SEQUENCE: 38 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat    96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc   144
Ala Met His Trp Ile Arg Gln Val Pro Gly Glu Gly Leu Glu Trp Val
         35                  40                  45 tca ggt att agt cgg ggc agt ggt gac ata ggc tat gcg gac tct gtg   192
Ser Gly Ile Ser Arg Gly Ser Gly Asp Ile Gly Tyr Ala Asp Ser Val
 50                  55                  60 aag ggc cga ttc acc atc tcc aga gac aac gcc aag aag tcc ctg tct   240
Lys Gly Arg Phe Thr Ile Ser Arg Asp Asn Ala Lys Lys Ser Leu Ser
65                   70                  75                  80 ctg caa atg aac agc ctg aga gcc gag gac acg gcc gtg tat tac tgt   288
Leu Gln Met Asn Ser Leu Arg Ala Glu Asp Thr Ala Val Tyr Tyr Cys
                 85                  90                  95 gcg aga ggg ggg ttc gga agt ttt gat acc tgg ggc caa ggg aca atg   336
```

```
Ala Arg Gly Gly Phe Gly Ser Phe Asp Thr Trp Gly Gln Gly Thr Met
            100                 105                 110 gtc acc gtc tct tca                                                    351
Val Thr Val Ser Ser
        115

<210> SEQ ID NO 39
<211> LENGTH: 117
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115

<210> SEQ ID NO 40
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 610A

<400> SEQUENCE: 40 gaa att gtg ctg act cag tct cca gcc acc ctg tct gtg tct ccc ggg       48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac       96
Glu Arg Ala Thr Leu Ser Cys Arg Ala Ser Gln Ser Val Arg Ser Tyr
            20                  25                  30 tta gcc tgg tac caa cag aaa cct ggg cag gct ccc agg ctc ctc atc      144
Leu Ala Trp Tyr Gln Gln Lys Pro Gly Gln Ala Pro Arg Leu Leu Ile
        35                  40                  45 tct gat gca tcc aac agg gcc act ggc atc cca gcc agg ttc act ggc      192
Ser Asp Ala Ser Asn Arg Ala Thr Gly Ile Pro Ala Arg Phe Thr Gly
    50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg      288
Glu Asp Phe Ala Ile Tyr Tyr Cys Gln Gln Tyr Arg Tyr Ser Pro Arg
                85                  90                  95 acg ttc ggc caa ggg acc aag gtg gag atc aaa cgt                      324
Thr Phe Gly Gln Gly Thr Lys Val Glu Ile Lys Arg
            100                 105
```

<210> SEQ ID NO 41
<211> LENGTH: 108
<212> TYPE: PRT
<213> ORGANISM: Homo sapiens

<400> SEQUENCE: 41

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
            100                 105
```

<210> SEQ ID NO 42
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6009, specific for toxin Cn2

<400> SEQUENCE: 42

```
gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat        96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc       144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg       192
Ser Gly Ile Ser Arg Gly Ser Gly Asp Ile Gly Tyr Ala Asp Ser Val
    50                  55                  60 aag ggc cga ttc acc atc tcc aga gac gac gcc aag aag tcc ctg tct       240
Lys Gly Arg Phe Thr Ile Ser Arg Asp Asp Ala Lys Lys Ser Leu Ser
65                  70                  75                  80 ctg caa atg aac agc ctg aga gcc gag gac acg gcc gtg tat tac tgt       288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg       336
Ala Arg Gly Gly Phe Gly Ser Phe Asp Thr Trp Gly Gln Gly Thr Met
            100                 105                 110 gtc acc gtc tct tct gga ggt ggc gga tca gga ggc gga ggt tct ggt       384
Val Thr Val Ser Ser Gly Gly Gly Gly Ser Gly Gly Gly Gly Ser Gly
        115                 120                 125 gga ggt ggg agt gaa att gtg ctg act cag tct cct gcc acc ctg tct       432
Gly Gly Gly Ser Glu Ile Val Leu Thr Gln Ser Pro Ala Thr Leu Ser
    130                 135                 140 gtg tct ccc ggg gaa aga gcc atc ctc tcc tgc agg gcc agt cag agt       480
Val Ser Pro Gly Glu Arg Ala Ile Leu Ser Cys Arg Ala Ser Gln Ser
```

```
                    145                 150                 155                 160
gtt agg agc ttc tta gcc tgg tac caa cag aaa cct ggg cag gct ccc            528
Val Arg Ser Phe Leu Ala Trp Tyr Gln Gln Lys Pro Gly Gln Ala Pro
                165                 170                 175 agg ctc ctc atc tct gat gca tcc aac agg gcc act ggc atc cca gcc            576
Arg Leu Leu Ile Ser Asp Ala Ser Asn Arg Ala Thr Gly Ile Pro Ala
            180                 185                 190 agg ttc act ggc ggt ggg tct ggg aca gac ttc act ctc acc atc agc            624
Arg Phe Thr Gly Gly Gly Ser Gly Thr Asp Phe Thr Leu Thr Ile Ser
            195                 200                 205 agc cta gag cct gaa gat ttt gca att tat tac tgt cag cag tat cgt            672
Ser Leu Glu Pro Glu Asp Phe Ala Ile Tyr Tyr Cys Gln Gln Tyr Arg
        210                 215                 220 tac tca cct cgg acg ttc ggc caa ggg acc aag gtg gag atc aaa cgt            720
Tyr Ser Pro Arg Thr Phe Gly Gln Gly Thr Lys Val Glu Ile Lys Arg
225                 230                 235                 240
```

<210> SEQ ID NO 43
<211> LENGTH: 240
<212> TYPE: PRT
<213> ORGANISM: Homo sapiens

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asp Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Ile Leu Ser Cys Arg Ala Ser Gln Ser
145                 150                 155                 160

Val Arg Ser Phe Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Gly Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240
```

<210> SEQ ID NO 44
<211> LENGTH: 351
<212> TYPE: DNA

<213> ORGANISM: Homo sapiens
<220> FEATURE:
<221> NAME/KEY: CDS
<222> LOCATION: (1)..(351)
<223> OTHER INFORMATION: Product= VH of scFv 6009F

<400> SEQUENCE: 44

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
    50                  55                  60 aag ggc cga ttc acc atc tcc aga gac gac gcc aag aag tcc ctg tct     240
Lys Gly Arg Phe Thr Ile Ser Arg Asp Asp Ala Lys Lys Ser Leu Ser
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110 gtc acc gtc tct tct                                                  351
Val Thr Val Ser Ser
        115
```

<210> SEQ ID NO 45
<211> LENGTH: 117
<212> TYPE: PRT
<213> ORGANISM: Homo sapiens

<400> SEQUENCE: 45

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asp Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115
```

<210> SEQ ID NO 46
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6009F

<400> SEQUENCE: 46

| | | | | | | | | | | | | | | | | |
|---|---|---|---|---|---|---|---|---|---|---|---|---|---|---|---|---|
| gaa | att | gtg | ctg | act | cag | tct | cct | gcc | acc | ctg | tct | gtg | tct | ccc | ggg | 48 |
| Glu | Ile | Val | Leu | Thr | Gln | Ser | Pro | Ala | Thr | Leu | Ser | Val | Ser | Pro | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gaa | aga | gcc | atc | ctc | tcc | tgc | agg | gcc | agt | cag | agt | gtt | agg | agc | ttc | 96 |
| Glu | Arg | Ala | Ile | Leu | Ser | Cys | Arg | Ala | Ser | Gln | Ser | Val | Arg | Ser | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| tta | gcc | tgg | tac | caa | cag | aaa | cct | ggg | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
| | | | 35 | | | | | 40 | | | | | 45 | | | |

| | | | | | | | | | | | | | | | | |
|---|---|---|---|---|---|---|---|---|---|---|---|---|---|---|---|---|
| tct | gat | gca | tcc | aac | agg | gcc | act | ggc | atc | cca | gcc | agg | ttc | act | ggc | 192 |
| Ser | Asp | Ala | Ser | Asn | Arg | Ala | Thr | Gly | Ile | Pro | Ala | Arg | Phe | Thr | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| ggt | ggg | tct | ggg | aca | gac | ttc | act | ctc | acc | atc | agc | agc | cta | gag | cct | 240 |
| Gly | Gly | Ser | Gly | Thr | Asp | Phe | Thr | Leu | Thr | Ile | Ser | Ser | Leu | Glu | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gaa | gat | ttt | gca | att | tat | tac | tgt | cag | cag | tat | cgt | tac | tca | cct | cgg | 288 |
| Glu | Asp | Phe | Ala | Ile | Tyr | Tyr | Cys | Gln | Gln | Tyr | Arg | Tyr | Ser | Pro | Arg | |
| | | | | 85 | | | | | 90 | | | | | 95 | | |

| | | | | | | | | | | | |
|---|---|---|---|---|---|---|---|---|---|---|---|
| acg | ttc | ggc | caa | ggg | acc | aag | gtg | gag | atc | aaa | cgt | 324 |
| Thr | Phe | Gly | Gln | Gly | Thr | Lys | Val | Glu | Ile | Lys | Arg | |
| | | | 100 | | | | | 105 | | | | |

<210> SEQ ID NO 47
<211> LENGTH: 108
<212> TYPE: PRT
<213> ORGANISM: Homo sapiens

<400> SEQUENCE: 47

Glu Ile Val Leu Thr Gln Ser Pro Ala Thr Leu Ser Val Ser Pro Gly
1               5                   10                  15

Glu Arg Ala Ile Leu Ser Cys Arg Ala Ser Gln Ser Val Arg Ser Phe
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Ala Arg Phe Thr Gly
    50                  55                  60

Gly Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
            100                 105

<210> SEQ ID NO 48
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6D, specific for toxin Cn2

<400> SEQUENCE: 48

| | | | | | | | | | | | | | | | | |
|---|---|---|---|---|---|---|---|---|---|---|---|---|---|---|---|---|
| gag | gtg | cag | ctg | gtg | gag | tct | ggg | gga | ggc | ttg | gta | cag | cct | ggg | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aga | ctc | tcc | tgt | gca | ggc | tct | gga | ttc | acc | ttt | gat | aat | tat | 96 |

| | | |
|---|---|---|
| Ser Leu Arg Leu Ser Cys Ala Gly Ser Gly Phe Thr Phe Asp Asn Tyr<br>            20                          25                          30 | |
| gcc atg cat tgg ata cgc caa gtt cca ggg gag ggc tgg gag tgg gtc<br>Ala Met His Trp Ile Arg Gln Val Pro Gly Glu Gly Leu Glu Trp Val<br>            35                          40                          45 | 144 |
| tca ggt att agt cgg ggc agt ggt gac ata ggc tat gcg gac tct gtg<br>Ser Gly Ile Ser Arg Gly Ser Gly Asp Ile Gly Tyr Ala Asp Ser Val<br>  50                        55                          60 | 192 |
| aag ggc cga ttc acc atc tcc aga gac aac gcc aag aag tcc ctg tct<br>Lys Gly Arg Phe Thr Ile Ser Arg Asp Asn Ala Lys Lys Ser Leu Ser<br>65                      70                        75                          80 | 240 |
| ctg caa atg aac agc ctg aga gcc gag gac acg gcc gtg tat tac tgt<br>Leu Gln Met Asn Ser Leu Arg Ala Glu Asp Thr Ala Val Tyr Tyr Cys<br>                      85                          90                          95 | 288 |
| gcg aga ggg ggg ttc gga agt ttt gat acc tgg ggc caa ggg aca atg<br>Ala Arg Gly Gly Phe Gly Ser Phe Asp Thr Trp Gly Gln Gly Thr Met<br>                100                        105                        110 | 336 |
| gtc acc gtc tct tca gga ggt ggc gga tca ggc gga ggt tct ggt<br>Val Thr Val Ser Ser Gly Gly Gly Gly Ser Gly Gly Gly Gly Ser Gly<br>            115                        120                        125 | 384 |
| gga ggt ggg agt gaa att gtg ctg act cag tct cca gcc acc ctg tct<br>Gly Gly Gly Ser Glu Ile Val Leu Thr Gln Ser Pro Ala Thr Leu Ser<br>130                     135                        140 | 432 |
| gtg tct ccc ggg gaa aga gcc acc ctc tcc tgc agg gcc agt cag agt<br>Val Ser Pro Gly Glu Arg Ala Thr Leu Ser Cys Arg Ala Ser Gln Ser<br>145                     150                        155                        160 | 480 |
| gtt agg agc tac tta gcc tgg tac caa cag aaa cct ggg cag gct ccc<br>Val Arg Ser Tyr Leu Ala Trp Tyr Gln Gln Lys Pro Gly Gln Ala Pro<br>                165                        170                        175 | 528 |
| agg ctc ctc atc tct gaa gca tcc aac agg gcc act ggc atc cca gcc<br>Arg Leu Leu Ile Ser Glu Ala Ser Asn Arg Ala Thr Gly Ile Pro Ala<br>                  180                        185                        190 | 576 |
| agg ttc act ggc agt ggg tct ggg aca gac ttc act ctc acc atc agc<br>Arg Phe Thr Gly Ser Gly Ser Gly Thr Asp Phe Thr Leu Thr Ile Ser<br>                195                        200                        205 | 624 |
| agc cta gag cct gaa gat ttt gca att tat tac tgt cag cag tat cgt<br>Ser Leu Glu Pro Glu Asp Phe Ala Ile Tyr Tyr Cys Gln Gln Tyr Arg<br>210                     215                        220 | 672 |
| tac tca cct cgg acg ttc ggc caa ggg acc aag gtg gag atc aaa cgt<br>Tyr Ser Pro Arg Thr Phe Gly Gln Gly Thr Lys Val Glu Ile Lys Arg<br>225                     230                        235                        240 | 720 |

```
<210> SEQ ID NO 49
<211> LENGTH: 240
<212> TYPE: PRT
<213> ORGANISM: Homo sapiens

<400> SEQUENCE: 49
```

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys

-continued

```
                             85                  90                  95
Ala Arg Gly Gly Phe Gly Ser Phe Asp Thr Trp Gly Gln Gly Thr Met
            100                 105                 110

Val Thr Val Ser Ser Gly Gly Gly Ser Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Glu Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240
```

<210> SEQ ID NO 50
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6D

<400> SEQUENCE: 50

```
gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat     96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc    144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg    192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct    240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg    336
Ala Arg Gly Gly Phe Gly Ser Phe Asp Thr Trp Gly Gln Gly Thr Met
            100                 105                 110 gtc acc gtc tct tca                                                 351
Val Thr Val Ser Ser
        115
```

<210> SEQ ID NO 51
<211> LENGTH: 117
<212> TYPE: PRT
<213> ORGANISM: Homo sapiens

```
<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
            115

<210> SEQ ID NO 52
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: Product= VL of scFv 6D

<400> SEQUENCE: 52 agt gaa att gtg ctg act cag tct cca gcc acc ctg tct gtg tct ccc         48
Ser Glu Ile Val Leu Thr Gln Ser Pro Ala Thr Leu Ser Val Ser Pro
1               5                   10                  15 ggg gaa aga gcc acc ctc tcc tgc agg gcc agt cag agt gtt agg agc         96
Gly Glu Arg Ala Thr Leu Ser Cys Arg Ala Ser Gln Ser Val Arg Ser
            20                  25                  30 tac tta gcc tgg tac caa cag aaa cct ggg cag gct ccc agg ctc ctc        144
Tyr Leu Ala Trp Tyr Gln Gln Lys Pro Gly Gln Ala Pro Arg Leu Leu
        35                  40                  45 atc tct gaa gca tcc aac agg gcc act ggc atc cca gcc agg ttc act        192
Ile Ser Glu Ala Ser Asn Arg Ala Thr Gly Ile Pro Ala Arg Phe Thr
    50                  55                  60 ggc agt ggg tct ggg aca gac ttc act ctc acc atc agc agc cta gag        240
Gly Ser Gly Ser Gly Thr Asp Phe Thr Leu Thr Ile Ser Ser Leu Glu
65                  70                  75                  80 cct gaa gat ttt gca att tat tac tgt cag cag tat cgt tac tca cct        288
Pro Glu Asp Phe Ala Ile Tyr Tyr Cys Gln Gln Tyr Arg Tyr Ser Pro
                85                  90                  95 cgg acg ttc ggc caa ggg acc aag gtg gag atc aaa cgt                    327
Arg Thr Phe Gly Gln Gly Thr Lys Val Glu Ile Lys Arg
            100                 105

<210> SEQ ID NO 53
<211> LENGTH: 109
<212> TYPE: PRT
<213> ORGANISM: Homo sapiens

<400> SEQUENCE: 53

Ser Glu Ile Val Leu Thr Gln Ser Pro Ala Thr Leu Ser Val Ser Pro
1               5                   10                  15

Gly Glu Arg Ala Thr Leu Ser Cys Arg Ala Ser Gln Ser Val Arg Ser
            20                  25                  30
```

Tyr Leu Ala Trp Tyr Gln Gln Lys Pro Gly Gln Ala Pro Arg Leu Leu
                35                  40                  45

Ile Ser Glu Ala Ser Asn Arg Ala Thr Gly Ile Pro Ala Arg Phe Thr
     50                  55                  60

Gly Ser Gly Ser Gly Thr Asp Phe Thr Leu Thr Ile Ser Ser Leu Glu
65                  70                  75                  80

Pro Glu Asp Phe Ala Ile Tyr Tyr Cys Gln Gln Tyr Arg Tyr Ser Pro
                 85                  90                  95

Arg Thr Phe Gly Gln Gly Thr Lys Val Glu Ile Lys Arg
            100                 105

<210> SEQ ID NO 54
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 9C, specific for toxin Cn2

<400> SEQUENCE: 54

| | | |
|---|---|---|
| gag gtg cag ctg gtg gag tct ggg gga ggc ttg gta cag cct ggg ggg<br>Glu Val Gln Leu Val Glu Ser Gly Gly Gly Leu Val Gln Pro Gly Gly<br>1               5                   10                  15 | 48 |
| tcc ctg aga ctc tcc tgt gca ggc tct gga ttc acc ttt gat aat tat<br>Ser Leu Arg Leu Ser Cys Ala Gly Ser Gly Phe Thr Phe Asp Asn Tyr<br>            20                  25                  30 | 96 |
| gcc atg cat tgg ata cgc caa gtt cca ggg gag ggc ctg gag tgg gtc<br>Ala Met His Trp Ile Arg Gln Val Pro Gly Glu Gly Leu Glu Trp Val<br>        35                  40                  45 | 144 |
| tca ggt att agt cgg ggc agt ggt gac ata ggc tat gcg gac tct gtg<br>Ser Gly Ile Ser Arg Gly Ser Gly Asp Ile Gly Tyr Ala Asp Ser Val<br>    50                  55                  60 | 192 |
| aag ggc cga ttc acc atc tcc aga gac aac gcc aag aag tcc ctg tct<br>Lys Gly Arg Phe Thr Ile Ser Arg Asp Asn Ala Lys Lys Ser Leu Ser<br>65                  70                  75                  80 | 240 |
| ctg caa atg aac ggc ctg aga gcc gag gac acg gcc gtg tat tac tgt<br>Leu Gln Met Asn Gly Leu Arg Ala Glu Asp Thr Ala Val Tyr Tyr Cys<br>                85                  90                  95 | 288 |
| gcg aga ggg ggg ttc gga agt ttt gat acc tgg ggc caa ggg aca atg<br>Ala Arg Gly Gly Phe Gly Ser Phe Asp Thr Trp Gly Gln Gly Thr Met<br>            100                 105                 110 | 336 |
| gtc acc gtc tct tca gga ggt ggc gga tca gga ggc gga ggt tct ggt<br>Val Thr Val Ser Ser Gly Gly Gly Gly Ser Gly Gly Gly Gly Ser Gly<br>        115                 120                 125 | 384 |
| gga ggt ggg agt gaa att gtg ctg act cag tct cca gcc acc ctg tct<br>Gly Gly Gly Ser Glu Ile Val Leu Thr Gln Ser Pro Ala Thr Leu Ser<br>    130                 135                 140 | 432 |
| gtg tct ccc ggg gaa aga gcc acc ctc tcc tgc agg gcc agt cag agt<br>Val Ser Pro Gly Glu Arg Ala Thr Leu Ser Cys Arg Ala Ser Gln Ser<br>145                 150                 155                 160 | 480 |
| gtt agg agc tac tta gcc tgg tac caa cag aaa cct ggg cag gct ccc<br>Val Arg Ser Tyr Leu Ala Trp Tyr Gln Gln Lys Pro Gly Gln Ala Pro<br>                165                 170                 175 | 528 |
| agg ctc ctc atc tct gat gca tcc aac agg gcc act ggc atc cca gcc<br>Arg Leu Leu Ile Ser Asp Ala Ser Asn Arg Ala Thr Gly Ile Pro Ala<br>            180                 185                 190 | 576 |
| agg ttc act ggc agt ggg tct ggg aca gac ttc act ctc acc atc agc<br>Arg Phe Thr Gly Ser Gly Ser Gly Thr Asp Phe Thr Leu Thr Ile Ser<br>        195                 200                 205 | 624 |

```
agc cta gag cct gaa gat ttt gca att tat tac tgt cag cag tat cgt      672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt      720
Tyr Ser Pro Arg Thr Phe Gly Gln Gly Thr Lys Val Glu Ile Lys Arg
225                 230                 235                 240

<210> SEQ ID NO 55
<211> LENGTH: 240
<212> TYPE: PRT
<213> ORGANISM: Homo sapiens

<400> SEQUENCE: 55

Glu Val Gln Leu Val Glu Ser Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Gly Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240

<210> SEQ ID NO 56
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 9C

<400> SEQUENCE: 56 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat      96
```

```
                                          -continued

Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct     240
Lys Gly Arg Phe Thr Ile Ser Arg Asp Asn Ala Lys Lys Ser Leu Ser
65                  70                  75                  80 ctg caa atg aac ggc ctg aga gcc gag gac acg gcc gtg tat tac tgt     288
Leu Gln Met Asn Gly Leu Arg Ala Glu Asp Thr Ala Val Tyr Tyr Cys
                85                  90                  95 gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110 gtc acc gtc tct tca                                                 351
Val Thr Val Ser Ser
        115

<210> SEQ ID NO 57
<211> LENGTH: 117
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Gly Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115

<210> SEQ ID NO 58
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 9C

<400> SEQUENCE: 58 gaa att gtg ctg act cag tct cca gcc acc ctg tct gtg tct ccc ggg     48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac     96
Glu Arg Ala Thr Leu Ser Cys Arg Ala Ser Gln Ser Val Arg Ser Tyr
            20                  25                  30
```

```
tta gcc tgg tac caa cag aaa cct ggg cag gct ccc agg ctc ctc atc    144
Leu Ala Trp Tyr Gln Gln Lys Pro Gly Gln Ala Pro Arg Leu Leu Ile
         35                  40                  45 tct gat gca tcc aac agg gcc act ggc atc cca gcc agg ttc act ggc    192
Ser Asp Ala Ser Asn Arg Ala Thr Gly Ile Pro Ala Arg Phe Thr Gly
 50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg    288
Glu Asp Phe Ala Ile Tyr Tyr Cys Gln Gln Tyr Arg Tyr Ser Pro Arg
                 85                  90                  95 acg ttc ggc caa ggg acc aag gtg gag atc aaa cgt                    324
Thr Phe Gly Gln Gly Thr Lys Val Glu Ile Lys Arg
            100                 105

<210> SEQ ID NO 59
<211> LENGTH: 108
<212> TYPE: PRT
<213> ORGANISM: Homo sapiens

<400> SEQUENCE: 59

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
            100                 105

<210> SEQ ID NO 60
<211> LENGTH: 17
<212> TYPE: DNA
<213> ORGANISM: Artificial
<220> FEATURE:
<223> OTHER INFORMATION: Forward primer
<220> FEATURE:
<221> NAME/KEY: primer_bind
<222> LOCATION: (1)..(10)
<223> OTHER INFORMATION: Forward Primer

<400> SEQUENCE: 60
atacctattg cctacgg                                                  17

<210> SEQ ID NO 61
<211> LENGTH: 18
<212> TYPE: DNA
<213> ORGANISM: Artificial
<220> FEATURE:
<223> OTHER INFORMATION: Reverse Primer
<220> FEATURE:
<221> NAME/KEY: primer_bind
<222> LOCATION: (1)..(10)
<223> OTHER INFORMATION: Reverse Primer

<400> SEQUENCE: 61
```

```
tttcaacagt ctatgcgg                                              18
```

<210> SEQ ID NO 62
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6003E, specific for toxin Cn2

<400> SEQUENCE: 62

```
gag gtg cag ctg gtg gag tct ggg gga ggc ttg gta cag cct ggg ggg    48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat    96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc   144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg   192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct   240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt   288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg   336
Ala Arg Gly Gly Phe Gly Ser Phe Asp Thr Trp Gly Gln Gly Thr Met
            100                 105                 110 gtc acc gtc tct tca gga ggt ggc gga tca gga ggc gga ggt tct ggt   384
Val Thr Val Ser Ser Gly Gly Gly Gly Ser Gly Gly Gly Gly Ser Gly
        115                 120                 125 gga ggt ggg agt gaa att gtg ctg act cag tct cca gcc acc ctg tct   432
Gly Gly Gly Ser Glu Ile Val Leu Thr Gln Ser Pro Ala Thr Leu Ser
    130                 135                 140 gtg tct ccc ggg gaa aga gcc acc ctc tcc tgc agg gcc agt cag agt   480
Val Ser Pro Gly Glu Arg Ala Thr Leu Ser Cys Arg Ala Ser Gln Ser
145                 150                 155                 160 gtt agg agc tac tta gcc tgg tac cat cag ata cct ggg cag gct ccc   528
Val Arg Ser Tyr Leu Ala Trp Tyr His Gln Ile Pro Gly Gln Ala Pro
                165                 170                 175 agg ctc ctc atc tct gat gca tcc aac agg gcc act ggc atc cca gcc   576
Arg Leu Leu Ile Ser Asp Ala Ser Asn Arg Ala Thr Gly Ile Pro Ala
            180                 185                 190 agg ttc act ggc agt ggg tct ggg aca gac ttc act ctc acc atc agc   624
Arg Phe Thr Gly Ser Gly Ser Gly Thr Asp Phe Thr Leu Thr Ile Ser
        195                 200                 205 agc cta gag cct gaa gat ttt gca att tat tac tgt cag cag tat cgt   672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt   720
Tyr Ser Pro Arg Thr Phe Gly Gln Gly Thr Lys Val Glu Ile Lys Arg
225                 230                 235                 240
```

<210> SEQ ID NO 63
<211> LENGTH: 240
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr His Gln Ile Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240

<210> SEQ ID NO 64
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6003E

<400> SEQUENCE: 64 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat    96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc   144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg   192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct   240
Lys Gly Arg Phe Thr Ile Ser Arg Asp Asn Ala Lys Lys Ser Leu Ser
65                  70                  75                  80

```
ctg caa atg aac agc ctg aga gcc gag gac acg gcc gtg tat tac tgt    288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg    336
Ala Arg Gly Gly Phe Gly Ser Phe Asp Thr Trp Gly Gln Gly Thr Met
            100                 105                 110 gtc acc gtc tct tca                                                351
Val Thr Val Ser Ser
        115

<210> SEQ ID NO 65
<211> LENGTH: 117
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115

<210> SEQ ID NO 66
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv6003E

<400> SEQUENCE: 66 gaa att gtg ctg act cag tct cca gcc acc ctg tct gtg tct ccc ggg    48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac    96
Glu Arg Ala Thr Leu Ser Cys Arg Ala Ser Gln Ser Val Arg Ser Tyr
            20                  25                  30 tta gcc tgg tac cat cag ata cct ggg cag gct ccc agg ctc ctc atc    144
Leu Ala Trp Tyr His Gln Ile Pro Gly Gln Ala Pro Arg Leu Leu Ile
        35                  40                  45 tct gat gca tcc aac agg gcc act ggc atc cca gcc agg ttc act ggc    192
Ser Asp Ala Ser Asn Arg Ala Thr Gly Ile Pro Ala Arg Phe Thr Gly
    50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg    288
Glu Asp Phe Ala Ile Tyr Tyr Cys Gln Gln Tyr Arg Tyr Ser Pro Arg
```

```
                    85                  90                  95
acg ttc ggc caa ggg acc aag gtg gag atc aaa cgt                      324
Thr Phe Gly Gln Gly Thr Lys Val Glu Ile Lys Arg
            100                 105

<210> SEQ ID NO 67
<211> LENGTH: 108
<212> TYPE: PRT
<213> ORGANISM: Homo sapiens

<400> SEQUENCE: 67

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr His Gln Ile Pro Gly Gln Ala Pro Arg Leu Leu Ile
        35                  40                  45

Ser Asp Ala Ser Asn Arg Ala Thr Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
            100                 105

<210> SEQ ID NO 68
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6003G, specific for toxin Cn2

<400> SEQUENCE: 68 gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat att tat    96
Ser Leu Arg Leu Ser Cys Ala Gly Ser Gly Phe Thr Phe Asp Ile Tyr
            20                  25                  30 gcc atg cat tgg ata cgc caa gtt cca ggg gag ggc ctg gag tgg gtc   144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg   192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct   240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt   288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg   336
Ala Arg Gly Gly Phe Gly Ser Phe Asp Thr Trp Gly Gln Gly Thr Met
            100                 105                 110 gtc acc gtc tct tca gga ggt ggc gga tca gga ggc gga ggt tct ggt   384
Val Thr Val Ser Ser Gly Gly Gly Gly Ser Gly Gly Gly Gly Ser Gly
        115                 120                 125
```

```
gga ggt ggg agt gaa att gtg ctg act cag tct cca gcc acc ctg tct        432
Gly Gly Gly Ser Glu Ile Val Leu Thr Gln Ser Pro Ala Thr Leu Ser
        130                 135                 140 gtg tct ccc ggg gaa aga gcc acc ctc tcc tgc agg gcc agt cag agt        480
Val Ser Pro Gly Glu Arg Ala Thr Leu Ser Cys Arg Ala Ser Gln Ser
145                 150                 155                 160 gtt agg agc tac tta gca tgg tac caa cag aaa cct ggg cag gct ccc        528
Val Arg Ser Tyr Leu Ala Trp Tyr Gln Gln Lys Pro Gly Gln Ala Pro
                165                 170                 175 agg ctc ctc atc tct gat gca tcc aac agg gcc act ggc atc cca gcc        576
Arg Leu Leu Ile Ser Asp Ala Ser Asn Arg Ala Thr Gly Ile Pro Ala
            180                 185                 190 agg ttc act ggc aga ggg tct ggg aca gac ttc act ctc acc atc agc        624
Arg Phe Thr Gly Arg Gly Ser Gly Thr Asp Phe Thr Leu Thr Ile Ser
        195                 200                 205 agc cta gag cct gaa gat ttt gca att tat tac tgt cag cag tat cgt        672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt        720
Tyr Ser Pro Arg Thr Phe Gly Gln Gly Thr Lys Val Glu Ile Lys Arg
225                 230                 235                 240

<210> SEQ ID NO 69
<211> LENGTH: 240
<212> TYPE: PRT
<213> ORGANISM: Homo sapiens

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Ile Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Arg Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
```

<210> SEQ ID NO 70
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6003G

<400> SEQUENCE: 70

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat att tat      96
Ser Leu Arg Leu Ser Cys Ala Gly Ser Gly Phe Thr Phe Asp Ile Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct     240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110 gtc acc gtc tct tca                                                 351
Val Thr Val Ser Ser
        115
```

<210> SEQ ID NO 71
<211> LENGTH: 117
<212> TYPE: PRT
<213> ORGANISM: Homo sapiens

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Ile Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115
```

<210> SEQ ID NO 72
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6003G

<400> SEQUENCE: 72

```
gaa att gtg ctg act cag tct cca gcc acc ctg tct gtg tct ccc ggg      48
Glu Ile Val Leu Thr Gln Ser Pro Ala Thr Leu Ser Val Ser Pro Gly
1               5                   10                  15 gaa aga gcc acc ctc tcc tgc agg gcc agt cag agt gtt agg agc tac      96
Glu Arg Ala Thr Leu Ser Cys Arg Ala Ser Gln Ser Val Arg Ser Tyr
                20                  25                  30 tta gca tgg tac caa cag aaa cct ggg cag gct ccc agg ctc ctc atc     144
Leu Ala Trp Tyr Gln Gln Lys Pro Gly Gln Ala Pro Arg Leu Leu Ile
            35                  40                  45 tct gat gca tcc aac agg gcc act ggc atc cca gcc agg ttc act ggc     192
Ser Asp Ala Ser Asn Arg Ala Thr Gly Ile Pro Ala Arg Phe Thr Gly
        50                  55                  60 aga ggg tct ggg aca gac ttc act ctc acc atc agc agc cta gag cct     240
Arg Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg     288
Glu Asp Phe Ala Ile Tyr Tyr Cys Gln Gln Tyr Arg Tyr Ser Pro Arg
                85                  90                  95 acg ttc ggc caa ggg acc aag gtg gag atc aaa cgt                     324
Thr Phe Gly Gln Gly Thr Lys Val Glu Ile Lys Arg
                100                 105
```

<210> SEQ ID NO 73
<211> LENGTH: 108
<212> TYPE: PRT
<213> ORGANISM: Homo sapiens

<400> SEQUENCE: 73

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Ala Arg Phe Thr Gly
        50                  55                  60

Arg Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
                100                 105

<210> SEQ ID NO 74
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6010H, specific for toxin Cn2

<400> SEQUENCE: 74

```
gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat        96
Ser Leu Arg Leu Ser Cys Ala Gly Ser Gly Phe Thr Phe Asp Asn Tyr
            20                  25                  30 gcc atg cat tgg ata cgc caa gtt cca ggg gtg ggc ctg gag tgg gtc       144
Ala Met His Trp Ile Arg Gln Val Pro Gly Val Gly Leu Glu Trp Val
        35                  40                  45 tca ggt att agt cgg ggc agt ggt gac ata ggc tat gcg gac tct gtg       192
Ser Gly Ile Ser Arg Gly Ser Gly Asp Ile Gly Tyr Ala Asp Ser Val
50                  55                  60 aag ggc cga ttc acc atc tcc aga gac aac gcc aag aag tcc ctg tct       240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt       288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg       336
Ala Arg Gly Gly Phe Gly Ser Phe Asp Thr Trp Gly Gln Gly Thr Met
            100                 105                 110 gtc acc gtc tct tct gga ggt ggc gga tca gga ggc gga ggt tct ggt       384
Val Thr Val Ser Ser Gly Gly Gly Gly Ser Gly Gly Gly Gly Ser Gly
        115                 120                 125 gga ggt ggg agt gaa att gtg ctg act cag tct cct gcc acc ctg tct       432
Gly Gly Gly Ser Glu Ile Val Leu Thr Gln Ser Pro Ala Thr Leu Ser
130                 135                 140 gtg tct ccc ggg gaa aga gcc acc ctc tcc tgc agg gcc agt cag agt       480
Val Ser Pro Gly Glu Arg Ala Thr Leu Ser Cys Arg Ala Ser Gln Ser
145                 150                 155                 160 gtt agg agc tac tta gcc tgg tac caa cag aaa cct ggg cag gct ccc       528
Val Arg Ser Tyr Leu Ala Trp Tyr Gln Gln Lys Pro Gly Gln Ala Pro
                165                 170                 175 agg ctc ctc atc tct gat gca tcc aac agg gcc act ggc atc cca gcc       576
Arg Leu Leu Ile Ser Asp Ala Ser Asn Arg Ala Thr Gly Ile Pro Ala
            180                 185                 190 agg ttc act ggc aga ggg tct ggg aca gac ttc act ctc acc atc agc       624
Arg Phe Thr Gly Arg Gly Ser Gly Thr Asp Phe Thr Leu Thr Ile Ser
        195                 200                 205 agc cta gag cct gaa gat ttt gca att tat tac tgt cag cag tat cgt       672
Ser Leu Glu Pro Glu Asp Phe Ala Ile Tyr Tyr Cys Gln Gln Tyr Arg
210                 215                 220 tac tca cct cgg acg ttc ggc caa ggg acc aag gtg gag atc aaa cgt       720
Tyr Ser Pro Arg Thr Phe Gly Gln Gly Thr Lys Val Glu Ile Lys Arg
225                 230                 235                 240
```

<210> SEQ ID NO 75
<211> LENGTH: 240
<212> TYPE: PRT
<213> ORGANISM: Homo sapiens

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Val Gly Leu Glu Trp Val
        35                  40                  45

Ser Gly Ile Ser Arg Gly Ser Gly Asp Ile Gly Tyr Ala Asp Ser Val
```

```
                    50                  55                  60
Lys Gly Arg Phe Thr Ile Ser Arg Asp Asn Ala Lys Lys Ser Leu Ser
 65                  70                  75                  80

Leu Gln Met Asn Ser Leu Arg Ala Glu Asp Thr Ala Val Tyr Tyr Cys
                 85                  90                  95

Ala Arg Gly Gly Phe Gly Ser Phe Asp Thr Trp Gly Gln Gly Thr Met
             100                 105                 110

Val Thr Val Ser Ser Gly Gly Gly Ser Gly Gly Gly Gly Ser Gly
         115                 120                 125

Gly Gly Gly Ser Glu Ile Val Leu Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Arg Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
210                 215                 220

Tyr Ser Pro Arg Thr Phe Gly Gln Gly Thr Lys Val Glu Ile Lys Arg
225                 230                 235                 240

<210> SEQ ID NO 76
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6010H

<400> SEQUENCE: 76 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
 1               5                  10                  15 tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
             20                  25                  30 gcc atg cat tgg ata cgc caa gtt cca ggg gtg ggc ctg gag tgg gtc     144
Ala Met His Trp Ile Arg Gln Val Pro Gly Val Gly Leu Glu Trp Val
         35                  40                  45 tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
     50                  55                  60 aag ggc cga ttc acc atc tcc aga gac aac gcc aag aag tcc ctg tct     240
Lys Gly Arg Phe Thr Ile Ser Arg Asp Asn Ala Lys Lys Ser Leu Ser
 65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                 85                  90                  95 gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110 gtc acc gtc tct tct                                                 351
Val Thr Val Ser Ser
        115
```

<210> SEQ ID NO 77
<211> LENGTH: 117
<212> TYPE: PRT
<213> ORGANISM: Homo sapiens

<400> SEQUENCE: 77

```
Glu Val Gln Leu Val Glu Ser Gly Gly Gly Leu Val Gln Pro Gly Gly
 1               5                  10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Val Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115
```

<210> SEQ ID NO 78
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6010H

<400> SEQUENCE: 78

```
gaa att gtg ctg act cag tct cct gcc acc ctg tct gtg tct ccc ggg      48
Glu Ile Val Leu Thr Gln Ser Pro Ala Thr Leu Ser Val Ser Pro Gly
 1               5                  10                  15 gaa aga gcc acc ctc tcc tgc agg gcc agt cag agt gtt agg agc tac      96
Glu Arg Ala Thr Leu Ser Cys Arg Ala Ser Gln Ser Val Arg Ser Tyr
            20                  25                  30 tta gcc tgg tac caa cag aaa cct ggg cag gct ccc agg ctc ctc atc     144
Leu Ala Trp Tyr Gln Gln Lys Pro Gly Gln Ala Pro Arg Leu Leu Ile
        35                  40                  45 tct gat gca tcc aac agg gcc act ggc atc cca gcc agg ttc act ggc     192
Ser Asp Ala Ser Asn Arg Ala Thr Gly Ile Pro Ala Arg Phe Thr Gly
    50                  55                  60 aga ggg tct ggg aca gac ttc act ctc acc atc agc agc cta gag cct     240
Arg Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg     288
Glu Asp Phe Ala Ile Tyr Tyr Cys Gln Gln Tyr Arg Tyr Ser Pro Arg
                85                  90                  95 acg ttc ggc caa ggg acc aag gtg gag atc aaa cgt                     324
Thr Phe Gly Gln Gly Thr Lys Val Glu Ile Lys Arg
            100                 105
```

<210> SEQ ID NO 79
<211> LENGTH: 108
<212> TYPE: PRT
<213> ORGANISM: Homo sapiens

<400> SEQUENCE: 79

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Ala Arg Phe Thr Gly
    50                  55                  60

Arg Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Tyr Arg Tyr Ser Pro Arg
                85                  90                  95

Thr Phe Gly Gln Gly Thr Lys Val Glu Ile Lys Arg
                100                 105

<210> SEQ ID NO 80
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6011G, specific for toxin Cn2

<400> SEQUENCE: 80
```

| | | | | | | | | | | | | | | | | |
|---|---|---|---|---|---|---|---|---|---|---|---|---|---|---|---|---|
| gag gtg cag ctg gtg gag tct ggg gga ggc ttg gta cag cct ggg ggg | | | | | | | | | | | | | | | | 48 |
| Glu Val Gln Leu Val Glu Ser Gly Gly Gly Leu Val Gln Pro Gly Gly | | | | | | | | | | | | | | | | |
| 1               5                   10                  15 | | | | | | | | | | | | | | | | |
| tcc ctg aga ctc tcc tgt gca ggc tct gga ttc acc ttt gat aat tat | | | | | | | | | | | | | | | | 96 |
| Ser Leu Arg Leu Ser Cys Ala Gly Ser Gly Phe Thr Phe Asp Asn Tyr | | | | | | | | | | | | | | | | |
|                 20                  25                  30 | | | | | | | | | | | | | | | | |
| gcc atg cat tgg ata cgc caa gtt cca ggg gag ggc ctg gag tgg gtc | | | | | | | | | | | | | | | | 144 |
| Ala Met His Trp Ile Arg Gln Val Pro Gly Glu Gly Leu Glu Trp Val | | | | | | | | | | | | | | | | |
|             35                  40                  45 | | | | | | | | | | | | | | | | |
| tca ggt att agt cgg ggc agt ggt gac ata ggc tac gcg gac tct gtg | | | | | | | | | | | | | | | | 192 |
| Ser Gly Ile Ser Arg Gly Ser Gly Asp Ile Gly Tyr Ala Asp Ser Val | | | | | | | | | | | | | | | | |
|     50                  55                  60 | | | | | | | | | | | | | | | | |
| aag ggc cga ttc acc atc tcc aga gac aac gcc aag aag tcc ctg tct | | | | | | | | | | | | | | | | 240 |
| Lys Gly Arg Phe Thr Ile Ser Arg Asp Asn Ala Lys Lys Ser Leu Ser | | | | | | | | | | | | | | | | |
| 65                  70                  75                  80 | | | | | | | | | | | | | | | | |
| ctg caa atg aac agc ctg aga gcc gag gac acg gcc gtg tat tac tgt | | | | | | | | | | | | | | | | 288 |
| Leu Gln Met Asn Ser Leu Arg Ala Glu Asp Thr Ala Val Tyr Tyr Cys | | | | | | | | | | | | | | | | |
|                 85                  90                  95 | | | | | | | | | | | | | | | | |
| gcg aga ggg ggg ttc gga agt ttt gat acc tgg ggc caa ggg aca atg | | | | | | | | | | | | | | | | 336 |
| Ala Arg Gly Gly Phe Gly Ser Phe Asp Thr Trp Gly Gln Gly Thr Met | | | | | | | | | | | | | | | | |
|             100                 105                 110 | | | | | | | | | | | | | | | | |
| gtc acc gtc tct tca gga ggt ggc gga tca gga ggc gga ggt tct ggt | | | | | | | | | | | | | | | | 384 |
| Val Thr Val Ser Ser Gly Gly Gly Gly Ser Gly Gly Gly Gly Ser Gly | | | | | | | | | | | | | | | | |
|         115                 120                 125 | | | | | | | | | | | | | | | | |
| gga ggt ggg agt gaa att gtg ctg act cag tct cca gcc gcc ctg tct | | | | | | | | | | | | | | | | 432 |
| Gly Gly Gly Ser Glu Ile Val Leu Thr Gln Ser Pro Ala Ala Leu Ser | | | | | | | | | | | | | | | | |
| 130                 135                 140 | | | | | | | | | | | | | | | | |
| gtg tct ccc ggg gaa aga gcc acc ctc tcc tgc agg gcc agt cag agt | | | | | | | | | | | | | | | | 480 |
| Val Ser Pro Gly Glu Arg Ala Thr Leu Ser Cys Arg Ala Ser Gln Ser | | | | | | | | | | | | | | | | |
| 145                 150                 155                 160 | | | | | | | | | | | | | | | | |
| gtt agg agc tac tta gcc tgg tac caa cgg aaa cct ggg cag gct ccc | | | | | | | | | | | | | | | | 528 |
| Val Arg Ser Tyr Leu Ala Trp Tyr Gln Arg Lys Pro Gly Gln Ala Pro | | | | | | | | | | | | | | | | |
|                 165                 170                 175 | | | | | | | | | | | | | | | | |
| agg ctc ctc atc tct gat gca tcc aac agg gcc act ggc atc cca gcc | | | | | | | | | | | | | | | | 576 |

```
agg ttc act ggc agt ggg tct ggg aca gac ttc act ctc acc atc agc      624
Arg Phe Thr Gly Ser Gly Ser Gly Thr Asp Phe Thr Leu Thr Ile Ser
        195                 200                 205 agc cta gag cct gaa gat ttt gca att tat tac tgt cag cag tat cgt      672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt      720
Tyr Ser Pro Arg Thr Phe Gly Gln Gly Thr Lys Val Glu Ile Lys Arg
225                 230                 235                 240
```

<210> SEQ ID NO 81
<211> LENGTH: 240
<212> TYPE: PRT
<213> ORGANISM: Homo sapiens

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Ala Ala Leu Ser
    130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Arg Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240
```

<210> SEQ ID NO 82
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6011G

<400> SEQUENCE: 82

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg ggc agt ggt gac ata ggc tac gcg gac tct gtg     192
Ser Gly Ile Ser Arg Gly Ser Gly Asp Ile Gly Tyr Ala Asp Ser Val
    50                  55                  60 aag ggc cga ttc acc atc tcc aga gac aac gcc aag aag tcc ctg tct     240
Lys Gly Arg Phe Thr Ile Ser Arg Asp Asn Ala Lys Lys Ser Leu Ser
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110 gtc acc gtc tct tca                                                  351
Val Thr Val Ser Ser
        115

<210> SEQ ID NO 83
<211> LENGTH: 117
<212> TYPE: PRT
<213> ORGANISM: Homo sapiens

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asn Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115

<210> SEQ ID NO 84
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6011G

<400> SEQUENCE: 84 gaa att gtg ctg act cag tct cca gcc gcc ctg tct gtg tct ccc ggg      48
Glu Ile Val Leu Thr Gln Ser Pro Ala Ala Leu Ser Val Ser Pro Gly
```

```
                  1               5              10              15 gaa aga gcc acc ctc tcc tgc agg gcc agt cag agt gtt agg agc tac        96
Glu Arg Ala Thr Leu Ser Cys Arg Ala Ser Gln Ser Val Arg Ser Tyr
             20                  25                  30 tta gcc tgg tac caa cgg aaa cct ggg cag gct ccc agg ctc ctc atc       144
Leu Ala Trp Tyr Gln Arg Lys Pro Gly Gln Ala Pro Arg Leu Leu Ile
         35                  40                  45 tct gat gca tcc aac agg gcc act ggc atc cca gcc agg ttc act ggc       192
Ser Asp Ala Ser Asn Arg Ala Thr Gly Ile Pro Ala Arg Phe Thr Gly
     50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca att tat tac tgt cag cag tat cgt tac tca cct cgg       288
Glu Asp Phe Ala Ile Tyr Tyr Cys Gln Gln Tyr Arg Tyr Ser Pro Arg
                 85                  90                  95 acg ttc ggc caa ggg acc aag gtg gag atc aaa cgt                       324
Thr Phe Gly Gln Gly Thr Lys Val Glu Ile Lys Arg
             100                 105
```

<210> SEQ ID NO 85
<211> LENGTH: 108
<212> TYPE: PRT
<213> ORGANISM: Homo sapiens

<400> SEQUENCE: 85

```
Glu Ile Val Leu Thr Gln Ser Pro Ala Ala Leu Ser Val Ser Pro Gly
  1               5                  10                  15

Glu Arg Ala Thr Leu Ser Cys Arg Ala Ser Gln Ser Val Arg Ser Tyr
             20                  25                  30

Leu Ala Trp Tyr Gln Arg Lys Pro Gly Gln Ala Pro Arg Leu Leu Ile
         35                  40                  45

Ser Asp Ala Ser Asn Arg Ala Thr Gly Ile Pro Ala Arg Phe Thr Gly
     50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln Tyr Arg Tyr Ser Pro Arg
                 85                  90                  95

Thr Phe Gly Gln Gly Thr Lys Val Glu Ile Lys Arg
             100                 105
```

<210> SEQ ID NO 86
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6105FF, specific for toxin Cn2

<400> SEQUENCE: 86

```
gag gtg cag ctg gtg gag tct ggg gga ggc ttg gta cag c

-continued

```
tca ggt att agt cgg ggc agt ggt gac ata ggc tat gcg gac tct gtg        192
Ser Gly Ile Ser Arg Gly Ser Gly Asp Ile Gly Tyr Ala Asp Ser Val
     50                  55                  60 aag ggc cga ttc acc atc tcc aga gac gac gcc aag aag tcc ctg tct        240
Lys Gly Arg Phe Thr Ile Ser Arg Asp Asp Ala Lys Lys Ser Leu Ser
 65                  70                  75                  80 ctg caa atg aac agc ctg aga gcc gag gac acg gcc gtg tat tac tgt        288
Leu Gln Met Asn Ser Leu Arg Ala Glu Asp Thr Ala Val Tyr Tyr Cys
                 85                  90                  95 gcg aga ggg ggg ttc gga agt ttt gat tcc tgg ggc caa ggg aca atg        336
Ala Arg Gly Gly Phe Gly Ser Phe Asp Ser Trp Gly Gln Gly Thr Met
            100                 105                 110 gtc acc gtc tct tca gga ggt ggc gga tca gga ggc gga ggt tct ggt        384
Val Thr Val Ser Ser Gly Gly Gly Gly Ser Gly Gly Gly Gly Ser Gly
        115                 120                 125 gga ggt ggg agt gaa att gtg ctg act cag tct cca gcc act ctg tct        432
Gly Gly Gly Ser Glu Ile Val Leu Thr Gln Ser Pro Ala Thr Leu Ser
130                 135                 140 gtg tct ccc ggg gaa aga gcc acc ctc tcc tgc agg gcc agt cag agt        480
Val Ser Pro Gly Glu Arg Ala Thr Leu Ser Cys Arg Ala Ser Gln Ser
145                 150                 155                 160 gtt agg agc tac tta gcc tgg tac caa cag aaa cct ggg cag gct ccc        528
Val Arg Ser Tyr Leu Ala Trp Tyr Gln Gln Lys Pro Gly Gln Ala Pro
                165                 170                 175 agg ctc ctc atc tct gat gca tcc aac agg gcc act ggc atc cca acc        576
Arg Leu Leu Ile Ser Asp Ala Ser Asn Arg Ala Thr Gly Ile Pro Thr
            180                 185                 190 agg ttc act ggc agt ggg tct ggg aca gac ttc act ctc acc atc agc        624
Arg Phe Thr Gly Ser Gly Ser Gly Thr Asp Phe Thr Leu Thr Ile Ser
        195                 200                 205 agc cta gag cct gaa gat ttt gca att tat tac tgt cag cag tat cgt        672
Ser Leu Glu Pro Glu Asp Phe Ala Ile Tyr Tyr Cys Gln Gln Tyr Arg
    210                 215                 220 tac tca cct cgg acg ttc ggc caa ggg acc aag gtg gag atc aaa cgt        720
Tyr Ser Pro Arg Thr Phe Gly Gln Gly Thr Lys Val Glu Ile Lys Arg
225                 230                 235                 240
```

<210> SEQ ID NO 87
<211> LENGTH: 240
<212> TYPE: PRT
<213> ORGANISM: Homo sapiens

<400> SEQUENCE: 87

```
Glu Val Gln Leu Val Glu Ser Gly Gly Gly Leu Val Gln Pro Gly Gly
 1               5                  10                  15

Ser Leu Arg Leu Ser Cys Ala Gly Ser Gly Phe Thr Phe Asp Asn Tyr
                20                  25                  30

Ala Met His Trp Ile Arg Gln Val Pro Gly Glu Gly Leu Glu Trp Val
            35                  40                  45

Ser Gly Ile Ser Arg Gly Ser Gly Asp Ile Gly Tyr Ala Asp Ser Val
        50                  55                  60

Lys Gly Arg Phe Thr Ile Ser Arg Asp Asp Ala Lys Lys Ser Leu Ser
 65                  70                  75                  80

Leu Gln Met Asn Ser Leu Arg Ala Glu Asp Thr Ala Val Tyr Tyr Cys
                 85                  90                  95

Ala Arg Gly Gly Phe Gly Ser Phe Asp Ser Trp Gly Gln Gly Thr Met
            100                 105                 110

Val Thr Val Ser Ser Gly Gly Gly Gly Ser Gly Gly Gly Gly Ser Gly
        115                 120                 125
```

-continued

```
Gly Gly Gly Ser Glu Ile Val Leu Thr Gln Ser Pro Ala Thr Leu Ser
        130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Thr
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240

<210> SEQ ID NO 88
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6105F

<400> SEQUENCE: 88 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
            20                  25                  30 gcc atg cat tgg ata cgc caa gtt cca ggg gag ggc ctg gag tgg gtc     144
Ala Met His Trp Ile Arg Gln Val Pro Gly Glu Gly Leu Glu Trp Val
        35                  40                  45 tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
    50                  55                  60 aag ggc cga ttc acc atc tcc aga gac gac gcc aag aag tcc ctg tct     240
Lys Gly Arg Phe Thr Ile Ser Arg Asp Asp Ala Lys Lys Ser Leu Ser
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gcg aga ggg ggg ttc gga agt ttt gat tcc tgg ggc caa ggg aca atg     336
Ala Arg Gly Gly Phe Gly Ser Phe Asp Ser Trp Gly Gln Gly Thr Met
            100                 105                 110 gtc acc gtc tct tca                                                  351
Val Thr Val Ser Ser
        115

<210> SEQ ID NO 89
<211> LENGTH: 117
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30
```

```
Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
 50                  55                  60

Lys Gly Arg Phe Thr Ile Ser Arg Asp Asp Ala Lys Lys Ser Leu Ser
 65                  70                  75                  80

Leu Gln Met Asn Ser Leu Arg Ala Glu Asp Thr Ala Val Tyr Tyr Cys
                 85                  90                  95

Ala Arg Gly Gly Phe Gly Ser Phe Asp Ser Trp Gly Gln Gly Thr Met
                100                 105                 110

Val Thr Val Ser Ser
        115

<210> SEQ ID NO 90
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6105F

<400> SEQUENCE: 90 gaa att gtg ctg act cag tct cca gcc act ctg tct gtg tct ccc ggg      48
Glu Ile Val Leu Thr Gln Ser Pro Ala Thr Leu Ser Val Ser Pro Gly
 1               5                  10                  15 gaa aga gcc acc ctc tcc tgc agg gcc agt cag agt gtt agg agc tac      96
Glu Arg Ala Thr Leu Ser Cys Arg Ala Ser Gln Ser Val Arg Ser Tyr
                20                  25                  30 tta gcc tgg tac caa cag aaa cct ggg cag gct ccc agg ctc ctc atc     144
Leu Ala Trp Tyr Gln Gln Lys Pro Gly Gln Ala Pro Arg Leu Leu Ile
            35                  40                  45 tct gat gca tcc aac agg gcc act ggc atc cca acc agg ttc act ggc     192
Ser Asp Ala Ser Asn Arg Ala Thr Gly Ile Pro Thr Arg Phe Thr Gly
         50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80 gaa gat ttt gca att tat tac tgt cag cag tat cgt tac tca cct cgg     288
Glu Asp Phe Ala Ile Tyr Tyr Cys Gln Gln Tyr Arg Tyr Ser Pro Arg
                 85                  90                  95 acg ttc ggc caa ggg acc aag gtg gag atc aaa cgt                     324
Thr Phe Gly Gln Gly Thr Lys Val Glu Ile Lys Arg
                100                 105

<210> SEQ ID NO 91
<211> LENGTH: 108
<212> TYPE: PRT
<213> ORGANISM: Homo sapiens

<400> SEQUENCE: 91

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Arg Ser Tyr
                20                  25                  30

Leu Ala Trp Tyr Gln Gln Lys Pro Gly Gln Ala Pro Arg Leu Leu Ile
            35                  40                  45

Ser Asp Ala Ser Asn Arg Ala Thr Gly Ile Pro Thr Arg Phe Thr Gly
         50                  55                  60
```

```
Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln Tyr Arg Tyr Ser Pro Arg
             85                  90                  95

Thr Phe Gly Gln Gly Thr Lys Val Glu Ile Lys Arg
            100                 105
```

<210> SEQ ID NO 92
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION: Product= scFv 6103E, specific for toxin Cn2

<400> SEQUENCE: 92

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
 1               5                  10                  15
tcc ctg aga ctc tcc tgt gca ggc tct gga ttc acc ttt gat aat tat      96
Ser Leu Arg Leu Ser Cys Ala Gly Ser Gly Phe Thr Phe Asp Asn Tyr
             20                  25                  30
gcc atg cat tgg ata cgc caa gtt cca ggg gag ggc ctg gag tgg gtc     144
Ala Met His Trp Ile Arg Gln Val Pro Gly Glu Gly Leu Glu Trp Val
         35                  40                  45
tca ggt att agt cgg ggc agt ggt gac ata ggc tat gcg gac tct gtg     192
Ser Gly Ile Ser Arg Gly Ser Gly Asp Ile Gly Tyr Ala Asp Ser Val
     50                  55                  60
aag ggc cga ttc acc atc tcc aga gac gac gcc aag aag tcc ctg tct     240
Lys Gly Arg Phe Thr Ile Ser Arg Asp Asp Ala Lys Lys Ser Leu Ser
 65                  70                  75                  80
ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
             85                  90                  95
gcg aga ggg ggg ttc gga agt ttt gat acc tgg ggc caa ggg aca atg     336
Ala Arg Gly Gly Phe Gly Ser Phe Asp Thr Trp Gly Gln Gly Thr Met
            100                 105                 110
gtc acc gtc tct tca gga ggt ggc gga tca gga ggc gga ggt tct ggt     384
Val Thr Val Ser Ser Gly Gly Gly Gly Ser Gly Gly Gly Gly Ser Gly
        115                 120                 125
gga ggt ggg agt gaa att gtg ctg act cag tct cca gtc acc ctg tct     432
Gly Gly Gly Ser Glu Ile Val Leu Thr Gln Ser Pro Val Thr Leu Ser
    130                 135                 140
gtg tct ccc ggg gaa aga gcc acc ctc tcc tgc agg gcc agt cag agt     480
Val Ser Pro Gly Glu Arg Ala Thr Leu Ser Cys Arg Ala Ser Gln Ser
145                 150                 155                 160
gtc agg agc tac tta gcc tgg tac caa cag aaa cct ggg cag gct ccc     528
Val Arg Ser Tyr Leu Ala Trp Tyr Gln Gln Lys Pro Gly Gln Ala Pro
                165                 170                 175
agg ctc ctc atc tct gat gca tcc aac agg gcc act ggc atc cca gcc     576
Arg Leu Leu Ile Ser Asp Ala Ser Asn Arg Ala Thr Gly Ile Pro Ala
            180                 185                 190
agg ttc act ggc agt ggg tct ggg aca gac ttc act ctc acc atc agc     624
Arg Phe Thr Gly Ser Gly Ser Gly Thr Asp Phe Thr Leu Thr Ile Ser
        195                 200                 205
agc cta gag cct gaa gat ttt gca att tat tac tgt cag cag tat cgt     672
Ser Leu Glu Pro Glu Asp Phe Ala Ile Tyr Tyr Cys Gln Gln Tyr Arg
    210                 215                 220
tac tca cct cgg acg ttc ggc caa ggg acc aag gtg gag atc aaa cgt     720
Tyr Ser Pro Arg Thr Phe Gly Gln Gly Thr Lys Val Glu Ile Lys Arg
225                 230                 235                 240
```

<210> SEQ ID NO 93
<211> LENGTH: 240
<212> TYPE: PRT
<213> ORGANISM: Homo sapiens

<400> SEQUENCE: 93

```
Glu Val Gln Leu Val Glu Ser Gly Gly Gly Leu Val Gln Pro Gly Gly
 1               5                  10                  15

Ser Leu Arg Leu Ser Cys Ala Gly Ser Gly Phe Thr Phe Asp Asn Tyr
```

```
                  20                  25                  30
Ala Met His Trp Ile Arg Gln Val Pro Gly Glu Gly Leu Glu Trp Val
             35                  40                  45

Ser Gly Ile Ser Arg Gly Ser Gly Asp Ile Gly Tyr Ala Asp Ser Val
         50                  55                  60

Lys Gly Arg Phe Thr Ile Ser Arg Asp Asp Ala Lys Lys Ser Leu Ser
 65                  70                  75                  80

Leu Gln Met Asn Ser Leu Arg Ala Glu Asp Thr Ala Val Tyr Tyr Cys
                     85                  90                  95

Ala Arg Gly Gly Phe Gly Ser Phe Asp Thr Trp Gly Gln Gly Thr Met
                100                 105                 110

Val Thr Val Ser Ser Gly Gly Gly Ser Gly Gly Gly Gly Ser Gly
             115                 120                 125

Gly Gly Gly Ser Glu Ile Val Leu Thr Gln Ser Pro Val Thr Leu Ser
        130                 135                 140

Val Ser Pro Gly Glu Arg Ala Thr Leu Ser Cys Arg Ala Ser Gln Ser
145                 150                 155                 160

Val Arg Ser Tyr Leu Ala Trp Tyr Gln Gln Lys Pro Gly Gln Ala Pro
                165                 170                 175

Arg Leu Leu Ile Ser Asp Ala Ser Asn Arg Ala Thr Gly Ile Pro Ala
            180                 185                 190

Arg Phe Thr Gly Ser Gly Ser Gly Thr Asp Phe Thr Leu Thr Ile Ser
        195                 200                 205

Ser Leu Glu Pro Glu Asp Phe Ala Ile Tyr Tyr Cys Gln Gln Tyr Arg
    210                 215                 220

Tyr Ser Pro Arg Thr Phe Gly Gln Gly Thr Lys Val Glu Ile Lys Arg
225                 230                 235                 240

<210> SEQ ID NO 94
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: Product= VH of scFv 6103E

<400> SEQUENCE: 94 gag gtg cag ctg gtg gag tct ggg gga ggc ttg gta cag cct ggg ggg    48
Glu Val Gln Leu Val Glu Ser Gly Gly Gly Leu Val Gln Pro Gly Gly
 1               5                  10                  15 tcc ctg aga ctc tcc tgt gca ggc tct gga ttc acc ttt gat aat tat    96
Ser Leu Arg Leu Ser Cys Ala Gly Ser Gly Phe Thr Phe Asp Asn Tyr
             20                  25                  30 gcc atg cat tgg ata cgc caa gtt cca ggg gag ggc ctg gag tgg gtc   144
Ala Met His Trp Ile Arg Gln Val Pro Gly Glu Gly Leu Glu Trp Val
         35                  40                  45 tca ggt att agt cgg ggc agt ggt gac ata ggc tat gcg gac tct gtg   192
Ser Gly Ile Ser Arg Gly Ser Gly Asp Ile Gly Tyr Ala Asp Ser Val
     50                  55                  60 aag ggc cga ttc acc atc tcc aga gac gac gcc aag aag tcc ctg tct   240
Lys Gly Arg Phe Thr Ile Ser Arg Asp Asp Ala Lys Lys Ser Leu Ser
 65                  70                  75                  80 ctg caa atg aac agc ctg aga gcc gag gac acg gcc gtg tat tac tgt   288
Leu Gln Met Asn Ser Leu Arg Ala Glu Asp Thr Ala Val Tyr Tyr Cys
                     85                  90                  95 gcg aga ggg ggg ttc gga agt ttt gat acc tgg ggc caa ggg aca atg   336
Ala Arg Gly Gly Phe Gly Ser Phe Asp Thr Trp Gly Gln Gly Thr Met
                100                 105                 110
```

```
                  100                 105                 110
gtc acc gtc tct tca                                                    351
Val Thr Val Ser Ser
        115

<210> SEQ ID NO 95
<211> LENGTH: 117
<212> TYPE: PRT
<213> ORGANISM: Homo sapiens

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Asp Asn Tyr
            20                  25                  30

Ala Met His Trp Ile Arg Gln Val Pro Gly Glu Gly Leu Glu Trp Val
        35                  40                  45

Ser Gly Ile Ser Arg Gly Ser Gly Asp Ile Gly Tyr Ala Asp Ser Val
    50                  55                  60

Lys Gly Arg Phe Thr Ile Ser Arg Asp Asp Ala Lys Lys Ser Leu Ser
65                  70                  75                  80

Leu Gln Met Asn Ser Leu Arg Ala Glu Asp Thr Ala Val Tyr Tyr Cys
                85                  90                  95

Ala Arg Gly Gly Phe Gly Ser Phe Asp Thr Trp Gly Gln Gly Thr Met
            100                 105                 110

Val Thr Val Ser Ser
        115

<210> SEQ ID NO 96
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: Product= VL of scFv 6103E

<400> SEQUENCE: 96 gaa att gtg ctg act cag tct cca gtc acc ctg tct gtg tct ccc ggg      48
Glu Ile Val Leu Thr Gln Ser Pro Val Thr Leu Ser Val Ser Pro Gly
1               5                   10                  15 gaa aga gcc acc ctc tcc tgc agg gcc agt cag agt gtc agg agc tac      96
Glu Arg Ala Thr Leu Ser Cys Arg Ala Ser Gln Ser Val Arg Ser Tyr
            20                  25                  30 tta gcc tgg tac caa cag aaa cct ggg cag gct ccc agg ctc ctc atc     144
Leu Ala Trp Tyr Gln Gln Lys Pro Gly Gln Ala Pro Arg Leu Leu Ile
        35                  40                  45 tct gat gca tcc aac agg gcc act ggc atc cca gcc agg ttc act ggc     192
Ser Asp Ala Ser Asn Arg Ala Thr Gly Ile Pro Ala Arg Phe Thr Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca att tat tac tgt cag cag tat cgt tac tca cct cgg     288
Glu Asp Phe Ala Ile Tyr Tyr Cys Gln Gln Tyr Arg Tyr Ser Pro Arg
                85                  90                  95 acg ttc ggc caa ggg acc aag gtg gag atc aaa cgt                     324
Thr Phe Gly Gln Gly Thr Lys Val Glu Ile Lys Arg
            100                 105
```

```
<210> SEQ ID NO 97
<211> LENGTH: 108
<212> TYPE: PRT
<213> ORGANISM: Homo sapiens

<400> SEQUENCE: 97

Glu Ile Val Leu Thr Gln Ser Pro Val Thr Leu Ser Val Ser Pro Gly
 1               5                  10                  15

Glu Arg Ala Thr Leu Ser Cys Arg Ala Ser Gln Ser Val Arg Ser Tyr
             20                  25                  30

Leu Ala Trp Tyr Gln Gln Lys Pro Gly Gln Ala Pro Arg Leu Leu Ile
         35                  40                  45

Ser Asp Ala Ser Asn Arg Ala Thr Gly Ile Pro Ala Arg Phe Thr Gly
     50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln Tyr Arg Tyr Ser Pro Arg
                 85                  90                  95

Thr Phe Gly Gln Gly Thr Lys Val Glu Ile Lys Arg
            100                 105
```

HUMAN ANTIBODIES THAT SPECIFICALLY RECOGNIZE THE TOXIN CN2 FROM *CENTRUROIDES NOXIUS* SCORPION VENOM

This application claims the benefit of U.S. provisional application No. 60/671,535, filed Apr. 15, 2005, and U.S. provisional application No. 60/672,535, filed Apr. 19, 2005, both of which are abandoned and both of which are herein incorporated by reference.

BACKGROUND OF THE INVENTION

1. Field of the Invention

This invention relates generally to antibody variants. In particular, antibody variants of parent antibodies are disclosed which have one or more amino acids alterations respect to the parent antibody and a binding affinity for toxin Cn2 which is at least about 10.5 fold stronger than the binding affinity of the parent antibody for the toxin. In another embodiment the invention relates to antibody variants that neutralizes the lethal effect of both the Cn2 toxin and the whole *C. noxius* venom. The invention is also related to the coding DNAs for the antibody variants; to vector molecules comprising said coding DNAs, to cells comprising said vectors and methods for the production of the antibodies. The invention relates too to solid phases comprising the antibody variants adhered and to diagnostic systems to detect the presence of toxin Cn2 in samples, comprising immunodiagnostic systems like ELISA and immunochromatographic assay which comprise the antibodies of the present invention. Additionally, the present invention relates to a method to select improved antibodies from a mutagenized library, where said antibodies are improved not only in its affinity but in its stability too.

2. Background Art

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody to its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called $\alpha$(alpha), $\delta$(delta), $\epsilon$(epsilon), $\gamma$(gamma), $\mu$(mu), respectively. Of the various human immunoglobulin classes, only human IgG1, IgG2, IgG3 and IgM are known to activate complement.

It was disclosed in patent application WO92/01047 that antibody fragments can be displayed on the surface of bacteriophage and that they will bind antigen. Antibody fragments can be directly selected using this characteristic. This ability to isolate antibody fragments (F(ab')$_2$, Fab, Fv, scFv and $V_H$) using their display on the surface of filamentous bacteriophage has opened up the prospect of the isolation of antibody specificities (i.e. antibodies directed against a particular antigen) that were difficult or impossible to isolate previously. In particular WO92/01047 demonstrates that antibody specificities can be isolated from a human who has not been specifically immunized ('unimmunized'), even specificities for antigens such as 2-phenyl-5-oxazolone to which humans will not normally be exposed.

In vivo, affinity maturation of antibodies is driven by antigen selection of higher affinity antibody variants which are made primarily by somatic hypermutagenesis. A "repertoire shift" also often occurs in which the predominant germline genes of the secondary or tertiary response are seen to differ from those of the primary or secondary response.

Various research groups have attempted to mimic the affinity maturation process of the immune system, by introducing mutations into antibody $V_H$ and $V_L$ genes in vitro and using affinity selection to isolate mutants with improved affinity. Such mutant antibodies can be displayed on the surface of filamentous bacteriophage and improved antibodies can be selected by their better affinity for antigen or by their kinetics of dissociation (off-rate) from antigen.

Scorpionism

Scorpion stings in Mexico reach over 200,000 accidents per year with a mortality of approximately 700 people during the decades of the seventies and eighties. For the nineties, the reported fatalities were 300 and by 1998, 136 persons. During 2002 the fatal cases diminished to 70 (Weekly Epidemiological Bulletin, Mexican Health Ministry). The decrement on the mortality rate coincided with a National Campaign for anti-venom utilization, sponsored by the Mexican Institute of Social Security. Serotherapy (heterologous immune serum administration), has been used during the last century for treatment of poisonings caused by animal bites and stings in humans (Choumet, V., Audebert, F., Riviere, G., Sorkine, M., Urtizberea, M., Sabouraud, A., Scherrmann, J. M. & Bon, C. (1996) *Adv Exp Med Biol* 391, 515-20). The antivenom which is currently used in Mexico consists of purified bivalent F(ab')$_2$ fragments obtained by hyper-immunizing horses with a water extract from venomous glands of *Centruroides* scorpions (Calderon-Aranda, E. S., Hozbor, D. & Possani, L. D. (1993) *Toxicon* 31, 327-37). Polyclonal antibodies present in horse serum, are raised against the total components of the venom, however only a reduced number of toxic components are important for poisoning. From 221 species living in México, only 8 are dangerous to human beings (Dehesa-Davila, M. (1989) *Toxicon* 27, 281-6). The venom from different species of scorpions of the genus *Centruroides* are very similar in terms of toxic components (Possani, L. D., Becerril, B., Delepierre, M. & Tytgat, J. (1999) *Eur J Biochem* 264, 287-300). It is worth mentioning that in scorpion venoms there are short and long-chain peptides, known to be specifically toxic to mammals. The deadly effect was demonstrated to be for their effect on target molecules known as ion-channels. There are several distinct ion-channels that preside the permeability of many ions, such as: $Na^+$, $K^+$, $Ca^{2+}$, $Cl^-$. These are integral-membrane proteins that control cellular excitability. The most important toxins from scorpion venoms are those that recognize sodium channels (Possani, L. D., Becerril, B., Delepierre, M. & Tytgat, J. (1999) *Eur J Biochem* 264, 287-300). Thus, the identification of the deadly components (mainly toxins specific for sodium channels) in those 8 venoms could help to obtain neutralizing recombinant antibodies, which would be the constituents of the next generation of antisera. A more specific antiserum would result in a safer medicine in terms of the reduced number of distinct antibodies present and the use of homologous human antibodies, replacing the horse antibodies presently used.

BCF2, a murine monoclonal antibody characterized in our laboratory (Zamudio, F., Saavedra, R., Martin, B. M., Gurrola-Briones, G., Herion, P. & Possani, L. D. (1992) *Eur J Biochem* 204, 281-92), neutralizes the toxic effects of Cn2 (a toxin specific for sodium channels of mammals), one of the most abundant and toxic components of the venom from the scorpion *Centruroides noxius* Hoffmann (6.8% of total venom; $LD_{50}$=0.25 µg/20 g of mouse weight). BCF2 is also able of neutralizing the whole venom ($LD_{50}$=2.5 µg/20 g of mouse weight) (Licea, A. F., Becerril, B. & Possani, L. D. (1996) *Toxicon* 34, 843-7). These findings suggested the possibility of obtaining recombinant antivenom of human origin. It would consist exclusively of specific antibody fragments, would be autologous, safer and more efficient for therapeutic application in humans.

The expression of several antibody formats on the surface of filamentous phages (phage display), has allowed the generation of large repertoires for different purposes, revolutionizing among others, the field of antibody engineering (Stockwin, L. H. & Holmes, S. (2003) *Biochem Soc Trans* 31, 433-6., Brekke, O. H. & Loset, G. A. (2003) *Curr Opin Pharmacol* 3, 544-50., Benhar, I. (2001) *Biotechnol Adv* 19, 1-33., Roque, A. C., Lowe, C. R. & Taipa, M. A. (2004) *Biotechnol Prog* 20, 639-54). The panning of these repertoires with different antigens constitutes a selection step analogous to that occurring in the immune system (Hoogenboom, H. R. & Winter, G. (1992) *J Mol Biol* 227, 381-8., Winter, G., Griffiths, A. D., Hawkins, R. E. & Hoogenboom, H. R. (1994) *Annu Rev Immunol* 12, 433-55), which allows the isolation of antibody fragments of diverse specificities.

BRIEF DESCRIPTION OF THE DRAWINGS/FIGURES

FIG. 1. Amino acid sequence alignment of scFvs selected from a human repertoire. These sequences include the C-myc carboxy-terminal tag (nucleotides 251 to 267 in C1 and 241 to 257 in 3F) followed by a hexameric His-tag. Complementarity determining regions (CDR) of $V_H$ and $V_L$ are delimited by a rectangle. The closest germ line, diversity and joining segments for the $V_H$ domain of clone C1 were IGHV3-30*18, IGHD2-21*01 and IGHJ2*01 respectively. For the $V_L$, the germline and the joining segments corresponded to IGVL1-44*01 and IGLJ1*01. The closest germ line, diversity and joining segments for the $V_H$ domain of clone 3F were IGHV3-9*01; IGHD2-8*02; IGHJ3*02. For the VK, the germline and the joining segments corresponded to IGVK3-11*01; IGKJ1*01. The sequences were submitted to the GenBank under the accession numbers AY781342 (C1) and AY781338 (3F).

FIG. 2. Specificity of phage-antibodies 3F and C1. A). Cross-reactivity: scFv 3F (hatched boxes) and scFv C1 (empty boxes). Binding was determined by ELISA to a variety of antigens (all of them scorpion toxins). Cn2, Cll1, Cll2, Pg7, Pg8, specific toxins for sodium channels and Pg5, toxin specific for potassium channel, all at a concentration of 3 µg/ml; FII (Toxic fraction II of *C. limpidus limpidus* venom) at 20 µg/ml. Phage antibodies at $1 \times 10^{11}$ phages/ml. B). Amino acid sequences of toxin Cn2 (*C. noxius*) and homologous toxins Cll1 and Cll2 (*C. limpidus limpidus*). The asterisks indicate identity, single dots indicate a "weak" conserved group of residues and double dots indicate a "strong" group of conserved residues as defined in the ClustalX (1.81) program.

Figure 3:
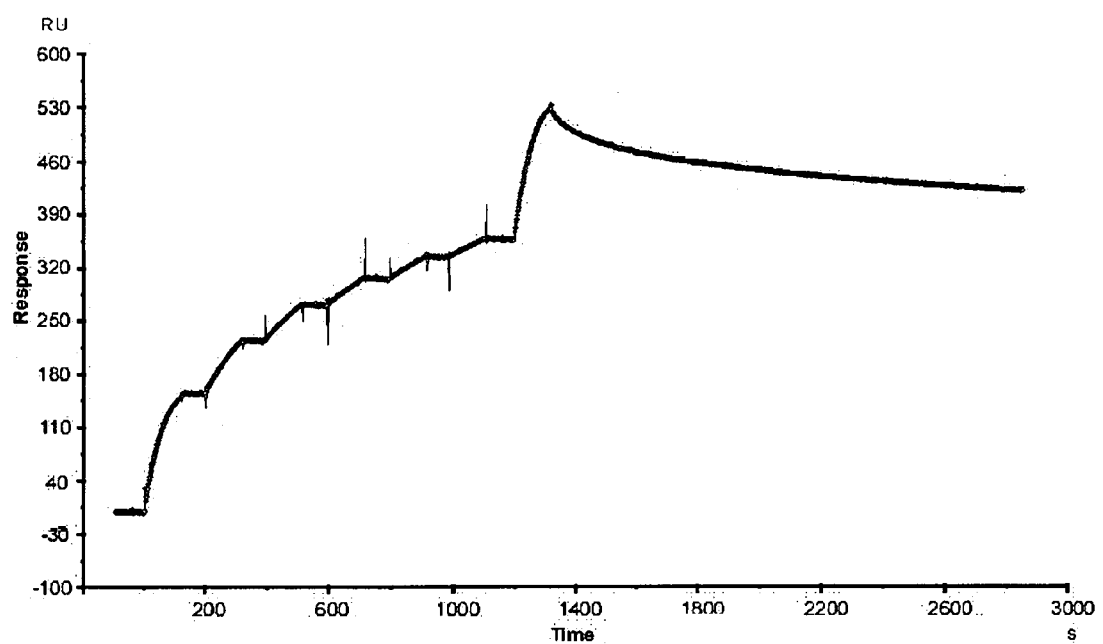

FIG. 3. Biacore competition analysis (BCF2 and scFv 6009F). The first part of the sensorgram (up to 1200 sec), shows the saturation of the sites recognized by BCF2 on Cn2 toxin after 6 injections. The second part shows the binding kinetics of the scFv 6009F at a concentration of 5 nM.

FIG. 4. Human library analysis. 1A. The scFv inserts were amplified from 20 individual clones (lines 1-20). Line C scFv marker (850 bp). 1B. BstN1 fingerprinting of PCR products. Line M 100 bp marker.

Figure 5:
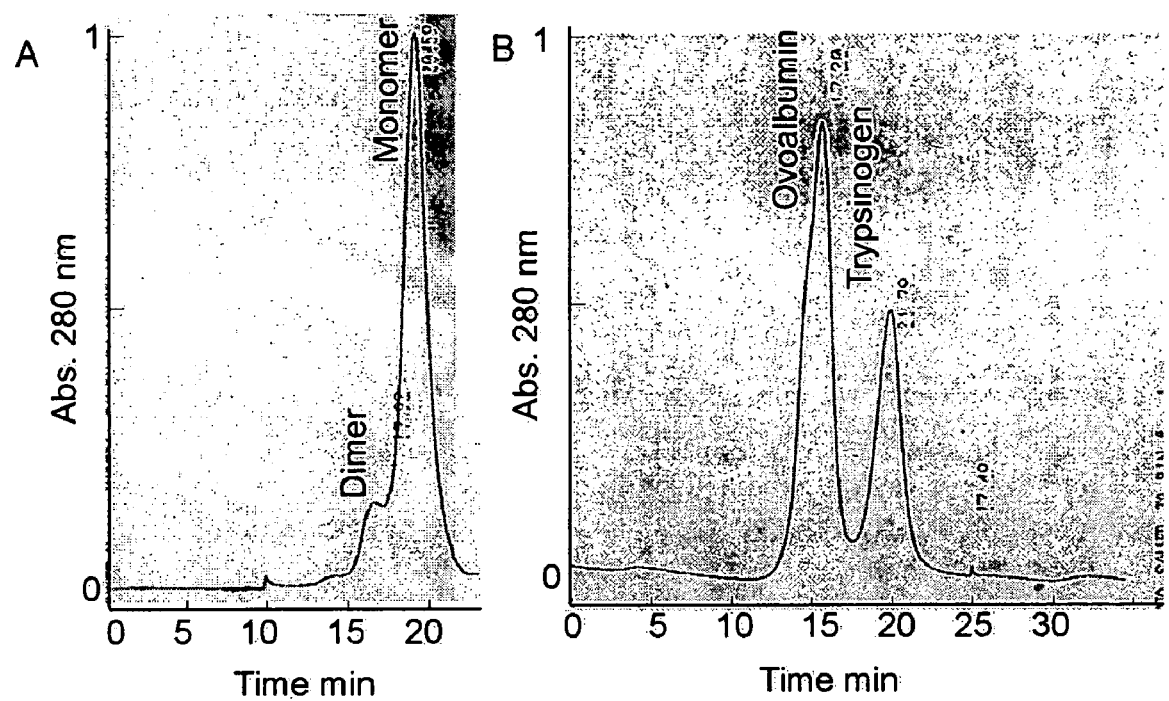

FIG. 5. Purification by molecular exclusion. A) Superdex 75 exclusion chromatography of antibody 6009F after affinity purification on $Ni^{2+}$-agarose. B) Molecular weight standards: ovoalbumin (44 $K_d$), trypsinogen (24 $K_d$). The rate flux was 0.5 ml/min.

Figure 6:
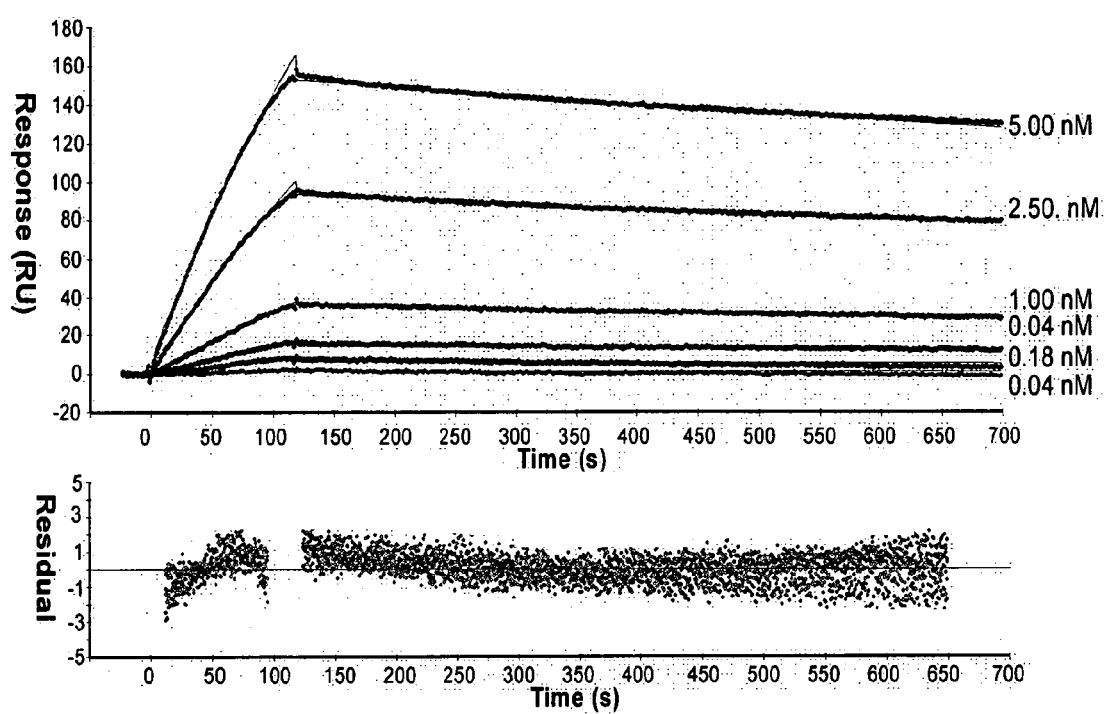

FIG. 6. Affinity determination of scFv 6009F. A) BIACORE binding kinetics to Cn2 toxin. The Langmuir (1:1) binding model was used B) The variation between the theoretical and experimental data (residual values), shows the quality of the fitting.

Figure 7:
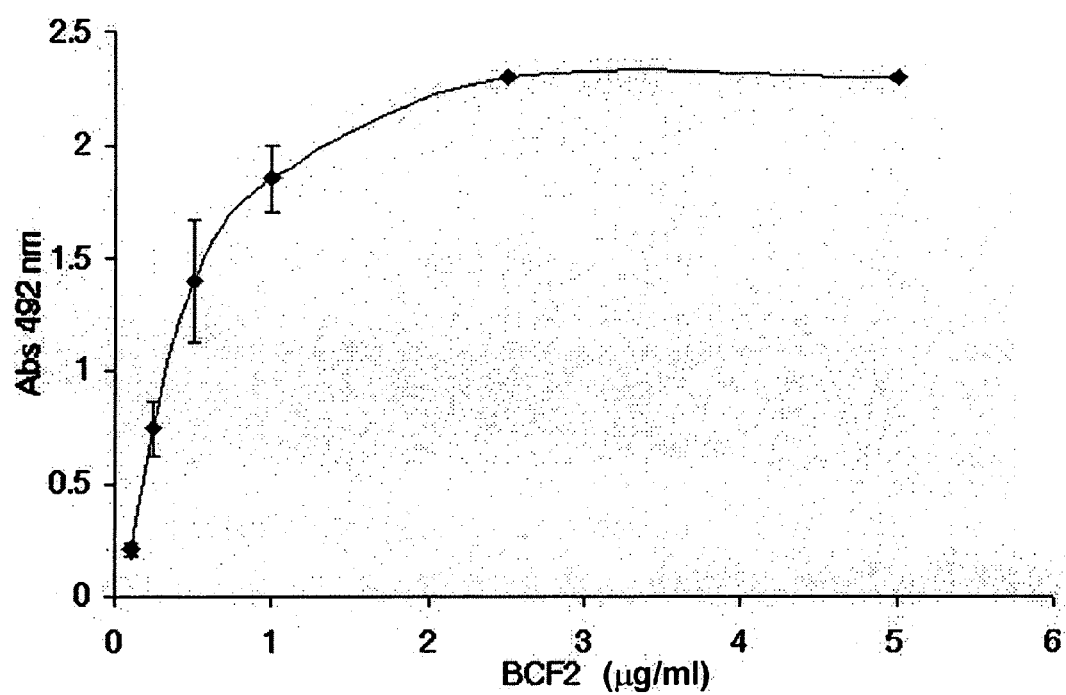

FIG. 7. Competitive ELISA. Plates were coated with scFv 6009F at a concentration of 10 µg/ml overnight, washed and saturated 2 h with BSA (0.5% in PBS 1×). Cn2 toxin was then added (3 µg/ml), incubated 1 h and washed. BCF2 antibody was added at different concentrations (0.1, 0.25, 0.5, 1.0, 2.5 and 5 µg/ml). Detection was performed with a HRP-goat anti-mouse. The vertical lines indicate the standard deviation of the mean, n=3.

Figure 8:
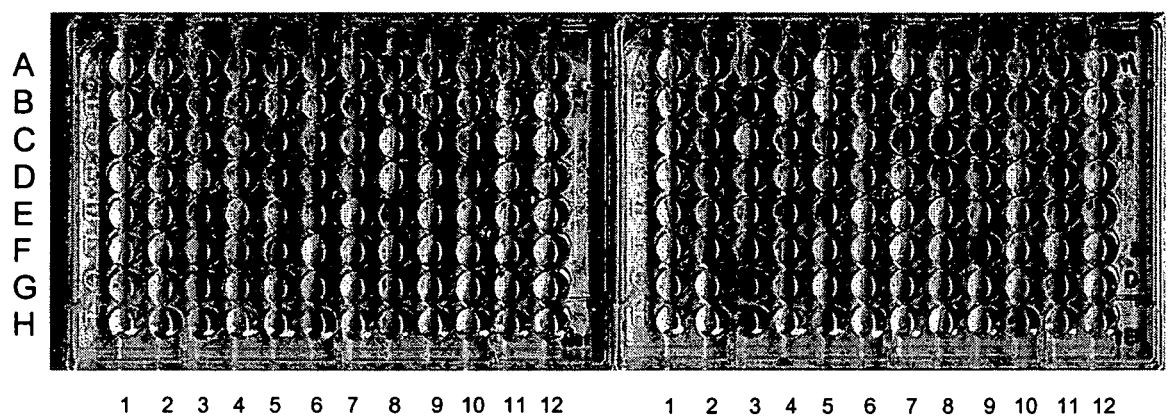

FIG. 8. ELISA of soluble protein of resulting clones from the third directed evolution cycle and third biopanning. The plate of the left are clones obtained with the standard method and the plate of the right are clones obtained with the modified method of the present invention. It is clearly shown that a major number of positive clones and qualitatively with better response were found.

Figure 9:
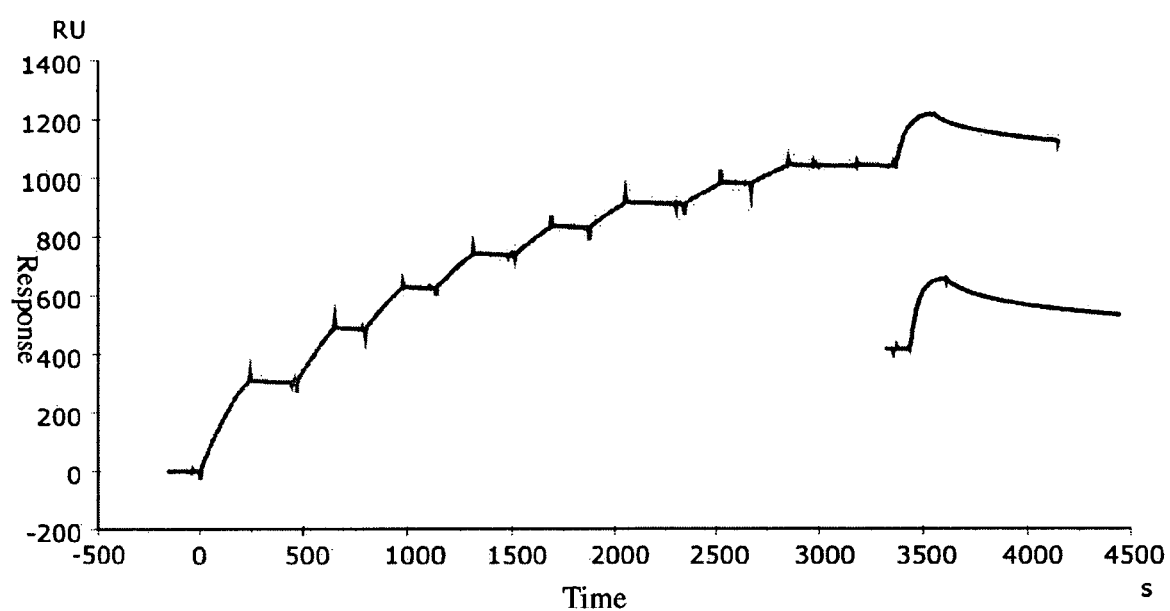

FIG. 9. Biacore competition analysis (Alacramyn, BCF2 and scFv 6009F). The first part of the sensorgram (up to 2900 sec), shows the saturation of the sites recognized by Alacramyn polyclonal antibody fragments on Cn2 toxin after 8 injections. After that it is shown the effect of BCF2 injection (2900 to 3300 sec). Finally, the injection of scFv 6009F (starting at 3300 to the end). The lower curve represents the control binding kinetics of the scFv 6009F (at a concentration of 20 nM) on Cn2 toxin.

Figure 10:
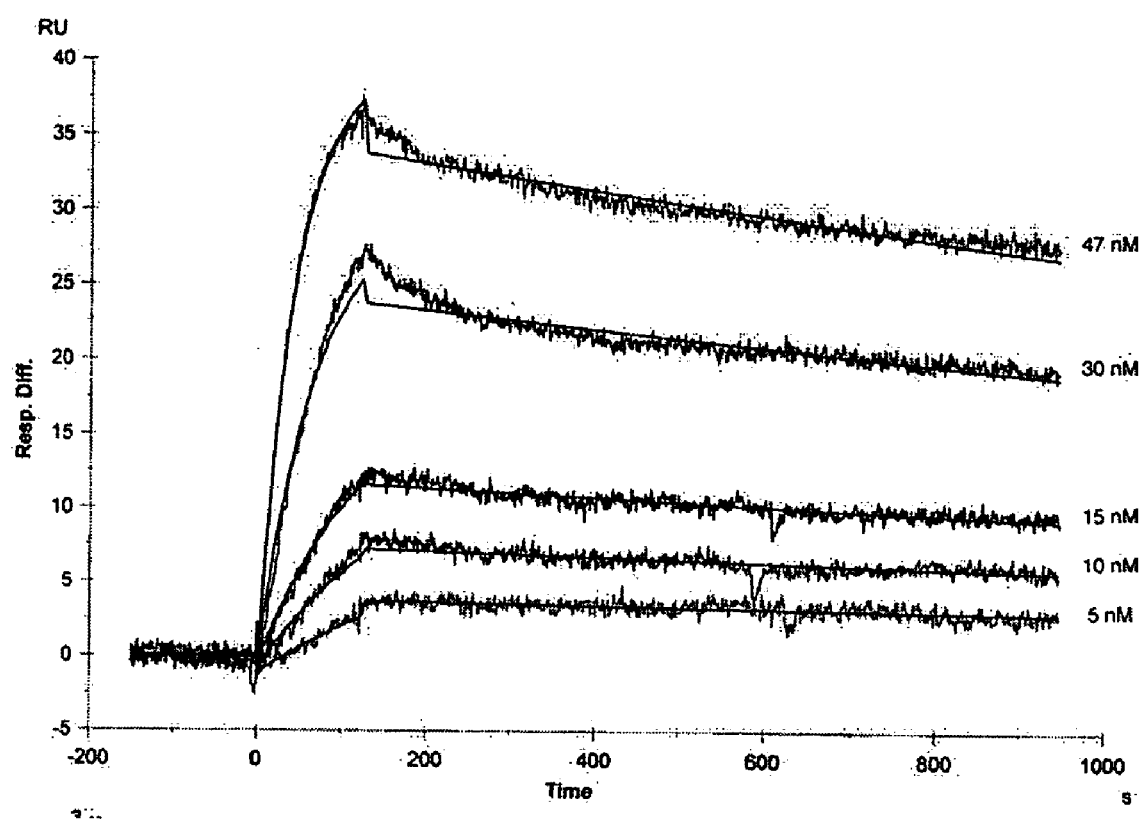

FIG. 10. Affinity determination of scFv 6105F. BIACORE binding kinetics to Cn2 toxin.

Figure 11:
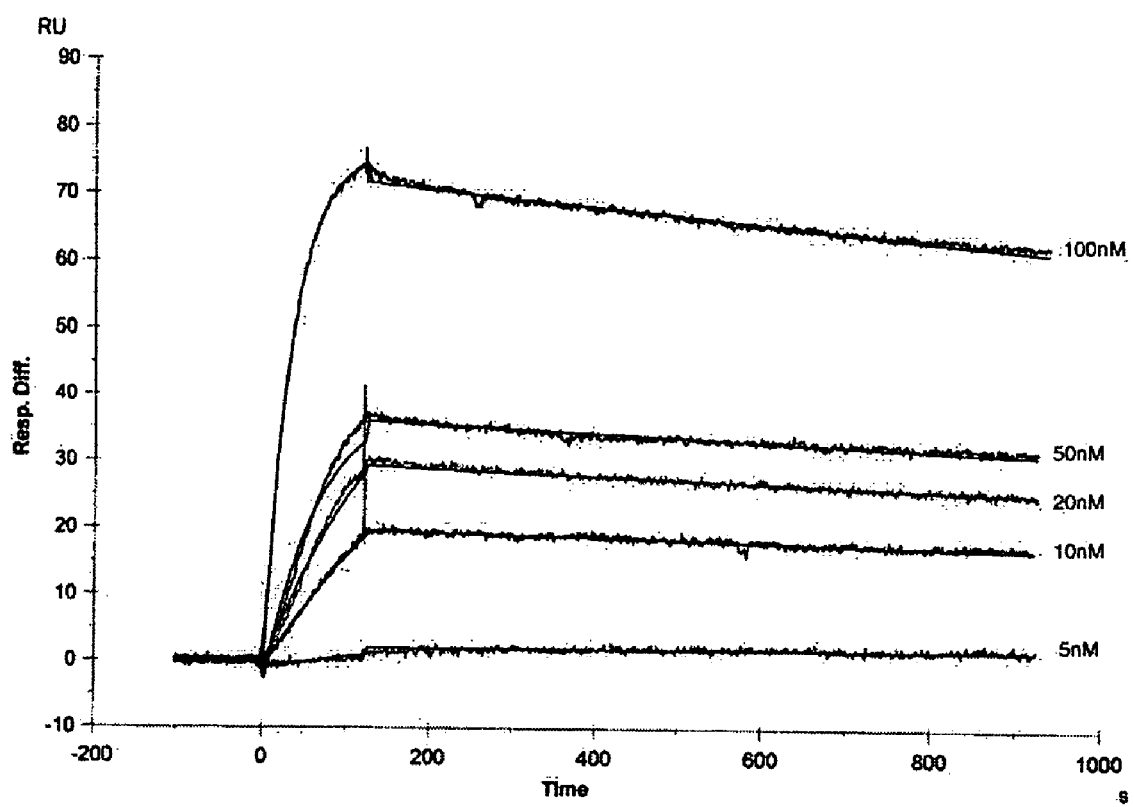

FIG. 11. Affinity determination of scFv 6103E. BIACORE binding kinetics to Cn2 toxin.

BRIEF SUMMARY OF THE INVENTION

Keeping in mind the need for new generation of safer antivenoms and the fact that BCF2 neutralizes both the Cn2 toxin and the whole venom of *C. noxius*, the inventors decided to obtain recombinant human antibodies specific for Cn2 toxin that are able to recognize the toxin and preferably to neutralize it. For this purpose, a human non-immune phage display library of $1.1 \times 10^8$ members was constructed. Two specific scFv (3F and C1), which specifically bind the Cn2 toxin, were selected. The scFv 3F was affinity matured by directed evolution. After three cycles of maturation, several scFv clones were isolated which specifically recognize toxin Cn2 (6F, 610A and 6009F, 6D, 9C, 6003E, 6003G, 6010H, 6011G, 6105F and 6103E). Some of them showed an increment in the $K_d$ of 10.9 fold, 176 fold and 446 fold [from 183 nM (3F) to 16.3 nM (6F), 1.04 nM (610A), 410 pM (6009F), 590 pM (6105F) and 630 pM (6103E)], respectively, as determined by Biacore analysis. All variants were monomeric. Although variants C1, 3F, 6F, 610A, 6D, 9C, 6003E, 6003G, 6010H and 6011G specifically recognized Cn2 did not neutralize the toxin nor the whole venom, while variants 6009F, 6105F and 6103E showed to be capable of neutralizing 2 LD50 of Cn2 toxin or 2 LD50 of whole venom, when a molar ratio of 1:5 toxin:antibody fragment, was used. Variant 6009F recognizes a different epitope than that of BCF2, a murine monoclonal antibody raised against scorpion toxin Cn2, which is capable of neutralizing both toxin Cn2 and the whole venom when tested in mice, and that of Alacramyn, a Mexican polyclonal antibody fragments antivenom from horse. The scFv 6009F is the first reported recombinant human antibody fragment capable of neutralizing scorpion venom. These results pave the way for the generation of safer autologous recombinant neutralizing antivenom against scorpion stings. The antibodies of the present invention can be used as part of a composition to treat those in need of treatment including those already stung by one or more scorpions, particularly *C. noxius* scorpions.

DETAILED DESCRIPTION OF THE INVENTION

I. Definitions

The term "antibody" is used in the broadest sense and specifically covers monoclonal antibodies (including full length monoclonal antibodies), polyclonal antibodies, and antibody fragments.

The term "Antibody fragments" comprises a portion of a full length antibody, generally the antigen binding or variable region thereof. Examples of antibody fragments include Fab, Fab', F(ab')$_2$, and Fv fragments; diabodies; linear antibodies; and particularly single-chain antibody molecules. (scFv).

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short (normally 10 amino acids or less) to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

A "parent antibody" is an antibody comprising an amino acid sequence which is use as starting point for mutagenesis procedures like directed evolution or random mutagenesis (see Neylon, C. (2004). Nucleic Acids Research 32, 1448-1459), or gene shuffling, to generate in one or more mutagenesis cycles antibody variants which differs from such parent antibody comprising one more amino acid alteration in or adjacent to one or more hypervariable regions thereof. The parent polypeptide may comprise a native sequence (i.e. a naturally occurring) antibody (including a naturally-occurring allelic variants) or an antibody with pre-existing amino acid sequence modifications (such as other insertions, deletions and/or substitutions) of a naturally-occurring sequence. Preferably the parent antibody is a human antibody. The parent antibodies of the present invention specifically bind the toxin Cn2 from the venom of scorpion *C. noxius*.

As used herein, "antibody variant" refers to an antibody which was generated by mutagenesis of a parent antibody of the present invention and has an amino acid sequence which differs from the amino acid sequence of said parent antibody. Preferably, the antibody variant comprises a heavy chain variable domain or a light chain variable domain having an amino acid sequence which is not found in nature. Such variants necessarily have less than 100% sequence identity or similarity with the parent antibody. The antibody variants of the present invention specifically bind the toxin Cn2 from the venom of scorpion *C. noxius*.

An "amino acid alteration" refers to a change in the amino acid sequence of a predetermined amino acid sequence. Examples of alterations include insertions, deletions and particularly substitutions. Substitution are referred as the amino acid present in the parent antibody, followed by the position number of said amino acid in the parent antibody (starting by the amino extreme) and followed by the amino acid present which has been substituted in the antibody variant.

"Neutralize or neutralization or a neutralizing antibody" refer to the capacity of an antibody of the present invention to bind to toxin Cn2 and cancel its lethal effect, when administered to a mammal, whether isolated or as part of *C. noxius* venom.

"Treatment" refers to therapeutic treatment. Those in need of treatment include those already stung by one or more scorpions of the species *C. noxius*.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A DNA sequence or fragment is "operably linked" when it is placed into a functional relationship with another nucleic acid sequence or fragment. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase.

As used herein, the expressions "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "effective amount" or "pharmaceutically effective amount" of a compound in unit dose of the composition depends upon a number of factors. Included among these factors are quantities of the other ingredients when used, tolerance of the active ingredient of composition. Effective amount of the active ingredient ranges from about 8% to about 35% by weight based on the total weight of the composition. For compositions against scorpions, the F(ab')$_2$ preparation to be filled in each flask is the amount necessary to neutralize from about 135 to about 220 lethal doses 50% of the venom.

By "pharmaceutically acceptable carrier" is meant solid or liquid filler, diluent or substance which, may be safely used in systemic or topical administration. Depending on the particular route of administration, a variety of pharmaceutically acceptable carriers well known in the art include solid or liquid fillers, diluents, hydrotropes, surface active agents, and encapsulating substances. The amount of carrier employed in conjunction with the F(ab')$_2$ fragments to provide practical quantity of material per unit dose of composition.

Pharmaceutically acceptable carriers for systemic administration that may be incorporated in the composition of the invention include sugar, starches, cellulose, vegetable oils, buffers, polyols and alginic acid. Specific pharmaceutically acceptable carriers are described in the following documents, all incorporated herein by reference: U.S. Pat. No. 4,401,663, Buckwalter et al. issued Aug. 30, 1983; European Patent Application No. 089710, LaHann et al. published Sep. 28, 1983; and European Patent Application No. 0068592, Buckwalter et al. published Jan. 5, 1983. Preferred carriers for parenteral administration include propylene glycol, pyrrolidone, ethyl oleate, aqueous ethanol, and combinations thereof.

Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologues, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 0.5% to about 1%.

II. Obtaining Starting Parent Antibodies

In one embodiment of the present invention, two starting parent antibodies were generated, a human library of antibodies was constructed and phage displayed and two antibodies, C1 (SEQ. ID. NO: 18 for the coding DNA and SEQ. ID. NO: 19 for the amino acidic sequence) and 3F (SEQ. ID. NO: 24 for the coding DNA and SEQ. ID. NO: 25 for the amino acidic sequence), were isolated which specifically recognizes the toxin Cn2 from the venom of scorpion *C. noxius*.

The necessity to generate safer and more efficient antibodies to be used in human therapy has resulted in the development of recombinant antibodies from different sources. Ideally the source should be human itself. As detailed shown in example 1, the human scFv library of the present invention was generated by RT-PCR from total RNA purified from B lymphocytes of human peripheral blood. To avoid as much as possible a bias of antibody variable chain family representation improving the possibility of obtaining at least one scFv with affinity to the Cn2 toxin, each V family of variable regions ($V_H$ or $V_L$), was amplified by independent PCR reactions. In a second step of PCR, the sequence of the linker peptide was added to each individual V family. A PCR overlapping process was performed in order to join both V domains (H and L). Every $V_H$ family was overlapped to every $V_{\kappa\ or\ \nu\lambda}$ families (a total of 72 $V_H$-$V_L$ combinations). The DNA segments encoding the assembled products were fused to pIII gene of PSYN2 phagemid. The scFv library size was $1.2\times10^8$ members. Twenty independent colonies were analyzed by PCR. Eighteen showed the right size and had different restriction patterns when digested with BstNI (FIG. 4). The variability of the 18 different scFvs was confirmed by DNA sequence, which resulted finally in a library of $1.1\times10^8$ variants. We found different combinations of variable domains, which included the majority of V families.

As detailed in example 2, after four rounds of biopanning of the human scFv library against the Cn2 toxin, only two anti-Cn2 scFvs were identified and named scFv 3F (SEQ. ID. NO: 24 for the coding DNA and SEQ. ID. NO: 25 for the amino acidic sequence) and scFv C1 (SEQ. ID. NO: 18 for the coding DNA and SEQ. ID. NO: 19 for the amino acidic sequence) (FIG. 1), corresponding to human immunoglobulins. Clone 3F, comprises a $V_H3$ heavy variable chain (SEQ. ID. NO: 26 for the coding DNA and SEQ. ID. NO: 27 for the amino acidic sequence) and VK3 light variable chain (SEQ. ID. NO: 28 for the coding DNA and SEQ. ID. NO: 29 for the amino acidic sequence), whereas clone C1 comprises a $V_H3$ heavy variable chain (SEQ. ID. NO: 20 for the coding DNA and SEQ. ID. NO: 21 for the amino acidic sequence) and Vλ1 light variable chain (SEQ. ID. NO: 22 for the coding DNA and SEQ. ID. NO: 23 for the amino acidic sequence). These two clones showed to be highly specific to Cn2 despite the fact that Cn2 and the control toxins Cll1 and Cll2 have a high degree of identity (FIG. 2B).

To know if the selected antibodies had the capacity to protect the mice against the toxic effect of Cn2, a neutralization assay was performed. The results revealed that both antibody fragments were unable to protect the mice from the effect of toxin Cn2. The affinity constants of both scFvs were similar, in the range of $10^{-7}$ M which are typical affinity values of the primary immune response (Lefranc, M. P. (2003) *Nucleic Acids Res* 31, 307-10., Foote, J. & Eisen, H. N. (1995) *Proc Natl Acad Sci USA* 92, 1254-6). Clones 3F and C1 showed a fast dissociation despite having good association, which suggest that the antibody fragments do not remain bound to the toxin enough time, to be neutralizing. Several reports have shown that some monomeric scFvs do not neutralize their targets, while their corresponding dimeric scFvs (diabody) do, as a consequence of an increase in their affinity (Aubrey, N., Devaux, C., Sizaret, P. Y., Rochat, H., Goyffon, M. & Billiald, P. (2003) *Cell Mol Life Sci* 60, 617-28., Lantto, J., Fletcher, J. M. & Ohlin, M. (2002) *J Gen Virol* 83, 2001-5). The dimeric forms of both scFvs were constructed but none of the diabodies 3F and C1 was able to neutralize the toxin in the protection assay.

III. Generation of Antibody Variants

In another embodiment of the present invention, antibody 3F was used as parent antibody to generate antibody variants by affinity maturation by directed evolution techniques, but it is possible to generate variants by other mutagenic techniques known to those skilled in the art, like cassette mutagenesis (Stemmer, W. P. C. et al., (1992) *Biotechniques* 14:256-265.; Arkin, A. and Youvan, D. C. (1992) *Proc Natl Acad Sci USA* 89:7811-7815.; Oliphant, A. R. et al., (1986) *Gene* 44:177-183.; Hermes, J. D. et al., (1990) *Proc Natl Acad Sci USA* 87:696-700.; Delagrave et al. (1993) *Protein Engineering* 6: 327-331; Delgrave et al. (1993) *Bio/Technology* 11: 1548-1552; Goldman, E. R. and Youvan D. C. (1992) *Bio/Technology* 10:1557-1561), in which the specific region to be optimized is replaced with a synthetically mutagenized oligonucleotide, gene shuffling and other mutagenesis procedures like directed evolution or random mutagenesis (see Neylon, C. (2004) *Nucleic Acids Research* 32, 1448-1459). The 3F scFv selected from the human non-immune scFv library of the present invention did not have the required affinity and/or stability to be neutralizing as it has been shown for most of the examples of neutralizing antibodies, which have affinities in the nanomolar range and lower (Maynard, J. A., Maassen, C. B., Leppla, S. H., Brasky, K., Patterson, J. L., Iverson, B. L. & Georgiou, G. (2002) *Nat Biotechnol* 20, 597-601., Sawada-Hirai, R., Jiang, I., Wang, F., Sun, S. M., Nedellec, R., Ruther, P., Alvarez, A., Millis, D., Morrow, P. R. & Kang, A. S. (2004) *J Immune Based Ther Vaccines* 2, 5., Devaux, C., Moreau, E., Goyffon, M., Rochat, H. & Billiald, P. (2001) *Eur J Biochem* 268, 694-702). This result was expected, since the library is non-immune and has a medium size. It has been learned that better binders can be selected from bigger libraries. (Sblattero, D. & Bradbury, A. (2000) *Nat Biotechnol* 18, 75-80., Vaughan, T. J., Williams, A. J., Pritchard, K., Osbourn, J. K., Pope, A. R., Earnshaw, J. C., McCafferty, J., Hodits, R. A., Wilton, J. & Johnson, K. S. (1996) *Nat Biotechnol* 14, 309-14., Sheets, M. D., Amersdorfer, P., Finnern, R., Sargent, P., Lindquist, E., Schier, R., Hemingsen, G., Wong, C., Gerhart, J. C., Marks, J. D. & Lindqvist, E. (1998) *Proc Natl Acad Sci USA* 95, 6157-62). The affinity of the toxin Cn2 for the sodium channels present in some cell preparations has been shown to be in the nM range (Garcia, C., Becerril, B., Selisko, B., Delepierre, M. & Possani, L. D. (1997) *Comp Biochem Physiol B Biochem Mol Biol* 116, 315-22., Sitges, M., Possani, L. D. & Bayon, A. (1987) *J Neurochem* 48, 1745-52) These results suggest that an antibody requires an affinity of at least in this range to neutralize the toxin. Taking this into consideration, and with the goal of having a human antibody able to neutralize the toxin Cn2 and the *C. noxius* venom, we decided to mature clones 3F and C1 by directed evolution and phage display. It has been shown that directed evolution of proteins has allowed increasing gradually a particular property of the protein. Usually it is necessary to perform several cycles of evolution in order to obtain the desired level of improvement. Each cycle starts with a parent antibody and generates one or more antibody variants which are expected to have improved kinetics qualities. Any of these resulting antibody variant may be used as a parent antibody for the next cycle of evolution or mutagenesis. As shown in examples 3, 4, 5 and 6, three cycles of evolution were necessary to obtain variants from scFv 3F (6009F, 6105F and 6103E) with an adequate level of affinity to be capable of neutralization. In the first cycle of maturation, the variant 6F (SEQ. ID. NO: 30 for the coding DNA and SEQ. ID. NO: 31 for the amino acidic sequence) was selected, which had an amino acid alteration, the substitution (Ser54Gly), at CDR2 of heavy chain which have a sequence SEQ. ID. NO: 32 for the coding DNA and SEQ. ID. NO: 33 for the amino acidic sequence (and a light chain with sequence SEQ. ID. NO: 34 for the coding DNA and SEQ. ID. NO: 35 for the amino acidic sequence), having an increment of one order of magnitude in the $K_D$ (from 183 nM to 16.8 nM; Table 1). These results show that scFv 6F binds more efficiently to the toxin but it still detaches rapidly, indicating that residue at position 54 plays an important role in the interaction of the antibody with the toxin Cn2 (see example 3 for further details).

In the second cycle of maturation (example 4), the variant clone 610A (SEQ. ID. NO: 36 for the coding DNA and SEQ. ID. NO: 37 for the amino acidic sequence) was selected which have a second amino acid alteration at CDR3 of heavy chain, the substitution Val101Phe (sequences for the heavy and light chains are SEQ. ID. NO: 38 for the coding DNA and SEQ. ID. NO: 39 for the amino acidic sequence of the heavy chain and SEQ. ID. NO: 40 for the coding DNA and SEQ. ID. NO: 41 for the amino acidic sequence for the light chain). This mutation improved both the association constant but more importantly the dissociation constant. This result suggests that residue 109 in the CDR3 of heavy chain also plays an important role in the binding to the toxin. This change could result in a better interaction in terms of an increased area of contact. The accumulated changes at CDR2 and CDR3 in variant clone 610A had a synergistic effect on the affinity constant obtaining an increment of 176 fold (Table 1).

TABLE 1

The Kinetic Parameters of Different Variants of the Present Invention

| Evol. Cycle* | scFv clone | Cumulative Changes* | Position | Kon, $(M^{-1}s^{-1})$ | Koff, $(s^{-1})$ | KD, M | KD improvement* |
|---|---|---|---|---|---|---|---|
|   | 3F    | —         | —         | $7.00 \times 10^4$ | $1.28 \times 10^{-2}$ | $1.83 \times 10^{-7}$ | — |
| 1 | 6F    | Ser 54 Gly | CDR2$V_H$ | $4.93 \times 10^5$ | $8.25 \times 10^{-3}$ | $1.68 \times 10^{-8}$ | 10.89 |
| 2 | 610A  | Ser 54 Gly | CDR2$V_H$ | $6.35 \times 10^5$ | $6.63 \times 10^{-4}$ | $1.04 \times 10^{-9}$ | 175.96 |
|   |       | Val 101 Phe | CDR3$V_H$ |   |   |   |   |
| 3 | 6009F | Ser 54 Gly | CDR2$V_H$ | $7.40 \times 10^5$ | $3.00 \times 10^{-4}$ | $4.10 \times 10^{-10}$ | 446 |
|   |       | Val 101 Phe | CDR3$V_H$ |   |   |   |   |
|   |       | Asn 74 Asp | FW3$V_H$ |   |   |   |   |
|   |       | Thr 152 Ile | FW1$V_\kappa$ |   |   |   |   |
|   |       | Tyr 164 Phe | CDR1$V_\kappa$ |   |   |   |   |
|   |       | Ser 197 Gly | FW3$V_\kappa$ |   |   |   |   |
| 3 | 6105F | Ser 54 Gly | CDR2$V_H$ | $4.8 \times 10^5$ | $2.8 \times 10^{-4}$ | $5.9 \times 10^{-10}$ | 310 |
|   |       | Val 101 Phe | CDR3$V_H$ |   |   |   |   |
|   |       | Asn 74 Asp | FW3$V_H$ |   |   |   |   |
|   |       | Val 141 Ala | FW1$V_L$ |   |   |   |   |
| 3 | 6103E | Ser 54 Gly | CDR2$V_H$ | $3.0 \times 10^5$ | $1.9 \times 10^{-4}$ | $6.3 \times 10^{-10}$ | 290 |
|   |       | Val 101 Phe | CDR3$V_H$ |   |   |   |   |
|   |       | Asn 74 Asp | FW3$V_H$ |   |   |   |   |
|   |       | Thr 106 Ser | CDR3$V_H$ |   |   |   |   |
|   |       | Ala 194 Thr | FW3$V_H$ |   |   |   |   |

*In respect to clone 3F

A third cycle of directed evolution allowed to select the clone 6009F (SEQ. ID. NO: 42 for the coding DNA and SEQ. ID. NO: 43 for the amino acidic sequence) among others. As shown in examples 5 and 6, in this last maturation step, two alternative selection strategies were performed, the standard one and a modified procedure in order to create more stringent conditions intended to select improved variants in their affinity and stability. Those modifications were crucial for the selection of varieties of improved clones. Different strategies with the same purpose have been reported (Kotz, J. D., Bond, C. J. & Cochran, A. G. (2004) Eur J Biochem 271, 1623-9., Zhou, H. X., Hoess, R. H. & DeGrado, W. F. (1996) Nat Struct Biol 3, 446-51., Martin, A., Sieber, V. & Schmid, F. X. (2001) J Mol Biol 309, 717-26., Jung, S., Honegger, A. & Pluckthun, A. (1999) J Mol Biol 294, 163-80). The standard procedure of phage selection gave a low number (2) of positive variants (SEQ. ID. NO: 48, SEQ. ID. NO: 49, SEQ. ID. NO: 50, SEQ. ID. NO: 51, SEQ. ID. NO: 52 and SEQ. ID. NO: 53 for the coding DNA and amino acidic sequence of clone 6D and their $V_H$ and $V_L$, respectively) and (SEQ. ID. NO: 54, SEQ. ID. NO: 55, SEQ. ID. NO: 56, SEQ. ID. NO: 57, SEQ. ID. NO: 58 and SEQ. ID. NO: 59 for the coding DNA and amino acidic sequence of clone 9C and their $V_H$ and $V_L$, respectively) as compared to the more stringent procedure which gave 5 positive variants: 6003E (SEQ. ID. NO: 62, SEQ. ID. NO: 63, SEQ. ID. NO: 64, SEQ. ID. NO: 65, SEQ. ID. NO: 66 and SEQ. ID. NO: 67 for the coding DNA and amino acidic sequence of whole clone and their $V_H$ and $V_L$, respectively), 6003G (SEQ. ID. NO: 68, SEQ. ID. NO: 69, SEQ. ID. NO: 70, SEQ. ID. NO: 71, SEQ. ID. NO: 72 and SEQ. ID. NO: 73 for the coding DNA and amino acidic sequence of whole clone and their $V_H$ and $V_L$, respectively), 6011G (SEQ. ID. NO: 74, SEQ. ID. NO: 75, SEQ. ID. NO: 76, SEQ. ID. NO: 77, SEQ. ID. NO: 78 and SEQ. ID. NO: 79 for the coding DNA and amino acidic sequence of whole clone and their $V_H$ and $V_L$, respectively), 6010H (SEQ. ID. NO: 80, SEQ. ID. NO: 81, SEQ. ID. NO: 82, SEQ. ID. NO: 83, SEQ. ID. NO: 84 and SEQ. ID. NO: 85 for the coding DNA and amino acidic sequence of clone and their $V_H$ and $V_L$, respectively) and clone 6009F. The number of nucleotide changes per variant in the selected clones from the two procedures was different. The DNA sequence of clone 6009F showed two silent mutations and four amino acid alterations with respect to clone 610A (Table 1). One of these amino acid alterations occurred at framework 3 of heavy chain, the substitution Asn74Asp, which have a sequence SEQ. ID. NO: 44 for the coding DNA and SEQ. ID. NO: 45 for the amino acidic sequence, and the other 3 substitutions at light chain which have a sequence SEQ. ID. NO: 46 for the coding DNA and SEQ. ID. NO: 47 for the amino acidic sequence. Two of them (Thr152Ile and Ser197Gly) occurred at frameworks 1 and 3 respectively and the third one (Tyr164Phe), at CDR1 (Table 1). The kinetic parameters shown in Table 1 reveal that both kinetic constants were improved about 2 fold as compared to clone 610A, resulting in an affinity constant $K_d$ of 410 pM.

The DNA sequence of clone 6105F showed one silent mutation and only two amino acid alterations with respect to clone 610A (Table 1). One of these amino acid alterations (Asn74Asp) occurred at framework 3 of heavy chain, which have a sequence SEQ. ID. NO: 88 for the coding DNA and SEQ. ID. NO: 89 for the amino acidic sequence, and the other substitution (Ala141Val) at framework 1 of the light chain, which have a sequence SEQ. ID. NO: 90 for the coding DNA and SEQ. ID. NO: 91 for the amino acidic sequence. The kinetic parameters shown in Table 1 reveal that both kinetic constants were improved about 1.5-2 fold as compared to clone 610A, resulting in an affinity constant $K_d$ of 590 pM.

The DNA sequence of clone 6103E showed one silent mutation and three amino acid alterations with respect to clone 610A (Table 1). Two of them (Asn74Asp) occurred at the heavy chain, one at framework 3, and the other (Thrr106Ser) occurred at CDR3 of the heavy chain, which have a sequence SEQ. ID. NO: 94 for the coding DNA and SEQ. ID. NO: 95 for the amino acidic sequence. The third substitution (Ala192Thr) occurred at the framework3 of light chain, which have a sequence SEQ. ID. NO: 96 for the coding DNA and SEQ. ID. NO: 97 for the amino acidic sequence. The kinetic parameters shown in Table 1 reveal that both kinetic constants were improved about 1.5-2 fold as compared to clone 610A, resulting in an affinity constant $K_d$ of 630 pM.

It has been suggested that changes at CDRs are the most important to improve the affinity for the antigen (Cowell, L. G., Kim, H. J., Humaljoki, T., Berek, C. & Kepler, T. B. (1999) *J Mol Evol* 49, 23-6., Gonzalez-Fernandez, A., Gupta, S. K., Pannell, R., Neuberger, M. S. & Milstein, C. (1994) *Proc Natl Acad Sci USA* 91, 12614-8). However, recently it has been shown that changes at frameworks are determinant to improve not only affinity and stability (Daugherty, P. S., Chen, G., Iverson, B. L. & Georgiou, G. (2000) *Proc Natl Acad Sci USA* 97, 2029-34) but also the level of expression in cells (Graff, C. P., Chester, K., Begent, R. & Wittrup, K. D. (2004) *Protein Eng Des Sel* 17, 293-304). A similar phenomenon was observed during the maturation of clone 3F to variant clone 6009F, because scFv 6009F accumulated 3 changes at CDRS and 3 changes at the frameworks, similar considerations apply for variants 6105F and 6103E in which mutations occurred both at CDRs and Frameworks. The chromatographic elution profile of the antibody 6009F, showed a main peak corresponding to a monomeric form (FIG. 5). We surmised that the changes in the frameworks contributed to reach a better affinity and functional stability. The analysis of affinity measurements [Table 1. and FIG. 6], revealed that the clone 6009F, had a $K_d$ of 410 pM, which is comparable to affinities of other neutralizing antibodies of scorpion toxins (Aubrey, N., Devaux, C., Sizaret, P. Y., Rochat, H., Goyffon, M. & Billiald, P. (2003) *Cell Mol Life Sci* 60, 617-28). While clone 6105F had a $K_d$ of 590 pM and clone 6103E had a $K_d$ of 630 pM, which are comparable to affinities of other neutralizing antibodies of scorpion toxins too. The global synergistic improvement in the kinetic parameters with respect to 3F scFv shown in Table 1 leads to a 446 fold increment in $K_d$ for clone 6009F, while it leads to 310 for 6105F and 290 for 6103E.

It is important to emphasize that all three variants (6009F, 6105F and 6103E) contain a common mutation (Asn74Asp), which could be a key reisdue to improve the affinity and stability required to neutralize Cn2 toxin.

As it shall be clear for those skilled in the art, other antibodies can be obtained by different combinations of the $V_H$(SEQ. ID. NO: 20, SEQ. ID. NO: 26, SEQ. ID. NO: 32, SEQ: ID. NO: 38, SEQ. ID. NO: 44, SEQ. ID. NO: 50, SEQ. ID. NO: 56, SEQ. ID. NO: 64, SEQ. ID. NO: 70, SEQ. ID. NO: 76, SEQ. ID. NO: 82, SEQ. ID. NO: 88 and SEQ. ID. NO: 94) and $V_L$(SEQ. ID. NO: 22, SEQ. ID. NO: 28, SEQ. ID. NO: 34, SEQ. ID. NO: 40, SEQ. ID. NO: 46, SEQ. ID. NO: 52 SEQ. ID. NO: 58, SEQ. ID. NO: 66, SEQ. ID. NO: 72, SEQ. ID. NO: 78, SEQ. ID. NO:84, SEQ. ID. NO:90 and SEQ. ID. NO: 96) fragments. Accordingly, as long as these other antibodies retain the specific binding capacity to Cn2 toxin, they shall be considered within the scope of the present invention and thus shall be included in the term "antibodies of the present invention".

Similarly, it is clear for those skilled in the art that any of the antibodies of the present invention can be used as parent antibodies to generate further antibody variants. As long as these new antibody variants retain the specific binding capacity to Cn2 toxin, they shall be considered within the scope of the present invention and thus shall be considered functionally equivalents of the antibodies of the present invention.

Additionally, the $V_H$(SEQ. ID. NO: 20, SEQ. ID. NO: 26, SEQ. ID. NO: 32, SEQ: ID. NO: 38, SEQ. ID. NO: 44, SEQ. ID. NO: 50, SEQ. ID. NO: 56, SEQ. ID. NO: 64, SEQ. ID. NO: 70, SEQ. ID. NO: 76, SEQ. ID. NO: 82, SEQ. ID. NO:88 and SEQ. ID. NO: 94) and $V_L$(SEQ. ID. NO: 22, SEQ. ID. NO: 28, SEQ. ID. NO: 34, SEQ. ID. NO: 40, SEQ. ID. NO: 46, SEQ. ID. NO: 52 SEQ. ID. NO: 58, SEQ. ID. NO: 66, SEQ. ID. NO: 72, SEQ. ID. NO: 78, SEQ. ID. NO:84, SEQ. ID. NO:90, and SEQ. ID. NO: 96) antibody fragments clones can be used to generate not only the scFv antibody format but also any of the Fab, F(ab')$_2$ or even full length monoclonal antibody formats by the operably linked addition of part or the whole of the constant regions of the light and heavy chains, to be used in different applications.

IV. Expression of the Antibodies of the Present Invention

In general, antibodies of the invention may be produced by transformation of a suitable host cell with all or part of an antibody-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. An antibody of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.). The method of transformation or transfection and the choice of expression vehicle will depend on the host system selected and are well known to those skilled in the art. Expression vehicles may be chosen for instance from those provided, e.g., in Cloning Vectors: A Laboratory Manual (P. H. Pouwels et al). As shall be obvious for those skilled in the art, it will be important that the DNA sequences of the antibodies of the present invention are operably linked to the expression control sequences of the vector of the chosen expression system.

A variety of expression systems exists for the production of the antibodies of the present invention. Such vectors include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Particularly, for the purpose of providing enough material for the tests of the present invention, the antibodies were cloned in the vector PSYN1 and expressed in *E. coli* TG1 as detailed in example 7. But one particular bacterial expression system for antibody production is the *E. coli* pET expression system (Novagen, Inc., Madison, Wis.). According to this expression system, DNA encoding an antibody is inserted into a pET vector in an orientation designed to allow expression. Since the gene encoding such an antibody is under the control of the T7 regulatory signals, expression of the antibody is achieved by inducing the expression of T7 RNA polymerase in the host cell. This is typically achieved using host strains which express T7 RNA polymerase in response to IPTG induction. Once produced, recombinant antibody is then isolated according to standard methods known in the art.

Another bacterial expression system for antibody production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant antibody of the invention is expressed, it is isolated, e.g., using affinity chromatography. In one example, the antibodies were purified by $Ni^{2+}$-NTA affinity chromatography (QIAGEN, Germany) (see example 7). In another example, toxin Cn2 may be attached to a column and used to isolate the recombinant antibodies. Lysis and fractionation of antibody-harboring cells prior to affinity chromatography may be performed by standard methods.

Once isolated, the recombinant antibody can, if desired, be further purified, e.g., by high performance liquid chromatography (see, e.g., Fisher, Laboratory Techniques In Biochemistry And Molecular Biology, eds., Work and Burdon, Elsevier, 1980), or by gel filtration chromatography on a Superdex™ 75 column (Pharmacia Biotech AB, Uppsala, Sweden) (see example 7).

Antibodies of the invention, can also be produced by chemical synthesis (e.g., by the methods described in Solid Phase Peptide Synthesis, 2 nd ed., 1984 The Pierce Chemical Co., Rockford, Ill.).

V. Comparing 6009F Antibody to BCF2 Monoclonal Antibody and Horse Polyclonal Antibody Fragments $F(ab')_2$ In order to know if the epitope recognized by clone 6009F was the same as the one recognized by BCF2, a displacement test using the Biacore was performed (FIG. 3). As already mentioned, the monoclonal antibody BCF2 neutralizes toxin Cn2. The results showed that the F6009 antibody binds to Cn2 toxin in a site (epitope) different as the one recognized by monoclonal antibody BCF2. These results were confirmed by a competitive ELISA (FIG. 7). See example 9 for major detail. It is important to mention that despite of being relatively small (66 amino acid residues), the toxin Cn2 seems to have several distinct epitopes (Zamudio, F., Saavedra, R., Martin, B. M., Gurrola-Briones, G., Herion, P. & Possani, L. D. (1992) *Eur J Biochem* 204, 281-92).

Some additional commentaries can be mentioned about the epitopes recognized by BCF2 and scFv 6009F. A dimeric scFv derived from BCF2 with an affinity constant of 75 pM (Juarez-Gonzalez, V. R. Riano-Umbarila, L. Quintero-Hernandez, V. Olamendi-Portugal, T. Ortiz-Leon, M. Ortiz, E. Possani, L. D. Becerril, B. (2005) *J Mol Biol* 346, 1287-1297.), was capable of neutralizing 1 DL50 of Cn2 toxin at a molar ratio 1:10 (toxin:scFv). However, a mild envenomation symptom was observed. These results suggest a differential effect of the toxin on its target (sodium channels) depending on the blocked epitope. This could explain why the clone 6009F with a lower affinity (200 pM) and at a lower molar ratio (1:5), was capable to completely neutralize 2 $DL_{50}$ of the toxin without any symptom of intoxication observed. This indicates that the antibody 6009F is more efficient to block the interaction of the toxin with the channel as compared to matured scFv of BCF2; therefore the epitope recognized by 6009F seems to be more relevant than the recognized by BCF2. Similar results have been reported in other systems (Amersdorfer, P., Wong, C., Smith, T., Chen, S., Deshpande, S., Sheridan, R. & Marks, J. D. (2002) *Vaccine* 20, 1640-8).

Furthermore, as detailed in example 9, a displacement test using the Biacore was performed with scFv 6009F and a commercially available anti scorpion antivenom, Alacramyn from Instituto Bioclon S. A. de C. V. (Mexico), a polyclonal pool of horse antibody fragments $(F(ab')_2)$ to determine if the epitope recognized by the scFv 6009F was also recognized by any of the antibody fragments present in the antivenom. The results (FIG. 9) showed that the epitope recognized by the scFv 6009F is totally different from those recognized by any of the antibody fragments present in the commercial antivenom. This observation suggest that the epitopes of the toxin Cn2 were not exactly the same when it was exposed to the naturally occurring immune system of the animals (mouse in the case of BCF2 or horses in the case of Alacramyn) than when it was exposed to our in vitro immune system.

VI. Use of the Antibodies of the Present Invention as Antivenoms

As shown in example 8, in contrast to variants 6F and 610A, antibody variant 6009F is able to neutralize toxin Cn2 (it is capable of neutralizing 2 LD50 of Cn2 toxin when a molar ratio of 1:5 is used, or 2 LD50 of whole venom). Accordingly, it can be used as a component of a pharmaceutical composition to treat animal and people in need of such treatment as consequence of being stung by a scorpion, particularly if the scorpion is determined to be *Centruroides noxius*. The pharmaceutical composition can comprise additionally other antibodies for instance polyclonal antibodies from horse or goat raised against scorpion venoms or other human or humanized antibodies against other toxins from *C. noxius* venom or against other toxin from the venom of different scorpions. The composition can additionally comprise several pharmaceutically acceptable carriers.

A method to treat an individual in need of such treatment, for instance after being stung by a scorpion, specially if the scorpion is a *C. noxius* scorpion, comprises the parenteral administration of said pharmaceutical composition which comprises the antibody 6009F of the present invention.

VII. Use of the Antibodies of the Present Invention as Part of a Solid Phase

The antibodies of the present invention, particularly 6009F can be used in a composition comprising the antibodies of the present invention adhered to a solid phase substrate such as glass (e.g. controlled pore glass), polysaccharides (e.g., agarose), polyacrylamides, polystyrene, polyvinyl alcohol, silicones, sepharose, carboximetil cellulose and nitrocellulose, in such a way that the composition can bind the Cn2 toxin, whether free or as part of *C. noxius* venom or as a contaminant of a blood or serum sample. In certain embodiments, depending on the context, the solid phase can comprise the well of an assay plate; in others it is a purification column (e.g. an affinity chromatography column) and in others it is part of a diagnostic kit. This term also includes a discontinuous solid phase of discrete particles, such as those described in U.S. Pat. No. 4,275,149. Then another embodiment of the present invention relates to a solid phase that comprises the antibodies 3F, 6F, 610A or preferably 6009F, 6105F or 6103E.

VIII. Use of Antibodies and or Solid Phase of the Present Invention in a Diagnostic System There are some immunodiagnostic techniques available in the art, which commonly use specific antibodies to detect the presence of a particular antigen in a sample. For instance the Enzymatic Linked Immuno System Assay (ELISA) and Immunochromatographic Assay (hereinafter referred to as "ICA").

ICA is also referred to as "rapid test" due to its rapidity and simplicity. In such assay, tracer antibody molecules conjugated with gold particles bind to a particular antigen contained in a serum sample, after which the formed complexes pass through microspores of nitrocellulose (NC) membrane in terms of capillary phenomenon. The complexes finally bind to capture antibodies immobilized on the inner surface of microspore of the NC membrane and develop color of a positive line, whereby determining easily the existence of a particular antigen in the serum sample with the naked eye.

As noted above, the ICA, owing to simplicity of procedure and rapidity of the running result, has been widely used for the detection of various analytes such as antigens (Sato, K. et al. (1996) *J Clin Microbiol* 34, 1420-1423).

There are two major constituents in the ICA kit. One is the nitrocellulose membrane which has two invisible lines on the surface and the other is a glass fiber filter containing antibody-gold particle conjugates in a dry state on the surface. Two kinds of antibodies, that is, the monoclonal antibody being specific to antigen to be detected and Goat anti-mouse IgG, are immobilized on the lower line and the upper line of the nitrocellulose membrane, respectively.

A sample is added to a sample well of the ICA kit and then the antibody-gold particle conjugates on the surface of the NC membrane in a dry state are re-hydrated and then bound to antigens in the serum sample, after which the formed complexes pass through microspores of the NC membrane in terms of capillary phenomenon.

Thereinafter, the antigens of the complexes are reacted with the monoclonal antibodies immobilized on the lower line, resulting in developing a color. In addition, the upper line develops a color because the Goat anti-mouse IgG immobilized on the upper line may react with the antibody-gold particle conjugates although no antigen is present, thus the upper line always develops a color in each run of the test and may serve as a control line. In other words, when antigens exist in the serum sample, both the positive line and the control line of the ICA kit become visible. However, only the control line becomes visible, when no antigen is present.

The antibodies of the present invention, preferably 6009F, 6105F or 6103E, whether free or incorporated to the above described solid phase, can be used as part of a diagnostic kit to detect the presence or absence of the toxin Cn2 in a sample. They can be used as part of an ELISA or as part of an ICA. Polyclonal antibodies Goat anti-mouse shall be substituted by polyclonal antibodies anti-human, for instance Goat anti-human in order to use the antibodies of the present inventions.

Accordingly, another embodiment of the present invention relates to an immunodiagnostic kit comprising antibodies 3F, 6F, 610A or preferably 6009F, 6105F or 6103E. The Immunodiagnostic kit can be an ELISA or an Immunochromatographic Assay.

IX. The Use of Antibody 6009F to Treat the Envenomation with *C. noxius* Venom

Since antibody variant 6009F neutralizes the lethal effect of toxin Cn2 and whole *C. noxius* venom, as it is clearly shown in example 8, antibody variant 6009F and/or any functionally equivalent variants thereof (i.e. antibody variants of 6009F that neutralize the lethal effect of toxin Cn2 and *C. noxius* whole venom) may be used as part of a pharmaceutical composition to treat a patient that has been stung a scorpion, particularly if the scorpion is *C. noxius*. The pharmaceutical composition may include other antibodies like those horse polyclonal F(ab')$_2$ fragments already used as antivenoms. In this case the addition of antibody 6009F and/or functionally equivalent variants thereof is to strengthen its neutralizing effect, particularly against the *C. noxius* venom. Optionally, the pharmaceutical composition may also include a pharmaceutically acceptable carrier like those already mentioned.

Accordingly, another embodiment of the present invention is related to a pharmaceutical composition comprising the antibody 6009F, 6105F or 6103E and/or any functionally equivalent variant thereof to treat envenomation by a scorpion, particularly *C. noxius* scorpion.

In another embodiment, the present invention relates to a method to treat a mammal in need of such treatment, particularly patients who had been stung by a scorpion, especially if scorpion is *C. noxius*, comprising the step of administering a pharmaceutically effective amount of a pharmaceutical composition comprising the antibody variant 6009F, 6105F or 6103E and/or functionally equivalent variants thereof. The pharmaceutical composition can be administered locally and/or systemically through the conventional routes such as the intravenous, subcutaneous, intramuscular, intravaginal, intraperitoneal, intranasal, oral or other mucous routes to protect the patient against the lethal effect of toxin Cn2 of the venom of scorpions *Centruroides*.

X. Modified Biopanning Method for the Selection of Improved Clones

Standard biopanning method for selection of the affinity improved phage-antibody variants from a library obtained by a mutagenesis cycle generally include the steps of: 1) incubating the library in the presence of the target binding antigen, previously adhered to a solid phase like the immunotube (Nunc; Maxisorp), during a time to allow specific clones to bind to the immobilized objective antigen; 2) Extensively washing with PBS-Tween20 (1×, 0-1%) and PBS to remove nonspecific phages-antibodies, and 3) recovering the bound phage-antibodies by the addition of either weak acid or base solution or a suspension of cells, particularly the cell strain the one that is the target of the phage used to phage-display the antibody repertory. Several rounds are commonly carried out to increase the number of positive clones to be screened. The resulting mutant clones of these standard procedures in general slightly improve the affinity of the clone. Commonly, standard procedures to evolve antibodies include several rounds of mutagenesis cycles followed by biopanning, before obtaining a satisfactory affinity improved clone.

In order to select antibody variants improved not only in its affinity but in its stability too, the inventors of the present invention have modified the standard procedure. Those modifications were crucial for the selection of a variety of improved antibody variants of clone 3F.

It is well know to those in the art, that the increase of the temperature during the incubation period increase the speed to which the bonds between the antibodies and the target antigen are formed and dissolved, helping the selection of strongly bond antibodies and the washing of weakly bond antibodies. Similarly, an increase in the time period of incubation tends to help to select strongly bond antibodies.

Additionally, it is a common practice to use weak acid or weak bases solutions to recover the bond antibodies. In the present invention, the inventors decided to take advantage of the above mentioned increase in the temperature and time of the period of incubation together with a diminution in the amount of the target antigen used to coat the immunotube (to increase the stringency of the biopannig), and additionally, they took the risk of detach the antibodies recovered through the use of a weak base and seek if there were any antibody that remain bond to the target antigen in the immunotube. Contrary to what it was expected, as is shown in examples 5 and 6, after a further recovery step with cells suspension, several antibodies were recovered from the immunotube. Those antibodies were improved in both affinity and stability, in respect to the parent antibody 610A, as compared with the antibodies recovered using the standard procedures which were only slightly improved in its affinity.

The method of the present invention to select antibody variants improved in affinity and stability, from a mutagenized antibody library comprises the steps of:

1) Incubating the library in the presence of the target binding antigen, previously adhered to a solid phase like the immunotube (for instance Nunc; Maxisorp), during a time to allow specific variants to bind to the immobilized target antigen at a temperature of at least (30° C.), preferably 37° C. and for a period of at least 5 Hr.

2) Extensively washing with PBS-Tween20 (1×, 0.1%) and PBS to remove nonspecific phages-antibodies, 3) Washing with a weak acid or weak base solution (for instance 100 mM triethylamine) to remove the nonspecific and less stable or low binding phage-antibodies, follow by a neutralization; and 4) Recovering the bound phage-antibodies by the addition of a suspension of cells, particularly the cell strain that is the target of the phage used to phage-display the antibody repertory.

Optionally, the method can comprise an additional step of incubating the library in the presence of blocking agents before to the biopanning in order to eliminate as much as possible unspecific clones. The blocking agents are well known to those in the art and can include BSA, milk or gelatin for instance.

When used this modified method in comparison to the standard method to select the mutated clones, after a mutagenesis cycle of antibody variant 610A, the standard method of phage selection gave a lower number of positive variants (2 with medium signal of a total 88) as compared to the more stringent modified method (5 with high signal of a total 88) see FIGS. 8 and 2 more in a further procedure (2 with high signal of a total 88). The number of nucleotide changes in the selected clones from the two procedures was different. The clones selected from the standard procedure had a lower number of changes (usually one), while using the stringent strategy, the selected clones showed 2-6 changes. The affinity and stability of these 7 (5+2) clones was better than those of the 2 clones recovered by the standard method.

XI. The scFv 6009F Recognizes a Different Epitope than BCF2 Monoclonal Antibody or the Whole Polyclonal Horse Antivenom As detailed in example 9, the scFv 6009F recognized a different epitope as shown by a BIOCORE competitive analysis against monoclonal BCF2 (FIG. 3). It was also confirmed by competitive ELISA (FIG. 7). Furthermore, whole polyclonal horse antivenom did not contain antibodies that compete with scFv 6009F for the same epitope as shown by a BIOCORE analysis (FIG. 9).

A. Materials and Methods

Antigens. The toxin Cn2 (formerly named 11-9.2.2), was purified from venom obtained by electric stimulation of scorpions of the species *Centruroides noxius* Hoffmann. The venom was purified by Sephadex G-50 gel filtration and cation exchange chromatography (Zamudio, F., Saavedra, R., Martin, B. M., Gurrola-Briones, G., Herion, P. & Possani, L. D. (1992) *Eur J Biochem* 204, 281-92). The other toxins used (Cll1, (Ramirez, A. N., Martin, B. M., Gurrola, G. B. & Possani, L. D. (1994) *Toxicon* 32, 479-90), Cll2 (Alagon, A. C., Guzman, H. S., Martin, B. M., Ramirez, A. N., Carbone, E. & Possani, L. D. (1988) *Comp Biochem Physiol B* 89, 153-61), Pg 5, Pg 7, Pg 8, (unpublished data), FII (toxic fraction II from *Centruroides limpidus limpidus*), (Alagon, A. C., Guzman, H. S., Martin, B. M., Ramirez, A. N., Carbone, E. & Possani, L. D. (1988) *Comp Biochem Physiol B* 89, 153-61), were obtained by the same procedure, from venoms of the species *Centruroides limpidus limpidus* (Cll) and *Parabuthus granulatus* (Pg).

Plasmid PSYN1. This vector allows the expression of the cloned segment under the control of lac promoter. The expressed product contains a Cmyc tag and a hexa His tag at the carboxyl terminus. (Schier, R., Marks, J. D., Wolf, E. J., Apell, G., Wong, C., McCartney, J. E., Bookman, M. A., Huston, J. S., Houston, L. L. & Weiner, L. M. (1995) *Immunotechnology* 1, 73-81., Bai, J., Sui, J., Zhu, R. Y., Tallarico, A. S., Gennari, F., Zhang, D. & Marasco, W. A. (2003) *J Biol Chem* 278, 1433-42).

Plasmid PSYN2. This vector allows the display of the cloned segment under the control of lac promoter fused to the gene III (which codes for pIII). The expressed product contains a Cmyc tag and a stop codon (amber) which allows expressing the free scFv in a suppressor strain.

Variable Domain PCR Amplifications

A GeneAmp PCR thermo-cycler (PERKIN ELMER 9600, Norwalk, USA), was used for PCR reactions. The conditions for the amplifications were: three min of denaturation at 95° C., followed by 30 cycles at 95° C. for 1 min, 55° C. for 1 min and 72° C. for 1 min, with a final extension cycle at 72° C. for 10 min. PCR products were purified with a QIAquick PCR purification kit (QIAGEN, Inc., Valencia, Calif., USA).

Standard Biopanning Method of Anti-Cn2 scFv

Standard Biopanning was performed as described in (Marks, J. D., Hoogenboom, H. R., Bonnert, T. P., McCafferty, J., Griffiths, A. D. & Winter, G. (1991) *J Mol Biol* 222, 581-97) with some modifications as follows: One ml of the library (1×1013 phage-antibodies) was incubated in the presence of different blocking agents (BSA or gelatin) before to the biopanning in order to eliminate as much as possible unspecific clones. Substracted library was poured into an immunotube (Nunc; Maxisorp) previously coated over night (O/N) with 1 ml of toxin Cn2 at 50 μg/ml in NaHCO3 buffer, pH 9.4 at 4° C. Extensive washings were performed to remove nonspecific phages (20 washes with PBS 1× with Tween20 0.1% and 20 washes with PBS). The bound phage-antibodies were recovered by the addition of 1 ml of TG1 cells of a mid-log phase (OD600=0.7) culture (Lou, J., Marzari, R., Verzillo, V., Ferrero, F., Pak, D., Sheng, M., Yang, C., Sblattero, D. & Bradbury, A. (2001) *J Immunol Methods* 253, 233-42., Sblattero, D. & Bradbury, A. (2000) *Nat Biotechnol* 18, 75-80) After four rounds of panning, single phage-antibody clones were randomly picked and screened for specific binding to Cn2 by ELISA.

ELISA screening of single phage display antibody clones. High binding polystyrene ELISA plates (Corning, N.Y., USA) were coated O/N with 0.3 µg of toxin Cn2 (100 µl/well) in bicarbonate buffer 50 mM pH 9.4 at 4° C. Plates were washed thrice with PBS and Tween 0.1%, and then blocked with BSA 0.5% in PBS for 2 h at 37° C. Phage-antibody supernatants were added to each well, incubated for 1 h at 37° C. and the plates washed. Bound phage-antibodies were detected with horseradish peroxidase (HRP)-conjugated anti-M13 antibody (Amersham Pharmacia Biotech AB). HRP activity was detected by adding O-phenylenediamine substrate. The plates were read at 492 nm in an ELISA reader (Bio-RAD Model 2550). Clones that bound to Cn2 with absorbance values above 2 were considered as positive. Specific binding clones were sequenced.

Phage-antibody cross reactivity. Selected phage-antibodies were tested for specificity with different antigens by ELISA. High binding polystyrene immunoplates were coated with several proteins (toxins Cn2, Cll1, Cll2, FII, Pg5, Pg7 and Pg8, and BSA, casein and gelatin) in bicarbonate buffer 50 mM pH 9.4 at 4° C. O/N. One hundred µl of each selected variant containing $1 \times 10^{11}$ phage-antibodies/ml were added to the wells and detected as described. Bound phage-antibodies were detected with horseradish peroxidase (HRP)-conjugated anti-M13 antibody (Amersham Pharmacia Biotech AB). HRP activity was detected by adding O-phenylenediamine substrate. The plates were read at 492 nm in an ELISA reader (Bio-RAD Model 2550). Clones that bound to Cn2 with absorbance values above 2 were considered as positive. Specific binding clones were sequenced.

Directed evolution by error prone PCR. Selected clones from the constructed library after 4 rounds of biopanning, were subjected to mutagenesis. Two standard techniques of error-prone PCR were used to construct random mutant scFv libraries with different mutation rates, 0.66% (Cadwell, R. C. & Joyce, G. F. (1992) PCR Methods Appl 2, 28-33) and 2% (Leung, D. W., Chen, E. & Goeddel, D. V. (1989) Technique 1, 11-15). Both PCR products were mixed, digested with SfiI and NotI, gel-purified and then ligated into the phagemid PSYN2. Ligated DNA was electroporated into electrocompetent E. coli TG1 cells. Three cycles of evolution were performed and the variability (mutation rate) of each library was determined.

Indirect ELISA using scFv antibodies. Supernatants containing scFv antibodies (soluble proteins); were transferred to an ELISA plate previously coated and blocked. One hundred µl/well of a 1:2000 dilution of Anti-c-myc (Zymed Laboratories INC, San Francisco, Calif., USA) and HRP-Goat Anti-Mouse (Zymed Laboratories) antibodies, were added consecutively and incubated 1 h 37° C. HRP activity detection and plate reading were performed following the standard procedures (Marks, J. D., Hoogenboom, H. R., Bonnert, T. P., McCafferty, J., Griffiths, A. D. & Winter, G. (1991) J Mol Biol 222, 581-97).

Surface plasmon resonance measurements. Kinetic constants for the interaction between scFv proteins and immobilized Cn2 toxin were determined in a Biacore biosensor system (BIACORE X). Twenty four µg of Cn2 toxin were bound onto a CM5 sensor chip using an equimolar mix of N-hydroxysuccinimide (NHS) and N-ethyl-N-(dimethylaminopropil-carbodiimide) (EDC) in 200 mM MES buffer pH 4.7. Approximately 400 resonance units (RU) were coupled. The scFvs were diluted at various concentrations in HBS-EP buffer (Biacore) and 60 µl were injected over immobilized Cn2 at a rate of 30 µl/min with a delay in the injection of 600 seconds. Data (Kon, Koff and $K_D$) were analyzed using the BIAEVALUATION program version 3.2.

Competition by surface plasmon resonance (BCF2 and 6009F). SPR binding assays were employed to know if the matured scFv and the monoclonal BCF2 recognized the same epitope on Cn2 toxin. It was performed as described for anti-hen egg lysozyme (HEL) (Donini, M., Morea, V., Desiderio, A., Pashkoulov, D., Villani, M. E., Tramontano, A. & Benvenuto, E. (2003) J Mol Biol 330, 323-32). Six saturating amounts (60 µl of 200 nM) of BCF2 antibody were consecutively injected on a Cn2-coated chip at a rate of 30 µl/min in buffer HBS-EP. Afterwards, 60 µl of the 6009F scFv at a 5 nM concentration were injected and the sensogram was analyzed.

Competition by surface plasmon resonance (Alacramyn, BCF2 and 6009F). SPR binding assays were employed to know if the scFv 6009F and the Alacramyn polyclonal antibody fragments share any epitope on Cn2 toxin. It was performed as described for anti-hen egg lysozyme (HEL) (Donini, M., Morea, V., Desiderio, A., Pashkoulov, D., Villani, M. E., Tramontano, A. & Benvenuto, E. (2003) J Mol Biol 330, 323-32). Eight saturating amounts (40 µl of 200 nM) of Alacramyn F(ab')$_2$ were consecutively injected on a Cn2-coated chip at a rate of 10 µl/min in buffer HBS-EP. Afterwards, 40 µl of the BCF2 at 20 nM were injected. Finally, 40 µl of 6009F scFv at a 20 nM concentration were injected and the sensogram was analyzed.

EXAMPLES

Example 1

Construction of the Library of Human scFv

A human non-immune scFv library was prepared from a sample of 400 ml of peripheral blood lymphocytes provided by a *Centruroides limpidus limpidus* scorpion collector. Blood was centrifuged in a Ficoll gradient and lymphocytes were separated and washed. Total RNA was isolated and purified by Promega KIT. The cDNA was synthesized from total RNA by RT-PCR using random hexamers [Roche RT-PCR Kit (AMV), Indianapolis, Ind., USA]. Variable domain repertoires of immunoglobulin heavy chains were amplified from the cDNA by Vent DNA polymerase (New England Biolabs) in combination with each of the HuVH-FOR primers and an equimolar mixture of HuJHBACK primers (Marks, J. D., Hoogenboom, H. R., Bonnert, T. P., McCafferty, J., Griffiths, A. D. & Winter, G. (1991) J Mol Biol 222, 581-97) in independent reactions for each family. For light chain variable domains, a similar procedure was performed using each HuVκFOR and a mixture of HuJκBACK for κ chains and each HuVλFOR with a mixture of HuJλBACK for λ chains. The resulting fragments were re-amplified to append a DNA segment encoding half of the peptide linker [(Gly$_4$-Ser)$_3$] in independent reactions. The connector primers, SEQ.ID.NO: 1, SEQ.ID.NO: 2, SEQ.ID.NO: 3, SEQ.ID.NO: 4, SEQ.ID.NO: 5, SEQ.ID.NO: 6, SEQ.ID.NO: 7, SEQ.ID.NO: 8, SEQ.ID.NO: 9, SEQ.ID.NO: 10, SEQ.ID.NO: 11, SEQ.ID.NO: 12, SEQ.ID.NO: 13, SEQ.ID.NO: 14, SEQ.ID.NO: 15, SEQ.ID.NO: 16 and ID.NO: 17, were designed as described (Hawlisch, H., Meyer zu Vilsendorf, A., Bautsch, W., Klos, A. & Kohl, J. (2000) J Immunol Methods 236, 117-31). The PCR products were gel-purified and overlapped by PCR as described by Marks (1991). Each overlapped product (72 in total), was amplified in the same overlapping reaction mixture with primers as described by Marks (1991) that allowed the incorporation of SfiI and NotI restriction sites. The following program was used: denaturation at 95° C. for 5 min followed by 7 cycles of 1 min at 95° C., 1.5 min at 64° C., and 1 min at 72° C. without primers. Subsequently, external primers were added, followed by 30 cycles of 1 min at 95° C., 1 min at 64° C., and 1 min at 72° C. and a final extension at 72° C. for 10 min. Each PCR product was quantified and mixed in equimolar amounts to be digested. DNA segments were cut with restriction enzymes SfiI and NotI and gel-purified. The resulting DNA fragments were ligated into the phagemid PSYN2 (kindly provided by J. D. Marks, UCSF, San Francisco, Calif., USA) previously cut with restriction enzymes SfiI and NotI. Ligated DNA was electroporated into E. coli strain TG1. Twenty individual clones randomly chosen were analyzed by digestion with BstNI enzyme and sequenced. The sequences of the clones were determined with the primers forward (5' ATA CCT ATT GCC TAC GG C3', SEQ. ID. NO: 60) and reverse (5'TTT CAA CAG TCT ATG CGG3', SEQ. ID. NO: 61) in the Applied BioSystems sequencer Model 3100.

Example 2

Isolation of anti-Cn2 scFv by Panning of Phage Antibody Repertoires

The library of human scFv was displayed on filamentous phage by inducing the cell culture with Helper (M13K07 (New England Biolabs, Benerly, Mass. USA) and used for the selection of antibodies against Cn2 toxin. Biopanning was performed as described in methods. After four rounds of panning, 88 single phage-antibody clones were randomly picked, cultured and screened for specific binding to Cn2 by ELISA. High binding polystyrene ELISA plates (Corning, N.Y., USA) were coated O/N with 0.3 μg of toxin Cn2 (100 μl/well) in bicarbonate buffer 50 mM pH 9.4 at 4° C. Plates were washed thrice with PBS and Tween 0.1%, then blocked with BSA 0.5% in PBS for 2 h at 37° C. Phage-antibody supernatants were added to each well, incubated for 1 h at 37° C. and the plates washed. Bound phage-antibodies were detected with horseradish peroxidase (HRP)-conjugated anti-M13 antibody (Amersham Pharmacia Biotech AB). HRP activity was detected by adding O-phenylenediamine substrate. The plates were read at 492 nm in an ELISA reader (Bio-RAD Model 2550). Fifteen clones that bound to Cn2 with absorbance values above 2 were considered as positive and were sequenced and analyzed individually. Only two anti-Cn2 scFvs were identified and named scFv 3F and scFv C1 (FIG. 1). The nucleotide sequences were compared with the databases using the BLAST algorithm. The best scores corresponded to human immunoglobulins. They were also compared with the IMGT databases (Lefranc, M. P. (2003) *Nucleic Acids Res* 31, 307-10) to determine the corresponding germ lines. For clone 3F, the families $V_H3$-$V_K3$ were the closest for $V_H$ and $V_L$ domains respectively. In the case of C1, the families $V_H3$-$V_\lambda 1$ had the highest scores. The specificity of these two scFvs was determined by phage-ELISA (FIG. 2A). These two clones showed to be highly specific to Cn2 despite of its high identity with control toxins Cll1 and Cll2 (FIG. 2B). These scFvs were re-cloned into the expression vector PSYN1 in order to characterize them as soluble proteins.

Both antibody fragments were unable to protect the mice of toxin Cn2. The affinity constants were determined in a biosensor of molecular interactions in real time (BIA-CORE). Table 2 shows the values obtained for the binding kinetic constants. The dimeric form of both scFvs were constructed by means of shortening the linker from 15 to 7 amino acid residues by PCR. None of the diabodies 3F and C1 was able to neutralize the toxin in the protection assay.

TABLE 2

Kinetic Rates and Affinity Constants of the Soluble Proteins Corresponding to the scFvs 3F and C1

| scFv | Kon ($M^{-1}s^{-1}$) | SE (Kon) | Koff ($s^{-1}$) | SE (Koff) | $K_D$ (M) |
|---|---|---|---|---|---|
| C1 | $2.0 \times 10^4$ | $2.3 \times 10^2$ | $1.40 \times 10^{-2}$ | $6.9 \times 10^{-5}$ | $5.40 \times 10^{-7}$ |
| 3F | $7.0 \times 10^4$ | $1.7 \times 10^3$ | $1.28 \times 10^{-2}$ | $1.2 \times 10^{-4}$ | $1.83 \times 10^{-7}$ |

Kinetic rates and KD were calculated using BIA-EVALUATION 3.2 software.
SE means standard error.

Example 3

First Cycle of Maturation

In the first cycle of maturation, clone 3F was used as parent antibody subjected to directed evolution by error prone PCR as described in methods. A library of $1 \times 10^6$ variants (mutation rate 0.9%), obtained from scFv 3F was evaluated by phage display against Cn2 toxin. The variant 6F was selected, which had a change (Ser54Gly), at CDR2 of heavy chain. The kinetic constants of this mutant (Table 1), showed that the association and dissociation constants were improved approximately 7 fold and 1.5 fold respectively, resulting in an increment of one order of magnitude in the $K_D$ (from 183 nM to 16.8 nM; Table 1). These results show that scFv 6F binds more efficiently to the toxin but it still detaches rapidly, indicating that residue at position 54 plays an important role in the interaction of the antibody with the toxin Cn2.

Example 4

Second Cycle of Maturation

In the second cycle of maturation, the variant 6F selected in example 3 was used as parent antibody and subjected to directed evolution by error prone PCR as described in methods. A library of $1.6 \times 10^6$ variants of clone 6F (mutation rate 0.6%) was obtained and evaluated by phage display against Cn2 toxin, and the variant clone 610A was selected. This variant showed a second change at CDR3 of heavy chain (Val101Phe). This mutation improved both the association constant but more importantly the dissociation constant. This result suggests that residue 109 in the CDR3 of heavy chain also plays an important role in the binding to the toxin. The change of Val for Phe could result in a better interaction in terms of an increased area of contact. The accumulated changes at CDR2 and CDR3 in variant clone 610A, had a synergistic effect on the affinity constant obtaining an increment of 176 fold [183 nM (clone 3F) to 1.04 nM (clone 610A); Table 1], as determined by BIA-CORE.

Example 5

Third Cycle of Maturation

In the third cycle of maturation, the variant 610A selected in example 4 was used as parent antibody and subjected to directed evolution by error prone PCR as described in methods. A library of $1.0 \times 10^7$ variants of clone 610A (mutation rate 1%) was obtained and evaluated by phage display against Cn2 toxin, In this last maturation step, two alternative selection strategies were performed. The first was the standard procedure and the second included some stringent modifications intended to select improved variants in their affinity and stability. The modified biopanning method was performed according to the standard methods but with the following modifications: the immunotube was coated with 1 ml of Cn2 at 5 µg/ml_in NaHCO3 buffer, pH 9.4 at 4° C. instead of the 50 µg/ml used in the standard biopannig procedure used, the time of incubation was increased from 2 hours to 5 hours and the temperature was increased from 25° C. to 37° C. After the washing steps (20 washes with PBS-Tween20 (1x, 0.1%) and 20 washes with PBS), 1 ml of 100 mM triethylamine (TEA from Pierce, Ill., USA), was added to remove the less stable or low binding phage-antibodies. The incubation time was 30 minutes, after which the detached phages were eliminated. The immunotubes were rinsed with 1 ml of 1M Tris-HCl, pH 7 to neutralize the TEA and then washed thrice with PBS. The phage-antibodies that remained bound to Cn2 were recovered with *E. Coli* TG1 cells. The clones selected with this procedure were evaluated by ELISA as soluble proteins.

The standard procedure of phage selection gave a lower number of positive variants as compared to the more stringent procedure. The number of nucleotide changes in the selected clones from the two procedures was different. From this modified biopannig procedure variant clone 6009F was selected. The DNA sequence of clone 6009F showed six mutations, two silent mutations and four amino acid changes with respect to clone 610A (Table 1). One of these amino acid changes occurred at framework 3 of heavy chain (Asn74Asp) and the other 3 changes at light chain. Two of them (Thr152Ile and Ser197Gly) occurred at frameworks 1 and 3 respectively and the third one (Tyr164Phe), at CDR1 (Table 1). The analysis of affinity measurements [Table 2. and FIG. 6], revealed that variant clone 6009F had a $K_d$ of 410 pM, which is comparable to affinities of other neutralizing antibodies of scorpion toxins (Aubrey, N., Devaux, C., Sizaret, P. Y., Rochat, H., Goyffon, M. & Billiald, P. (2003) *Cell Mol Life Sci* 60, 617-28). The kinetic parameters shown in Table 1 reveal that both kinetic constants were improved about 2 fold as compared to clone 610A, resulting in an affinity constant as already mentioned, in the picomolar range, leading to a 446 fold increment in $K_d$ with respect to 3F scFv.

Example 6

Second Panning Selection for the Third Cycle of Mutagenesis

In a second pannig selection procedure the same mutation library generated in example 5 were used. Again, the procedure included the stringent modifications intended to select improved variants in their affinity and stability. The modified biopanning method was performed as mentioned in example 5, but this time a fewer amount of toxin was used to coat the immunotube (2.5, 1 and 0.5 µg/ml for the first, second and third biopannig cycles). After the washing steps, 1 ml of 100 mM TEA, was added to remove the less stable or low binding phage-antibodies. The incubation time was 30 minutes, after which the detached phages were eliminated. The immunotubes were rinsed with 1 ml of 1M Tris-HCl, pH 7 to neutralize the TEA and then washed thrice with PBS. The phage-antibodies that remained bound to Cn2 were recovered with *E. coli* TG1 cells. The clones selected with this procedure were evaluated by ELISA as soluble proteins.

From this modified biopannig procedure variant clones 6105F and 6103E were selected. The DNA sequence of clone 6105F showed 3 mutations, 1 silent mutation and 2 amino acid changes with respect to clone 610A (Table 1). One of these amino acid changes occurred at framework 3 of heavy chain (Asn74Asp) and the other change at light chain. The analysis of affinity measurements [Table 2. and FIG. 10], revealed that variant clone 6105F had a $K_d$ of 590 pM, which is comparable to affinities of other neutralizing antibodies of scorpion toxins (Aubrey, N., Devaux, C., Sizaret, P. Y., Rochat, H., Goyffon, M. & Billiald, P. (2003) *Cell Mol Life Sci* 60, 617-28). The kinetic parameters shown in Table 1 reveal that both kinetic constants were improved about 1.5-2 fold as compared to clone 610A, resulting in an affinity constant as already mentioned, in the picomolar range, leading to a 310 fold increment in $K_d$ with respect to 3F scFv. On the other hand, The DNA sequence of clone 6103E showed 4 mutations, 1 silent mutation and 3 amino acid changes with respect to clone 610A (Table 1). Two of these amino acid changes occurred at framework 3 of heavy chain (Asn74Asp) and the other changes at light chain. The analysis of affinity measurements [Table 2. and FIG. 11], revealed that variant clone 6103EF had a $K_d$ of 630 pM, which is comparable to affinities of other neutralizing antibodies of scorpion toxins (Aubrey, N., Devaux, C., Sizaret, P. Y., Rochat, H., Goyffon, M. & Billiald, P. (2003) *Cell Mol Life Sci* 60, 617-28). The kinetic parameters shown in Table 1 reveal that both kinetic constants were improved about 2-3 fold as compared to clone 610A, resulting in an affinity constant as already mentioned, in the picomolar range, leading to a 290 fold increment in $K_d$ with respect to 3F scFv.

Example 7

Expression of Single-chain Antibodies

To produce free and soluble of scFv of the present invention, for their evaluation in BIACORE, and for its evaluation and use as neutralizing agents against toxin Cn2 and total venom from *C. noxius*, the DNA fragments coding the scFv from any of clone C1 (SEQ. ID. NO: 18), 3F (SEQ. ID. NO: 24), and variant clones 6F (SEQ.ID.NO: 30), 610A (SEQ.ID.NO: 36), 6009F (SEQ.ID.NO: 42), 6D (SEQ.ID.NO: 48), 9C (SEQ.ID.NO: 54), 6003E (SEQ.ID.NO: 62), 6003G (SEQ.ID.NO: 68), 6010H (SEQ.ID.NO: 74), 6011G (SEQ.ID.NO: 80), 6105F (SEQ.ID.NO:86) and 6103E (SEQ.ID.NO:92) were ligated into an expression vector, in this case PSYN1. These constructs were transformed into a competent host, in this case *E. coli* strain TG1 was used. Five hundred ml of recombinant cells were grown until an $OD_{600}=0.7$ was reached (in YT2X, glucose 0.1% Amp 200 µg/ml) (Marks, J. D., Hoogenboom, H. R., Bonnert, T. P., McCafferty, J., Griffiths, A. D. & Winter, G. (1991) *J Mol Biol* 222, 581-97). Expression of the scFvs was induced with 1 mM isopropyl-β-D-thiogalactopyranoside (IPTG) and incubation continued 6 hours more. Then, the cells were harvested by centrifugation (6000 rpm, 10 min, at 4° C.). To release the recombinant proteins, the pellet was resuspended in 12.5 ml of PPB extraction buffer (20% sucrose/1 mM EDTA/30 mM Tris HCl adjusted to pH 8) and the mixture was incubated on ice for 20 min. Cells were centrifuged at 6000 rpm at 4° C. for 20 min. The scFv soluble protein present in the supernatant was collected.

For isolation, the pellet was resuspended in 5 mM MgSO$_4$, kept on ice for 20 min and centrifuged at 6000 rpm at 4° C. for 20 min. PPB and MgSO$_4$ supernatants were mixed and dialyzed twice against PBS 1×. The scFvs were isolated by Ni$^{2+}$-NTA affinity chromatography (QIAGEN, Germany) taking advantage of the 6 HIS that the vector adds to the expression product, and eluted with 1 ml of 250 mM imidazole. Finally, scFv preparations were further purified by gel filtration chromatography on a Superdex™ 75 column (Pharmacia Biotech AB, Uppsala, Sweden).

Example 8

Neutralization Assays

The purified scFv proteins were used to test their neutralization capacity against the toxic effects of Cn2 or the whole venom in mice. Groups of 10-20 female mice (CD1 strain) were injected with a mix of scFv and toxin Cn2 or venom. One or two LD$_{50}$ (0.25-0.5 µg/20 g of mouse weight) of Cn2 toxin or two LD$_{50}$ (5 µg/20 g of mouse weight) of whole venom, were mixed with each scFv at a final molecular ratio of 1:5 (toxin: scFv). The mix was incubated for 30 min a 37° C. and injected intraperitoneally. Three controls were used: venom, Cn2 or scFv were injected alone in independent assays. The number of animals was kept to a minimum but enough to validate the experiment. The protocols were approved by the Ethical Committee of Animal Care of the inventor's Institute.

TABLE 3

Neutralization Assays

| Sample | LD$_{50}$ | Molar ratio | Protected/injected |
|---|---|---|---|
| Cn2:6009F | | | |
| 6009F | | | 10/10 |
| Cn2 | 1 | none | 6/10 |
| Cn2 | 1 | 1:10 | 20/20 |
| Cn2 | 2 | none | 6/18 |
| Cn2 | 2 | 1:10 | 18/18 |
| Whole venom | 2 | none | 0/10 |
| Whole venom | 2 | 1:14[a] | 10/10 |
| Cn2:6105F | | | |
| Cn2 | 1 | none | 6/10 |
| Cn2 | 1 | 1:10 | 10/10 |
| Cn2 | 2 | 1:10 | 10/10 |
| Cn2:6103E | | | |
| Cn2 | 1 | none | 6/10 |
| Cn2 | 1 | 1:10 | 10/10 |
| Cn2 | 2 | 1:10 | 10/10 |

[a] = Estimated considering that Cn2 constitutes 6.8% of whole venom.
LD50 of Cn2 = 0.250 µg/20 g of mouse weight
Amount used of whole venom = 2.5 µg/20 g of mouse weight.

Results of mice groups challenged with Cn2 toxin or whole venom by intraperitoneal injection alone or in the presence of the indicated molar ratios of toxin: antibody.

The neutralization capacity against toxin Cn2 of soluble protein purified from clones 6F, 610A and 6009F was evaluated in CD1 mice. The scFv from clone 6009F was the only one that had the capacity to neutralize the toxin. When one lethal dose of toxin and five molar excess of the antibody were injected, all the mice survived as compared to the control (Table 3). Noteworthy, the mice did not present any symptom associated with envenoming (Dehesa-Davila, M. & Possani, L. D. (1994) *Toxicon* 32, 1015-8). The next step consisted in using two lethal doses of toxin. The mice did not show any poisoning signal, demonstrating the effectiveness of the evolved human antibody of the present invention (100% protection). In the case of whole venom (two lethal doses used only with the same amount of scFv), the mice were protected but they presented some symptoms like a respiratory distress but finally they recovered 7 hours later. We would like to emphasize that antibody 6009F is capable of completely neutralizing the lethal effect of two LD$_{50}$ of toxin Cn2 and confers a reasonably good protection against two lethal doses of whole venom. The scFv 6009F is stable after 4 weeks stored in PBS at 4° C., as it was shown by functional activity evaluation during 4 weeks. The scFv 6009F showed protective activity during this period of time, indicating that it is functionally stable, as expected from the stringent selection strategy (modified method) used.

Example 9

Competition Assays by Surface Plasmon Resonance (SPR)

Since the monoclonal antibody BCF2 neutralizes toxin Cn2 too, in order to know if the epitope recognized by clone 6009F was the same as the one recognized by BCF2, a displacement test using the Biacore was performed (FIG. 3). SPR binding assays were employed to know if the matured scFv and the monoclonal BCF2 recognized the same epitope on Cn2 toxin. It was performed as described (Donini, M., Morea, V., Desiderio, A., Pashkoulov, D., Villani, M. E., Tramontano, A. & Benvenuto, E. (2003) *J Mol Biol* 330, 323-32). Six saturating amounts (60 µl of 200 nM) of BCF2 antibody were consecutively injected on a Cn2-coated chip at a rate of 30 µl/min in buffer HBS-EP. Afterwards, 60 µl of the 6009F scFv at a 5 nM concentration were injected and the sensogram analyzed. The sensogram showed that 6009F antibody binds to toxin Cn2, in spite of having saturated the sites recognized by BCF2, which suggests that clone 6009F recognizes a different site (epitope).

These results were confirmed by competitive ELISA (see FIG. 7), in which the scFv 6009F was bound first, and then the toxin and BCF2 at last. Both antibodies remain bound to toxin Cn2, confirming once again that they are recognizing different epitopes.

Furthermore, the same procedure was used to know if the epitope recognized by clone 6009F was the same as any one of the epitopes recognized by a commercial polyclonal antibody F(ab')$_2$ antivenom raised against a pool o scorpion venoms, included the whole *C. noxius* venom (Alacramyn, by Instituto Bioclon S. A. de C. V., Mexico). The sensogram (FIG. 9) showed no increment in the signal after the injection of BCF2, meaning that BCF2 shares one of the epitopes recognized by the Alacramyn, while the injection of 6009F antibody rinsed the signal exactly as the control (that is the binding kinetics of 600F scFv to the Cn2 toxin) showing that 6009F recognizes a different site epitopes than the those recognized by in vivo produced antibodies (Alacramyn and BCF2).

REFERENCES

All publications, patents and patent publications cited herein are incorporated by reference in their entirety into the disclosure. The foregoing specification, including the specific embodiments and examples, are intended to be illustrative and not limiting. Numerous other variations and modifications can be effected without departing from the true spirit and scope of the present invention.

What is claimed is:

1. A composition comprising a human antibody that specifically recognizes the toxin Cn2, wherein said human antibody comprises a $V_H$ and a $V_L$, and further wherein said $V_H$ and $V_L$ pairs are selected from the group consisting of:
   (a) SEQ ID NO: 45 and SEQ ID NO: 47,
   (b) SEQ ID NO: 89 and SEQ ID NO: 91, and
   (c) SEQ ID NO: 95 and SEQ ID NO: 97.

2. The composition of claim 1, wherein said $V_H$ comprises SEQ. ID. NO: 45; wherein said $V_L$ comprises SEQ. ID. NO: 47; and wherein said human antibody is capable of neutralizing the toxin Cn2.

3. The composition of claim 1, wherein said $V_H$ comprises SEQ. ID. NO: 89; wherein said $V_L$ comprises SEQ. ID. NO: 91; and wherein said human antibody is capable of neutralizing the toxin Cn2.

4. The composition of claim 1, wherein said $V_H$ comprises SEQ. ID. NO: 95; wherein said $V_L$ comprises SEQ. ID. NO: 97; and wherein said human antibody is capable of neutralizing the toxin Cn2.

5. The composition of claim 1, wherein said human antibody comprises an amino acid sequence selected from the group consisting of: SEQ. ID. NO: 43, SEQ. ID. NO: 87 and SEQ. ID. NO: 93.

6. The composition of any one of claims 2-5, wherein said antibody neutralizes the in vivo effect of venom of the scorpion *Centruroides noxius*.

7. The composition of claim 6, wherein said antibody specifically binds the toxin Cn2 from *Centruroides noxius* venom.

8. A pharmaceutical composition comprising a human antibody that specifically recognizes the toxin Cn2, and a pharmaceutically acceptable carrier, wherein said antibody comprises a $V_H$ and a $V_L$, and further wherein said $V_H$ and $V_L$ pairs are selected from the group consisting of:
   (a) SEQ ID NO: 45 and SEQ ID NO: 47,
   (b) SEQ ID NO: 89 and SEQ ID NO: 91, and
   (c) SEQ ID NO: 95 and SEQ ID NO: 97.

9. The pharmaceutical composition of claim 8, wherein said $V_H$ comprises SEQ. ID. NO: 45; and wherein said $V_L$ comprises SEQ. ID. NO: 47.

10. The pharmaceutical composition of claim 8, wherein said $V_H$ comprises SEQ. ID. NO: 89; and wherein said $V_L$ comprises SEQ. ID. NO: 91.

11. The pharmaceutical composition of claim 8, wherein said $V_H$ comprises SEQ. ID. NO: 95; and wherein said $V_L$ comprises SEQ. ID. NO: 97.

12. The pharmaceutical composition of claim 8, wherein said human antibody comprises an amino acid sequence selected from the group consisting of: SEQ. ID. NO: 43, SEQ. ID. NO: 87 and SEQ. ID. NO 93.

13. The pharmaceutical composition of any one of claims 9-12, wherein said antibody neutralizes the in vivo effect venom of the scorpion *Centruroides noxius*.

14. The pharmaceutical composition of claim 13, wherein said antibody specifically binds the toxin Cn2 from *Centruroides noxius* venom.

15. A method for treating envenomation from *Centruroides noxius* scorpion comprising administering to a mammal in need of such treatment an effective amount of a pharmaceutical composition comprising a human antibody that specifically recognizes the toxin Cn2, wherein said antibody comprises a $V_H$ and a $V_L$, and further wherein said $V_H$ and $V_L$ pairs are selected from the group consisting of:
   (a) SEQ ID NO: 45 and SEQ ID NO: 47,
   (b) SEQ ID NO: 89 and SEQ ID NO: 91, and
   (c) SEQ ID NO: 95 and SEQ ID NO: 97;
   and wherein said human antibody neutralizes the in vivo effect of venom of scorpion *Centruroides noxius*.

16. The method of claim 15, wherein said $V_H$ comprises SEQ. ID. NO: 45; and wherein said $V_L$ comprises SEQ. ID. NO: 47.

17. The method of claim 15, wherein said $V_H$ comprises SEQ. ID. NO: 89; and wherein said $V_L$ comprises SEQ. ID. NO: 91.

18. The method of claim 15, wherein said $V_H$ comprises SEQ. ID. NO: 95; and wherein said $V_L$ comprises SEQ. ID. NO: 97.

19. The method of claim 15, wherein said human antibody comprises an amino acid sequence selected from the group consisting of: SEQ. ID. NO: 43, SEQ. ID. NO. 87 and SEQ. ID. NO: 93.

20. The method of claim 15, wherein said administration is selected from the group consisting of intravenous, subcutaneous, intramuscular, intravaginal, intraperitoneal, intranasal, oral and mucosal administration.

21. An isolated antibody that binds to the toxin Cn2, wherein said antibody comprises a heavy chain variable region domain comprising SEQ ID NO: 45.

22. An isolated antibody that binds to the toxin Cn2, wherein said antibody comprises a heavy chain variable region domain comprising SEQ ID NO: 89.

23. An isolated antibody that binds to the toxin Cn2, wherein said antibody comprises a heavy chain variable region domain comprising SEQ ID NO: 95.

24. An isolated antibody that binds to the toxin Cn2, wherein said antibody comprises a light chain variable region domain comprising SEQ ID NO: 47.

25. An isolated antibody that binds to the toxin Cn2, wherein said antibody comprises a light chain variable region domain comprising SEQ ID NO: 91.

26. An isolated antibody that binds to the toxin Cn2, wherein said antibody comprises a light chain variable region domain comprising SEQ ID NO: 97.

27. A method of detecting the Cn2 toxin in a sample comprising the steps of:
(a) adhering a human antibody that specifically recognizes the toxin Cn2 to a solid substrate, wherein said antibody comprises a $V_H$ and a $V_L$, and further wherein said $V_H$ and $V_L$ pairs are selected from the group consisting of:
  (i) SEQ ID NO: 45 and SEQ ID NO: 47,
  (ii) SEQ ID NO: 89 and SEQ ID NO: 91, and
  (iii) SEQ ID NO: 95 and SEQ ID NO: 97;
(b) adding a sample to the solid substrate of step (a), thereby forming an antibody-antigen complex; and
(c) detecting said complex of step (b), wherein the detection of the complex indicates the presence of toxin Cn2 in the sample.

28. The method of claim 27, wherein said human antibody is selected from the group consisting of: SEQ ID NO: 43, SEQ ID NO: 87 and SEQ ID NO: 93.

29. An isolated antibody, wherein said isolated antibody is encoded by the nucleic acid selected from the group consisting of:
  (i) SEQ ID NO: 44 and SEQ ID NO: 46,
  (ii) SEQ ID NO: 88 and SEQ ID NO: 90, and
  (iii) SEQ ID NO: 94 and SEQ ID NO: 96;
and wherein said antibody specifically recognizes the toxin Cn2.

30. An isolated antibody, wherein said isolated antibody is encoded the nucleic acid selected from the group consisting of SEQ. ID. NO: 42, SEQ. ID. NO: 86 and SEQ. ID. NO: 92, and wherein said antibody specifically recognizes the toxin Cn2.

* * * * *